US008563277B1

(12) United States Patent
Parekh et al.

(10) Patent No.: US 8,563,277 B1
(45) Date of Patent: Oct. 22, 2013

(54) METHODS AND SYSTEMS FOR SACCHARIFICATION OF BIOMASS

(71) Applicant: Sweetwater Energy, Inc., Rochester, NY (US)

(72) Inventors: Sarad Parekh, Pittsford, NY (US); Carl P. Felice, Churchville, NY (US)

(73) Assignee: Sweetwater Energy, Inc., Rochester, NY (US)

( * ) Notice: Subject to any disclaimer, the term of this patent is extended or adjusted under 35 U.S.C. 154(b) by 0 days.

(21) Appl. No.: 13/686,477

(22) Filed: Nov. 27, 2012

Related U.S. Application Data

(60) Provisional application No. 61/623,907, filed on Apr. 13, 2012, provisional application No. 61/623,881, filed on Apr. 13, 2012.

(51) Int. Cl.
*C12P 19/02* (2006.01)

(52) U.S. Cl.
USPC ........... 435/105; 435/100; 435/165; 435/183; 435/277; 127/2; 127/34; 127/37; 422/148; 426/69

(58) Field of Classification Search
None
See application file for complete search history.

(56) References Cited

U.S. PATENT DOCUMENTS 4,048,341 A 9/1977 Lagerstrom et al.
4,070,232 A 1/1978 Funk
4,182,780 A 1/1980 Lagerstrom et al.
4,201,596 A 5/1980 Church et al.
4,350,766 A 9/1982 Mehlberg
4,395,488 A 7/1983 Rowe
4,414,330 A 11/1983 Zucker et al.
4,447,534 A 5/1984 Moebus et al.
4,478,854 A 10/1984 Adler-nissen et al.
4,520,105 A 5/1985 Sinner et al.
4,600,590 A 7/1986 Dale
4,612,286 A 9/1986 Sherman et al.
4,615,742 A 10/1986 Wright
4,644,060 A 2/1987 Chou
4,650,689 A 3/1987 Hedrick
4,806,475 A 2/1989 Gould
5,037,663 A 8/1991 Dale
5,144,008 A 9/1992 Ikeda et al.
5,171,592 A 12/1992 Holtzapple et al.
5,177,008 A 1/1993 Kampen
5,177,009 A 1/1993 Kampen
5,473,061 A 12/1995 Bredereck et al.
5,693,296 A 12/1997 Holtzapple et al.
5,726,046 A 3/1998 Farone et al.
5,846,787 A 12/1998 Ladisch et al.
5,865,898 A 2/1999 Holtzapple et al.
5,916,780 A 6/1999 Foody et al.
5,939,544 A 8/1999 Karstens et al.
5,969,189 A 10/1999 Holtzapple et al.
5,986,133 A 11/1999 Holtzapple et al.
6,043,392 A 3/2000 Holtzapple et al.
6,106,888 A 8/2000 Dale et al.
6,176,176 B1 1/2001 Dale et al.
6,258,175 B1 7/2001 Lightner
6,262,313 B1 7/2001 Holtzapple et al.
6,332,542 B2 12/2001 Bilodeau et al.
6,365,732 B1 4/2002 Van Thorre
6,416,621 B1 7/2002 Karstens
6,478,965 B1 11/2002 Holtzapple et al.
6,509,180 B1 1/2003 Verser et al.
7,109,005 B2 9/2006 Eroma et al.
7,198,925 B2 4/2007 Foody
7,503,981 B2 3/2009 Wyman et al.
7,807,419 B2 10/2010 Hennessey et al.
7,909,895 B2 3/2011 Dickinson et al.
7,932,063 B2 4/2011 Dunson, Jr. et al.
7,932,065 B2 * 4/2011 Medoff ......................... 435/165
7,935,840 B2 5/2011 Leveson et al.
8,103,385 B2 1/2012 Macharia et al.
8,110,383 B2 2/2012 Jonsson et al.
8,123,864 B2 2/2012 Christensen et al.
8,168,840 B2 5/2012 Brady et al.
8,323,923 B1 12/2012 Horton
8,328,947 B2 12/2012 Anand et al.
8,426,161 B1 4/2013 Horton
2002/0038058 A1 3/2002 Holtzapple et al.
2002/0164730 A1 11/2002 Ballesteros Perdices et al.
2002/0164731 A1 11/2002 Eroma et al.
2002/0192774 A1 12/2002 Ahring et al.
2002/0197686 A1 12/2002 Lightner
2003/0109011 A1 6/2003 Hood et al.
2003/0199049 A1 10/2003 Nguyen et al.

(Continued)

FOREIGN PATENT DOCUMENTS

CA 1267407 B 4/1990
EP 1259466 B1 10/2008

(Continued)

OTHER PUBLICATIONS

U.S. Appl. No. 13/724,763, filed Dec. 21, 2012, Parekh et al.
U.S. Appl. No. 13/731,633, filed Dec. 31, 2012, Parekh et al.
U.S. Appl. No. 13/793,860, filed Mar. 11, 2013, Horton.
U.S. Appl. No. 13/842,941, filed Mar. 15, 2013, Parekh et al.
Alcohol and Tobacco Tax and Trade Bureau, treasury. 27 C.F.R. §19.134 Bonded warehouse not on premises qualified for production of spirits, p. 381, Apr. 1, 1997 revision.
Boggan. 2003. Alcohol, Chemistry and You Sources and Uses of Ethyl Alcohol. Kennesaw State University, pp. 1-5, http://www.chemcases.com/alcohol/alc-03.htm/.

(Continued)

*Primary Examiner* — Jon P Weber
*Assistant Examiner* — Chunyuan Luo
(74) *Attorney, Agent, or Firm* — Wilson Sonsini Goodrich & Rosati, P.C.

(57) ABSTRACT

Provided are methods and compositions for high yields while using reduced enzyme loads in saccharification and fermentation processes. These methods increase the efficiency of enzymes and result in improved yields and composition of saccharification and fermentation end products.

30 Claims, 9 Drawing Sheets

(56) References Cited

U.S. PATENT DOCUMENTS

| | | | | |
|---|---|---|---|---|
| 2003/0221361 | A1 | 12/2003 | Russell et al. | |
| 2003/0224088 | A1 | 12/2003 | Burdick | |
| 2004/0152881 | A1 | 8/2004 | Holtzapple et al. | |
| 2004/0168960 | A1 | 9/2004 | Holtzapple et al. | |
| 2004/0171136 | A1 | 9/2004 | Holtzapple et al. | |
| 2005/0054064 | A1 | 3/2005 | Talluri et al. | |
| 2005/0244934 | A1 | 11/2005 | Foody et al. | |
| 2005/0272134 | A1 | 12/2005 | Hughes | |
| 2006/0003064 | A1 | 1/2006 | James | |
| 2006/0024801 | A1 | 2/2006 | Holtzapple et al. | |
| 2006/0069244 | A1 | 3/2006 | Holtzapple et al. | |
| 2006/0188980 | A1 | 8/2006 | Holtzapple et al. | |
| 2006/0251764 | A1 | 11/2006 | Abbas et al. | |
| 2006/0281157 | A1 | 12/2006 | Chotani et al. | |
| 2007/0037259 | A1 | 2/2007 | Hennessey et al. | |
| 2007/0118916 | A1 | 5/2007 | Puzio et al. | |
| 2007/0148750 | A1 | 6/2007 | Hoshino et al. | |
| 2007/0190626 | A1 | 8/2007 | Wilkening et al. | |
| 2007/0275447 | A1 | 11/2007 | Lewis et al. | |
| 2008/0014617 | A1 | 1/2008 | Cerea | |
| 2008/0121359 | A1 | 5/2008 | Holtzapple et al. | |
| 2008/0176301 | A1 | 7/2008 | Granda et al. | |
| 2008/0227162 | A1 | 9/2008 | Varanasi et al. | |
| 2008/0280338 | A1 | 11/2008 | Hall et al. | |
| 2009/0042259 | A1 * | 2/2009 | Dale et al. | 435/105 |
| 2009/0043686 | A1 | 2/2009 | Matsumoto | |
| 2009/0064566 | A1 | 3/2009 | Brummerstedt Iversen et al. | |
| 2009/0098617 | A1 | 4/2009 | Burke et al. | |
| 2009/0298149 | A1 | 12/2009 | Wang et al. | |
| 2010/0021980 | A1 | 1/2010 | McDonald et al. | |
| 2010/0041119 | A1 | 2/2010 | Christensen et al. | |
| 2010/0055741 | A1 | 3/2010 | Galvez, II et al. | |
| 2010/0144001 | A1 | 6/2010 | Horton | |
| 2010/0221805 | A1 | 9/2010 | Kelly | |
| 2010/0221819 | A1 | 9/2010 | Foody et al. | |
| 2010/0227369 | A1 | 9/2010 | Narendranath et al. | |
| 2010/0317053 | A1 | 12/2010 | Stromberg et al. | |
| 2011/0079219 | A1 | 4/2011 | McDonald et al. | |
| 2011/0081689 | A1 | 4/2011 | Flanegan et al. | |
| 2011/0114765 | A1 | 5/2011 | Brady et al. | |
| 2011/0129886 | A1 | 6/2011 | Howard et al. | |
| 2011/0201084 | A1 | 8/2011 | Wyman et al. | |
| 2011/0244499 | A1 | 10/2011 | Realff | |
| 2011/0258911 | A1 | 10/2011 | Hanson et al. | |
| 2011/0258913 | A1 | 10/2011 | Stamires et al. | |
| 2011/0275860 | A1 | 11/2011 | Beldring et al. | |
| 2012/0006320 | A1 * | 1/2012 | Nguyen | 127/34 |
| 2012/0037325 | A1 | 2/2012 | Beldring et al. | |
| 2012/0041186 | A1 | 2/2012 | Pschorn et al. | |
| 2012/0100045 | A1 | 4/2012 | Beldring et al. | |
| 2012/0100577 | A1 | 4/2012 | Medoff et al. | |
| 2012/0122162 | A1 | 5/2012 | Romero et al. | |
| 2012/0190092 | A1 | 7/2012 | Jaquess et al. | |
| 2012/0214216 | A1 | 8/2012 | Brady et al. | |

FOREIGN PATENT DOCUMENTS

| | | | |
|---|---|---|---|
| EP | 1307735 | B1 | 11/2008 |
| EP | 1299170 | B1 | 8/2010 |
| JP | 2006-149343 | A | 6/2006 |
| WO | WO 01/32715 | A1 | 5/2001 |
| WO | WO 01/60752 | A1 | 8/2001 |
| WO | WO 02/00324 | A1 | 1/2002 |
| WO | WO 02/01220 | A2 | 1/2002 |
| WO | WO 02/01220 | A3 | 9/2002 |
| WO | WO 2004/081193 | A2 | 9/2004 |
| WO | WO 2004/113551 | A1 | 12/2004 |
| WO | WO 2005/087937 | A2 | 9/2005 |
| WO | WO 2005/118828 | A1 | 12/2005 |
| WO | WO 2006/024242 | A1 | 3/2006 |
| WO | WO 2006/101832 | A2 | 9/2006 |
| WO | WO 2007/009463 | A2 | 1/2007 |
| WO | WO 2007/009463 | A3 | 7/2007 |
| WO | WO 2008/020901 | A2 | 2/2008 |
| WO | WO 2006/101832 | A3 | 4/2009 |
| WO | WO 2009/063138 | A2 | 5/2009 |
| WO | WO 2010/056940 | A2 | 5/2010 |
| WO | WO 2010/115488 | A1 | 10/2010 |
| WO | WO 2011/103033 | A1 | 8/2011 |
| WO | WO 2012/051523 | A1 | 4/2012 |
| WO | WO 2012/099967 | A1 | 7/2012 |

OTHER PUBLICATIONS

Brigham, et al. Bacterial Carbon Storage to Value Added Products. J Microbial Biochem Technol 2011, S3-002.

Dale, et al. Hydrolysis of lignocellulosics at low enzyme levels: Application of the AFEX process. Bioresource Technology. Apr. 1996; 56(1):111-116.

Dasari, et al. The effect of particle size on hydrolysis reaction rates and rheological properties in cellulosic slurries. Appl Biochem Biotechnol. Apr. 2007;136-140(1-12):289-99. doi: 10.1007/s12010-007-9059-x.

Dowe, et al (SSF Experimental Protocols—Lignocellulosic Biomass Hydrolysis and Fermentation. Laboratory Analytical Procedure (LAP), Issue Date: Oct. 30, 2001. National Renewable Energy Laboratory, 1617 Cole Boulevard, Golden, Colorado 80401-3393, 76 pages).

Dowe, et al. 2001. SSF Experimental Protocols—Lignocellulosic Biomass Hydrolysis and Fermentation Laboratory Analytical Procedure (LAP), National Renewable Energy Laboratory. 1617 Cole Boulevard, Golden, Colorado. Issue Date: Oct. 30, 2001, pp. 1-18.

Felix et al. In vitro and in vivo digestibility of soya-bean straw treated with various alkalis. Anim Prod. 1990; 51:47-61.

Gibreel, et al. Fermentation of barley by using *Saccharomyces cerevisiae*: examination of barley as a feedstock for bioethanol production and value-added products. Appl Environ Microbiol. Mar. 2009;75(5):1363-72. doi: 10.1128/AEM.01512-08. Epub Dec. 29, 2008.

Gum,et al. Structural characterization of a glycoprotein cellulase, 1,4-beta-D-glucan cellubiohydrolase C from trichodermaviride. Biochem. Biophys. Acta. 1976; 446:370-86.

International search report and written opinion dated Jan. 26, 2010for PCT/US2009/67221.

Jones, et al. (1994, Ethanolic Fermentation of Blackstrap Molasses and Sugarcane Juice Using Very High Gravity Technology. J. Agric. Food Chem, vol. 42, pp. 1242-1246).

Kim, et al. Lime pretreatment and enzymatic hydrolysis of corn stover. Bioresour Technol. Dec. 2005;96(18):1994-2006.

Kim, et al. Pretreatment and fractionation of corn stover by ammonia recycle percolation process. Bioresour Technol. Dec. 2005;96(18):2007-13.

Larsson, et al. Comparison of different methods for the detoxification of lignocellulose hydrolyzates of spruce. Applied Biochemistry and Biotechnology. 1999; 77-79:91-103.

Lloyd, et al. Combined sugar yields for dilute sulfuric acid pretreatment of corn stover followed by enzymatic hydrolysis of the remaining solids. Bioresour Technol. Dec. 2005;96(18):1967-77.

Mosier, et al. Features of promising technologies for pretreatment of lignocellulosic biomass. Bioresour Technol. Apr. 2005;96(6):673-86.

Mosier, et al. Optimization of pH controlled liquid hot water pretreatment of corn stover. Bioresour Technol. Dec. 2005;96(18):1986-93.

Nevoigt, et al. Osmoregulation and glycerol metabolism in the yeast *Saccharomyces cerevisiae*. FEMS Microbiol Rev. Nov. 1997;21(3):231-41.

Notice of allowance dated Oct. 15, 2012 for U.S. Appl. No. 11/974,129.

Office action dated Mar. 20, 2013 for U.S. Appl. No. 12/633,555.

Office action dated May 24, 2010 for U.S. Appl. No. 11/974,129.

Office action dated Jul. 6, 2012 for U.S. Appl. No. 11/974,129.

Office action dated Oct. 3, 2012 for U.S. Appl. No. 12/633,555.

Office action dated Nov. 8, 2010 for U.S. Appl. No. 11/974,129.

Palmqvist, et al. Fermentation of lignocellulosic hydrolysates. I: inhibition and detoxification. Bioresource Technology. 2000; 74(1):17-24.

Parekh, et al. Production of glycerol by *Hansenula anomala*. Biotechnol Bioeng. Jul. 1985;27(7):1089-91.

(56) References Cited

OTHER PUBLICATIONS

Santoro, et al. A High-throughput Platform for Screening Milligram Quantities of Plant Biomass for Lignocellulose Digestibility. Bioenerg. Res. Jan. 2010;3:93-102.

Shapouri et al. 2006. The Economic Feasibility of Ethanol Production From Sugar in the United States, USDA, 78 Pages., Jul. 2006.

Sluiter, et al. Determination of structural carbohydrates and lignin in biomass. National Renewable Energy Laboratory. Technical report NREL/TP-510-42618. Revised Jun. 2010.

Taylor. From Raw Sugar to Raw materials. Chemical innovation. 2000; 30:45-48.

USDA, "The Economic Feasibility of Ethanol Production From Sugar in the United States"; Jul. 2006, 69 pages.

Varhegyi, et al. (1989. Kinetics of the thermal decomposition of cellulose, hemicellulose, and sugarcane bagasse. Energy Fuels, vol. 3, No. 3, pp. 329-335).

Waiss, et al. Improving Digestibility of Straws for Ruminant Feed by Aqueous Ammonia. Journal of Animal Science. 1972; 35(1):109-112.

Waltermann, et al. *Rhodococcus opacus* strain PD630 as a new source of high-value single-cell oil? Isolation and characterization of triacylglycerols and other storage lipids. Microbiology. 2000; 146:1143-1149.

Agbor, et al. Biomass pretreatment: fundamentals toward application. Biotechnol Adv. Nov.-Dec. 2011;29(6):675-85. doi: 10.1016/j.biotechadv.2011.05.005. Epub May 23, 2011.

International search report and written opinion dated Jun. 20, 2013 for PCT/US2013/036497.

International search report and written opinion dated May 30, 2013 for PCT/US2013/025457.

Office action dated Jun. 25, 2013 for U.S. Appl. No. 13/731,633.

* cited by examiner

METHODS AND SYSTEMS FOR SACCHARIFICATION OF BIOMASS

CROSS-REFERENCE

This application claims the benefit of U.S. Provisional Application No. 61/623,907, filed Apr. 13, 2012 and U.S. Provisional Application No. 61/623,881, filed Apr. 13, 2012, each of which application is incorporated herein by reference in its entirety.

BACKGROUND

Biomass is an abundant potential source of fuels and specialty chemicals. Any kind of biomass can be used to extract carbohydrates, proteins, fats, and other valuable compounds, but, in particular, the carbohydrate polymers of biomass derived from plants, algae or microorganisms are used to produce such products. Biomass generally includes three main structural elements: lignin, hemicellulose, and cellulose. Certain components (e.g., lignin) can reduce the chemical and physical accessibility of cellulose and hemicellulose, which in turn, reduces the susceptibility of these carbohydrate polymers to chemical and/or enzymatic conversion. Because of differences in the bonding of compounds in biomass and because of the presence of the lignin sheath, it can be more difficult to process the cellulose and hemicellulose in biomass than it is to process the starches in grains. Yet, in order to avoid the use of food crops, bioenergy facilities are being promoted that utilize the human inedible portions of biomass.

Many of the methods used to make the hemicellulose and cellulose of biomass more accessible can generate inhibitor compounds that can negatively affect downstream processing, such as saccharification and/or fermentation. There is a need for pretreatment process that provides a biomass fraction that is accessible to effective enzymatic hydrolysis without the formation or release of large volumes of inhibitors.

SUMMARY

In one aspect, disclosed herein are methods of producing a composition comprising C5 and C6 saccharides from a biomass composition comprising cellulose, hemicellulose, and/or lignocellulose, the methods comprising: (a) pretreating the biomass composition to produce a pretreated biomass composition comprising solid particles that are less than 1.5 mm in size and a yield of C5 monosaccharides and/or disaccharides that is at least 50% of a theoretical maximum, wherein pretreating comprises: (i) hydration of the biomass composition in a non-neutral pH aqueous medium to produce a hydrated biomass composition, (ii) mechanical size reduction of the hydrated biomass composition to produce the solid particles that are less than 1.5 mm in size, and (iii) heating the hydrated biomass composition for a time sufficient to produce the pretreated biomass composition comprising the yield of C5 monosaccharides and/or disaccharides that is at least 50% of the theoretical maximum; and (b) hydrolyzing the pretreated biomass composition with one or more enzymes for a time sufficient to produce the composition comprising C6 and C5 saccharides. In some embodiments, the size is length. In some embodiments, the size is diameter. In some embodiments, at least 50% of the solid particles in the pretreated biomass composition are from about 0.1 mm to about 1 mm in size. In some embodiments, at least 60% of the solid particles in the pretreated biomass composition are from about 0.1 mm to about 1 mm in size. In some embodiments, at least 70% of the solid particles in the pretreated biomass composition are from about 0.1 mm to about 1 mm in size. In some embodiments, at least 80% of the solid particles in the pretreated biomass composition are from about 0.1 mm to about 1 mm in size. In some embodiments, all of the solid particles in the pretreated biomass are less than 7.5 mm. In some embodiments, all of the solid particles in the pretreated biomass are less than 5 mm. In some embodiments, all of the solid particles in the pretreated biomass are less than 1 mm. In some embodiments, the C5 monosaccharides and/or disaccharides in the pretreated biomass composition are monosaccharides. In some embodiments, the yield of C5 monosaccharides and/or disaccharides is at least 60% of the theoretical maximum. In some embodiments, the yield of C5 monosaccharides and/or disaccharides is at least 70% of the theoretical maximum. In some embodiments, the yield of C5 monosaccharides and/or disaccharides is at least 80% of the theoretical maximum. In some embodiments, the yield of C5 monosaccharides and/or disaccharides is at least 85% of the theoretical maximum. In some embodiments, the pretreated biomass composition further comprises a yield of glucose that is less than about 20% of the theoretical maximum. In some embodiments, the pretreated biomass composition further comprises a yield of glucose that is less than about 15% of the theoretical maximum. In some embodiments, the pretreated biomass composition further comprises a yield of glucose that is less than about 10% of the theoretical maximum. In some embodiments, the pretreated biomass composition further comprises a yield of glucose that is less than about 5% of the theoretical maximum. In some embodiments, the hydrated biomass composition comprises from about 1% to about 20% solids by dry biomass weight. In some embodiments, the hydrated biomass composition comprises about 5% solids by dry biomass weight. In some embodiments, the non-neutral pH aqueous medium is at from about 30° C. to about 70° C. In some embodiments, the non-neutral pH aqueous medium is at from about 40° C. to about 60° C. In some embodiments, the non-neutral pH aqueous medium is at about 50° C. In some embodiments, hydration of the biomass composition is for about 1 minute to about 60 minutes. In some embodiments, hydration of the biomass composition is for about 5 minutes to about 30 minutes. In some embodiments, hydration of the biomass composition is for about 15 minutes to about 20 minutes. In some embodiments, heating of the biomass composition is at a temperature of from about 150° C. to about 200° C. In some embodiments, heating of the biomass composition is at a temperature of from about 160° C. to about 180° C. In some embodiments, heating of the biomass composition is performed at a pressure higher than atmospheric. In some embodiments, the pressure is from about 25 PSIG to about 250 PSIG. In some embodiments, the pressure is from about 75 PSIG to about 200 PSIG. In some embodiments, the pressure is from about 100 PSIG to about 150 PSIG. In some embodiments, the time sufficient to produce the yield of C5 monosaccharides and/or disaccharides is from about 1 minute to about 60 minutes. In some embodiments, the time sufficient to produce the yield of C5 monosaccharides and/or disaccharides is from about 5 minutes to about 30 minutes. In some embodiments, the time sufficient to produce the yield of C5 monosaccharides and/or disaccharides is from about 7.5 minutes to about 12.5 minutes. In some embodiments, pretreating the biomass composition further comprises dewatering the hydrated biomass composition to from about 10% to about 40% solids by dry biomass weight. In some embodiments, pretreating the biomass composition further comprises dewatering the hydrated biomass composition to about 30% solids by dry biomass weight. In some embodiments, heating comprises steam explosion, acid-catalyzed steam explosion, ammonia fiber/freeze explosion (AFEX), or a combination thereof. In some embodiments, the pretreating is performed in a single unit operation. In some embodiments, the single unit operation comprises one or more of a hydration unit, one or more rotating cutters, one or more pumps, a dewatering unit, a steam injection unit, a heating unit, a steam explosion unit, or a combination thereof. In some embodiments, the hydration unit is a vortex mixer outfitted with one or more rotating cutters. Some embodiments further comprise a rotating cutter that is outfitted with a plurality of cutting blades and a plurality of steam injection holes. In some embodiments, the pretreating is performed in a continuous mode of operation. In some embodiments, the continuous mode of operation comprises feeding the biomass composition to a hydration unit. In some embodiments, the hydration unit is a vortex mixer. In some embodiments, the pretreating is performed in a total time of from about 1 minute to about 3 hours. In some embodiments, the pretreating is performed in a total time of from about 5 minutes to about 90 minutes. In some embodiments, the pretreating is performed in a total time of from about 15 minutes to about 45 minutes. In some embodiments, the one or more enzymes comprise one or more cellulases. In some embodiments, the one or more enzymes comprise one or more hemicellulases. In some embodiments, the one or more enzymes comprise one or more cellulases and one or more hemicellulases. In some embodiments, the one or more enzymes do not comprise any hemicellulases. In some embodiments, the one or more enzymes is a cellulase and hemicellulase complex. In some embodiments, the cellulase and hemicellulase complex is not supplemented with additional hemicellulase enzymes. In some embodiments, the one or more enzymes are at a total level from about 1% to about 20% w/w by dry biomass weight. In some embodiments, the one or more enzymes are at a total level from about 1% to about 10% w/w by dry biomass weight. In some embodiments, the one or more enzymes are at a total level from about 1% to about 5% w/w by dry biomass weight. In some embodiments, the one or more enzymes are at a total level of less than 15% w/w by dry biomass weight. In some embodiments, the one or more enzymes are at a total level of less than 10% w/w by dry biomass weight. In some embodiments, the one or more enzymes are at a total level of less than 5% w/w by dry biomass weight. In some embodiments, the time sufficient to produce the composition comprising C6 and C5 saccharides is from about 10 hours to about 100 hours. In some embodiments, the time sufficient to produce the composition comprising C6 and C5 saccharides is from about 21 hours to about 50 hours. Some embodiments further comprise adjusting the water content and/or the pH of the pretreated biomass composition prior to hydrolyzing. In some embodiments, the water content of the pretreated biomass composition is adjusted to about 5% to about 30% solids by dry biomass weight. In some embodiments, the water content of the pretreated biomass composition is adjusted to about 5% to about 20% solids by dry biomass weight. In some embodiments, the pH of the pretreated biomass composition is adjusted to about 4 to about 7. In some embodiments, the pH of the pretreated biomass composition is adjusted to about 4.5 to about 5.5. In some embodiments, the hydrolyzing is done at a temperature of from about 30° C. to about 70° C. In some embodiments, the hydrolyzing is done at a temperature of from about 45° C. to about 60° C. In some embodiments, the composition comprising C6 and C5 saccharides comprises glucose, xylose, mannose, galactose, rhamnose, arabinose, or a combination thereof. In some embodiments, the composition comprising C5 and C6 saccharides is an aqueous composition. In some embodiments, the composition comprising C5 and C6 saccharides comprises glucose, xylose, mannose, galactose, rhamnose, arabinose, or a combination thereof. In some embodiments, the composition comprising C5 and C6 saccharides comprises a yield of glucose in a yield that is 50%, 55%, 60%, 65%, 70%, 75%, 80%, 85%, 90%, 91%, 92%, 93%, 94%, 95%, 96%, 97%, 98%, 99%, 99.5%, or 100% of a theoretical maximum. In some embodiments, the composition comprising C5 and C6 saccharides comprises a yield of xylose in a yield that is 50%, 55%, 60%, 65%, 70%, 75%, 80%, 85%, 90%, 91%, 92%, 93%, 94%, 95%, 96%, 97%, 98%, 99%, 99.5%, or 100% of a theoretical maximum. In some embodiments, the theoretical maximum is mass of a given monosaccharide assuming 100% conversion of the oligosaccharides comprising the given monosaccharide in the biomass composition. In some embodiments, the theoretical maximum is the mass of a given monosaccharide measured after hydrolysis of the biomass composition with 72% sulfuric acid. In some embodiments, the composition comprising C6 and C5 saccharides comprises glucose in a yield that is greater than 55% of a theoretical maximum at 21 hours of hydrolysis. In some embodiments, the composition comprising C6 and C5 saccharides comprises glucose in a yield that is greater than 60% of a theoretical maximum at 21 hours of hydrolysis. In some embodiments, the composition comprising C6 and C5 saccharides comprises glucose in a yield that is greater than 70% of a theoretical maximum at 21 hours of hydrolysis. In some embodiments, the composition comprising C6 and C5 saccharides comprises glucose in a yield that is greater than 80% of a theoretical maximum at 21 hours of hydrolysis. In some embodiments, the composition comprising C6 and C5 saccharides comprises glucose in a yield that is greater than 90% of a theoretical maximum at 21 hours of hydrolysis. In some embodiments, the composition comprising C6 and C5 saccharides comprises glucose in a yield that is greater than 70% of a theoretical maximum at 48 hours of hydrolysis. In some embodiments, the composition comprising C6 and C5 saccharides comprises glucose in a yield that is greater than 80% of a theoretical maximum at 48 hours of hydrolysis. In some embodiments, the composition comprising C6 and C5 saccharides comprises glucose in a yield that is greater than 90% of a theoretical maximum at 48 hours of hydrolysis. In some embodiments, the composition comprising C6 and C5 saccharides comprises glucose in a yield that is greater than 95% of a theoretical maximum at 48 hours of hydrolysis. In some embodiments, the composition comprising C6 and C5 saccharides comprises xylose in a yield that is greater than 60% of a theoretical maximum at 21 hours of hydrolysis. In some embodiments, the composition comprising C6 and C5 saccharides comprises xylose in a yield that is greater than 70% of a theoretical maximum at 21 hours of hydrolysis. In some embodiments, the composition comprising C6 and C5 saccharides comprises xylose in a yield that is greater than 80% of a theoretical maximum at 21 hours of hydrolysis. In some embodiments, the composition comprising C6 and C5 saccharides comprises xylose in a yield that is greater than 90% of a theoretical maximum at 21 hours of hydrolysis. In some embodiments, the biomass composition comprises alfalfa, algae, bagasse, bamboo, corn stover, corn cobs, corn kernels, corn mash, corn steep liquor, corn steep solids, distiller's grains, distiller's dried solubles, distiller's dried grains, condensed distiller's solubles, distiller's wet grains, distiller's dried grains with solubles, eucalyptus, food waste, fruit peels, garden residue, grass, grain hulls, modified crop plants, municipal waste, oat hulls, paper, paper pulp, prairie bluestem, poplar, rice hulls, seed hulls, silage, sorghum, straw, sugarcane, switchgrass, wheat, wheat straw, wheat bran, de-starched wheat bran, willows, wood, plant cells, plant tissue cultures, tissue cultures, or a combination thereof. In some embodiments, the method is for industrial scale production. In some embodiments, industrial scale production comprises pretreating greater than 1 metric ton (MT) in 24 hours. In some embodiments, industrial scale production comprises pretreating greater than 20 MT in 24 hours. In some embodiments, industrial scale production comprises pretreating greater than 50 MT in 24 hours. In some embodiments, industrial scale production comprises pretreating greater than 100 MT in 24 hours. In some embodiments, mechanical size reduction does not comprise hammer milling. In some embodiments, mechanical size reduction does not comprise colloid milling. In some embodiments, mechanical size reduction does not comprise bead milling. In some embodiments, mechanical size reduction does not comprise milling. In some embodiments, mechanical size reduction does not comprise homogenization. In some embodiments, mechanical size reduction does not comprise high pressure bursting.

Also disclosed herein are compositions comprising C5 and C6 saccharides produced by any of the methods disclosed herein. In some embodiments, the composition comprising C5 and C6 saccharides is an aqueous composition. In some embodiments, the composition comprising C5 and C6 saccharides comprises glucose, xylose, mannose, galactose, rhamnose, arabinose, or a combination thereof. In some embodiments, the composition comprising C5 and C6 saccharides comprises a yield of glucose in a yield that is 50%, 55%, 60%, 65%, 70%, 75%, 80%, 85%, 90%, 91%, 92%, 93%, 94%, 95%, 96%, 97%, 98%, 99%, 99.5%, or 100% of a theoretical maximum. In some embodiments, the composition comprising C5 and C6 saccharides comprises a yield of xylose in a yield that is 50%, 55%, 60%, 65%, 70%, 75%, 80%, 85%, 90%, 91%, 92%, 93%, 94%, 95%, 96%, 97%, 98%, 99%, 99.5%, or 100% of a theoretical maximum. In some embodiments, the theoretical maximum is mass of a given monosaccharide assuming 100% conversion of the oligosaccharides comprising the given monosaccharide in the biomass composition. In some embodiments, the theoretical maximum is the mass of a given monosaccharide measured after hydrolysis of the biomass composition with 72% sulfuric acid.

In another aspect, disclosed herein are methods of producing a composition comprising C5 and C6 saccharides from a biomass composition comprising cellulose, hemicellulose, and/or lignocellulose, the methods comprising: (a) pretreating the biomass composition to produce a pretreated biomass composition comprising solid particles that are less than 1.5 mm in size and a yield of C5 monosaccharides and/or disaccharides that is at least 50% of a theoretical maximum, wherein pretreating comprises: (i) hydration of the biomass composition in a non-neutral pH aqueous medium to produce a hydrated biomass composition, (ii) mechanical size reduction of the hydrated biomass composition to produce the solid particles that are less than 1.5 mm in size, wherein mechanical size reduction comprises cutting with a first rotating cutter and a second rotating cutter, and (iii) heating the hydrated biomass composition for a time sufficient to produce the pretreated biomass composition comprising the yield of C5 monosaccharides and disaccharides that is at least 50% of a theoretical maximum; and (b) hydrolyzing the pretreated biomass composition with one or more enzymes for a time sufficient to produce the composition comprising C5 and C6 saccharides. In some embodiments, the size is length. In some embodiments, the size is diameter. In some embodiments, at least 50% of the solid particles in the pretreated biomass composition are from about 0.1 mm to about 1 mm in size. In some embodiments, at least 60% of the solid particles in the pretreated biomass composition are from about 0.1 mm to about 1 mm in size. In some embodiments, at least 70% of the solid particles in the pretreated biomass composition are from about 0.1 mm to about 1 mm in size. In some embodiments, at least 80% of the solid particles in the pretreated biomass composition are from about 0.1 mm to about 1 mm in size. In some embodiments, all of the solid particles in the pretreated biomass are less than 7.5 mm. In some embodiments, all of the solid particles in the pretreated biomass are less than 5 mm. In some embodiments, all of the solid particles in the pretreated biomass are less than 1 mm. In some embodiments, the C5 monosaccharides and/or disaccharides in the pretreated biomass composition are monosaccharides. In some embodiments, the yield of C5 monosaccharides and/or disaccharides is at least 60% of the theoretical maximum. In some embodiments, the yield of C5 monosaccharides and/or disaccharides is at least 70% of the theoretical maximum. In some embodiments, the yield of C5 monosaccharides and/or disaccharides is at least 80% of the theoretical maximum. In some embodiments, the yield of C5 monosaccharides and/or disaccharides is at least 85% of the theoretical maximum. In some embodiments, the pretreated biomass composition further comprises a yield of glucose that is less than about 20% of the theoretical maximum. In some embodiments, the pretreated biomass composition further comprises a yield of glucose that is less than about 15% of the theoretical maximum. In some embodiments, the pretreated biomass composition further comprises a yield of glucose that is less than about 10% of the theoretical maximum. In some embodiments, the pretreated biomass composition further comprises a yield of glucose that is less than about 5% of the theoretical maximum. In some embodiments, heating of the biomass composition is at a temperature of from about 100° C. to about 250° C. In some embodiments, heating of the biomass composition is at a temperature of from about 150° C. to about 200° C. In some embodiments, heating of the biomass composition is at a temperature of from about 160° C. to about 180° C. In some embodiments, heating of the biomass composition is performed at a pressure higher than atmospheric. In some embodiments, the pressure is from about 25 PSIG to about 250 PSIG. In some embodiments, the pressure is from about 75 PSIG to about 200 PSIG. In some embodiments, the pressure is from about 100 PSIG to about 150 PSIG. In some embodiments, the time sufficient to produce the yield of C5 monosaccharides and/or disaccharides is from about 1 minute to about 60 minutes. In some embodiments, the time sufficient to produce the yield of C5 monosaccharides and/or disaccharides is from about 5 minutes to about 30 minutes. In some embodiments, the time sufficient to produce the yield of C5 monosaccharides and/or disaccharides is from about 7.5 minutes to about 12.5 minutes. In some embodiments, the hydrated biomass composition comprises from about 1% to about 20% solids by dry biomass weight. In some embodiments, the hydrated biomass composition comprises about 5% solids by dry biomass weight. In some embodiments, the non-neutral pH aqueous medium is at from about 30° C. to about 70° C. In some embodiments, the non-neutral pH aqueous medium is at from about 40° C. to about 60° C. In some embodiments, the non-neutral pH aqueous medium is at about 50° C. In some embodiments, hydration of the biomass composition is for about 1 minute to about 60 minutes. In some embodiments, hydration of the biomass composition is for about 5 minutes to about 30 minutes. In some embodiments, hydration of the biomass composition is for about 15 minutes to about 20 minutes. In some embodiments, hydration of the biomass composition is performed in a vortex mixer. In some embodiments, the non-neutral aqueous medium comprises an acid or a base at from about 0.1% to about 5% v/w by dry biomass weight. In some embodiments, the non-neutral pH aqueous medium comprises the acid that is sulfuric acid, peroxyacetic acid, lactic acid, formic acid, acetic acid, citric acid, phosphoric acid, hydrochloric acid, sulfurous acid, chloroacetic acid, dichloroacetic acid, trichloroacetic acid, trifluoroacetic acid, oxalic acid, benzoic acid, or a combination thereof. In some embodiments, the non-neutral pH aqueous medium comprises the base that is sodium hydroxide, calcium hydroxide, potassium hydroxide, ammonia, ammonia hydroxide, hydrogen peroxide or a combination thereof. In some embodiments, the non-neutral aqueous medium comprises sulfuric acid at from about 0.1% to about 5% v/w by dry biomass weight. In some embodiments, the non-neutral aqueous medium comprises sulfuric acid at from about 0.1% to about 2.5% v/w by dry biomass weight. In some embodiments, the non-neutral aqueous medium comprises sulfuric acid at about 1.8% v/w by dry biomass weight. In some embodiments, the non-neutral aqueous medium comprises sulfuric acid at about 1% v/w by dry biomass weight. In some embodiments, mechanical size reduction further comprises steam injection, steam explosion, acid-catalyzed steam explosion, ammonia fiber/freeze explosion (AFEX) or a combination thereof. In some embodiments, mechanical size reduction comprises simultaneous cutting and steam injection. In some embodiments, the second rotating cutter comprises a plurality of cutting blades and a plurality of steam-injection holes. In some embodiments, mechanical size reduction further comprises steam injection and steam explosion. In some embodiments, pretreating the biomass composition further comprises dewatering the hydrated biomass composition to from about 10% to about 40% solids by dry biomass weight. In some embodiments, pretreating the biomass composition further comprises dewatering the hydrated biomass composition to about 30% solids by dry biomass weight. In some embodiments, heating comprises steam explosion, acid-catalyzed steam explosion, ammonia fiber/freeze explosion (AFEX), or a combination thereof. In some embodiments, the pretreating is performed in a single unit operation. In some embodiments, the single unit operation comprises one or more of a hydration unit, one or more rotating cutters, one or more pumps, a dewatering unit, a steam injection unit, a heating unit, a steam explosion unit, or a combination thereof. In some embodiments, the hydration unit is a vortex mixer outfitted with one or more rotating cutters. Some embodiments comprise a rotating cutter that is outfitted with a plurality of cutting blades and a plurality of steam injection holes. In some embodiments, the pretreating is performed in a continuous mode of operation. In some embodiments, the continuous mode of operation comprises feeding the biomass composition to a hydration unit. In some embodiments, the hydration unit is a vortex mixer. In some embodiments, the pretreating is performed in a total time of from about 1 minutes to about 3 hours. In some embodiments, the pretreating is performed in a total time of from about 5 minutes to about 90 minutes. In some embodiments, the pretreating is performed in a total time of from about 15 minutes to about 45 minutes. In some embodiments, the one or more enzymes comprise one or more cellulases. In some embodiments, the one or more enzymes comprise one or more hemicellulases. In some embodiments, the one or more enzymes comprise one or more cellulases and one or more hemicellulases. In some embodiments, the one or more enzymes do not comprise any hemicellulases. In some embodiments, the one or more enzymes is a cellulase and hemicellulase complex. In some embodiments, the cellulase and hemicellulase complex is not supplemented with additional hemicellulase enzymes. In some embodiments, the one or more enzymes are at a total level from about 1% to about 20% w/w by dry biomass weight. In some embodiments, the one or more enzymes are at a total level from about 1% to about 10% w/w by dry biomass weight. In some embodiments, the one or more enzymes are at a total level from about 1% to about 5% w/w by dry biomass weight. In some embodiments, the one or more enzymes are at a total level of less than 15% w/w by dry biomass weight. In some embodiments, the one or more enzymes are at a total level of less than 10% w/w by dry biomass weight. In some embodiments, the one or more enzymes are at a total level of less than 5% w/w by dry biomass weight. In some embodiments, the time sufficient to produce the composition comprising C6 and C5 saccharides is from about 10 hours to about 100 hours. In some embodiments, the time sufficient to produce the composition comprising C6 and C5 saccharides is from about 21 hours to about 50 hours. Some embodiments further comprise adjusting the water content and/or the pH of the pretreated biomass composition prior to hydrolyzing. In some embodiments, the water content of the pretreated biomass composition is adjusted to about 5% to about 30% solids by dry biomass weight. In some embodiments, the water content of the pretreated biomass composition is adjusted to about 5% to about 20% solids by dry biomass weight. In some embodiments, the pH of the pretreated biomass composition is adjusted to about 4 to about 7. In some embodiments, the pH of the pretreated biomass composition is adjusted to about 4.5 to about 5.5. In some embodiments, the hydrolyzing is done at a temperature of from about 30° C. to about 70° C. In some embodiments, the hydrolyzing is done at a temperature of from about 45° C. to about 60° C. In some embodiments, the composition comprising C6 and C5 saccharides comprises glucose, xylose, mannose, galactose, rhamnose, arabinose, or a combination thereof. In some embodiments, the composition comprising C5 and C6 saccharides is an aqueous composition. In some embodiments, the composition comprising C5 and C6 saccharides comprises glucose, xylose, mannose, galactose, rhamnose, arabinose, or a combination thereof. In some embodiments, the composition comprising C5 and C6 saccharides comprises a yield of glucose in a yield that is 50%, 55%, 60%, 65%, 70%, 75%, 80%, 85%, 90%, 91%, 92%, 93%, 94%, 95%, 96%, 97%, 98%, 99%, 99.5%, or 100% of a theoretical maximum. In some embodiments, the composition comprising C5 and C6 saccharides comprises a yield of xylose in a yield that is 50%, 55%, 60%, 65%, 70%, 75%, 80%, 85%, 90%, 91%, 92%, 93%, 94%, 95%, 96%, 97%, 98%, 99%, 99.5%, or 100% of a theoretical maximum. In some embodiments, the theoretical maximum is mass of a given monosaccharide assuming 100% conversion of the oligosaccharides comprising the given monosaccharide in the biomass composition. In some embodiments, the theoretical maximum is the mass of a given monosaccharide measured after hydrolysis of the biomass composition with 72% sulfuric acid. In some embodiments, the composition comprising C6 and C5 saccharides comprises glucose in a yield that is greater than 55% of a theoretical maximum at 21 hours of hydrolysis. In some embodiments, the composition comprising C6 and C5 saccharides comprises glucose in a yield that is greater than 60% of a theoretical maximum at 21 hours of hydrolysis. In some embodiments, the composition comprising C6 and C5 saccharides comprises glucose in a yield that is greater than 70% of a theoretical maximum at 21 hours of hydrolysis. In some embodiments, the composition comprising C6 and C5 saccharides comprises glucose in a yield that is greater than 80% of a theoretical maximum at 21 hours of hydrolysis. In some embodiments, the composition comprising C6 and C5 saccharides comprises glucose in a yield that is greater than 90% of a theoretical maximum at 21 hours of hydrolysis. In some embodiments, the composition comprising C6 and C5 saccharides comprises glucose in a yield that is greater than 70% of a theoretical maximum at 48 hours of hydrolysis. In some embodiments, the composition comprising C6 and C5 saccharides comprises glucose in a yield that is greater than 80% of a theoretical maximum at 48 hours of hydrolysis. In some embodiments, the composition comprising C6 and C5 saccharides comprises glucose in a yield that is greater than 90% of a theoretical maximum at 48 hours of hydrolysis. In some embodiments, the composition comprising C6 and C5 saccharides comprises glucose in a yield that is greater than 95% of a theoretical maximum at 48 hours of hydrolysis. In some embodiments, the composition comprising C6 and C5 saccharides comprises xylose in a yield that is greater than 60% of a theoretical maximum at 21 hours of hydrolysis. In some embodiments, the composition comprising C6 and C5 saccharides comprises xylose in a yield that is greater than 70% of a theoretical maximum at 21 hours of hydrolysis. In some embodiments, the composition comprising C6 and C5 saccharides comprises xylose in a yield that is greater than 80% of a theoretical maximum at 21 hours of hydrolysis. In some embodiments, the composition comprising C6 and C5 saccharides comprises xylose in a yield that is greater than 90% of a theoretical maximum at 21 hours of hydrolysis. In some embodiments, the biomass composition comprises alfalfa, algae, bagasse, bamboo, corn stover, corn cobs, corn kernels, corn mash, corn steep liquor, corn steep solids, distiller's grains, distiller's dried solubles, distiller's dried grains, condensed distiller's solubles, distiller's wet grains, distiller's dried grains with solubles, eucalyptus, food waste, fruit peels, garden residue, grass, grain hulls, modified crop plants, municipal waste, oat hulls, paper, paper pulp, prairie bluestem, poplar, rice hulls, seed hulls, silage, sorghum, straw, sugarcane, switchgrass, wheat, wheat straw, wheat bran, de-starched wheat bran, willows, wood, plant cells, plant tissue cultures, tissue cultures, or a combination thereof. In some embodiments, the methods are for industrial scale production. In some embodiments, industrial scale production comprises pretreating greater than 1 metric ton (MT) in 24 hours. In some embodiments, industrial scale production comprises pretreating greater than 20 MT in 24 hours. In some embodiments, industrial scale production comprises pretreating greater than 50 MT in 24 hours. In some embodiments, industrial scale production comprises pretreating greater than 100 MT in 24 hours. In some embodiments, mechanical size reduction does not comprise hammer milling. In some embodiments, mechanical size reduction does not comprise colloid milling. In some embodiments, mechanical size reduction does not comprise bead milling. In some embodiments, mechanical size reduction does not comprise milling. In some embodiments, mechanical size reduction does not comprise homogenization. In some embodiments, mechanical size reduction does not comprise high pressure bursting.

In another aspect, disclosed herein are methods of producing a composition comprising C5 and C6 saccharides from a biomass composition comprising cellulose, hemicellulose, and/or lignocellulose, the methods comprising: (a) pretreating the biomass composition comprising cellulose, hemicellulose, and/or lignocellulose to produce a pretreated biomass composition comprising solid particles that are less than 1.5 mm in size and a yield of C5 monosaccharides and/or disaccharides that is at least 50% of a theoretical maximum, wherein pretreating comprises: (i) hydration of the biomass composition in an aqueous medium comprising an acid at 0.1 to 5% w/w or v/w by dry biomass weight, and (ii) mechanical size reduction of the hydrated biomass composition to produce the solid particles that are less than 1.5 mm in size, (iii) heating the hydrated biomass composition for a time sufficient to produce the pretreated biomass composition comprising the yield of C5 monosaccharides and disaccharides that is at least 50% of a theoretical maximum; and (b) hydrolyzing the cellulose, hemicellulose, and/or lignocellulose of the pretreated biomass composition with one or more enzymes for a time sufficient to produce the composition comprising C6 and C5 saccharides. In some embodiments, the size is length. In some embodiments, the size is diameter. In some embodiments, at least 50% of the solid particles in the pretreated biomass composition are from about 0.1 mm to about 1 mm in size. In some embodiments, at least 60% of the solid particles in the pretreated biomass composition are from about 0.1 mm to about 1 mm in size. In some embodiments, at least 70% of the solid particles in the pretreated biomass composition are from about 0.1 mm to about 1 mm in size. In some embodiments, at least 80% of the solid particles in the pretreated biomass composition are from about 0.1 mm to about 1 mm in size. In some embodiments, all of the solid particles in the pretreated biomass are less than 7.5 mm. In some embodiments, all of the solid particles in the pretreated biomass are less than 5 mm. In some embodiments, all of the solid particles in the pretreated biomass are less than 1 mm. In some embodiments, the C5 monosaccharides and/or disaccharides in the pretreated biomass composition are monosaccharides. In some embodiments, the yield of C5 monosaccharides and/or disaccharides is at least 60% of the theoretical maximum. In some embodiments, the yield of C5 monosaccharides and/or disaccharides is at least 70% of the theoretical maximum. In some embodiments, the yield of C5 monosaccharides and/or disaccharides is at least 80% of the theoretical maximum. In some embodiments, the yield of C5 monosaccharides and/or disaccharides is at least 85% of the theoretical maximum. In some embodiments, the pretreated biomass composition further comprises a yield of glucose that is less than about 20% of the theoretical maximum. In some embodiments, the pretreated biomass composition further comprises a yield of glucose that is less than about 15% of the theoretical maximum. In some embodiments, the pretreated biomass composition further comprises a yield of glucose that is less than about 10% of the theoretical maximum. In some embodiments, the pretreated biomass composition further comprises a yield of glucose that is less than about 5% of the theoretical maximum. In some embodiments, heating of the biomass composition is at a temperature of from about 100° C. to about 250° C. In some embodiments, heating of the biomass composition is at a temperature of from about 150° C. to about 200° C. In some embodiments, heating of the biomass composition is at a temperature of from about 160° C. to about 180° C. In some embodiments, heating of the biomass composition is performed at a pressure higher than atmospheric. In some embodiments, the pressure is from about 25 PSIG to about 250 PSIG. In some embodiments, the pressure is from about 75 PSIG to about 200 PSIG. In some embodiments, the pressure is from about 100 PSIG to about 150 PSIG. In some embodiments, the time sufficient to produce the yield of C5 monosaccharides and/or disaccharides is from about 1 minute to about 60 minutes. In some embodiments, the time sufficient to produce the yield of C5 monosaccharides and/or disaccharides is from about 5 minutes to about 30 minutes. In some embodiments, the time sufficient to produce the yield of C5 monosaccharides and/or disaccharides is from about 7.5 minutes to about 12.5 minutes. In some embodiments, the hydrated biomass composition comprises from about 1% to about 20% solids by dry biomass weight. In some embodiments, the hydrated biomass composition comprises about 5% solids by dry biomass weight. In some embodiments, the non-neutral pH aqueous medium is at from about 30° C. to about 70° C. In some embodiments, the non-neutral pH aqueous medium is at from about 40° C. to about 60° C. In some embodiments, the non-neutral pH aqueous medium is at about 50° C. In some embodiments, hydration of the biomass composition is for about 1 minute to about 60 minutes. In some embodiments, hydration of the biomass composition is for about 5 minutes to about 30 minutes. In some embodiments, hydration of the biomass composition is for about 15 minutes to about 20 minutes. In some embodiments, hydration of the biomass composition is performed in a vortex mixer. In some embodiments, the acid is sulfuric acid, peroxyacetic acid, lactic acid, formic acid, acetic acid, citric acid, phosphoric acid, hydrochloric acid, sulfurous acid, chloroacetic acid, dichloroacetic acid, trichloroacetic acid, trifluoroacetic acid, oxalic acid, benzoic acid, or a combination thereof. In some embodiments, the acid is sulfuric acid. In some embodiments, the non-neutral aqueous medium comprises sulfuric acid at from about 0.1% to about 2.5% v/w by dry biomass weight. In some embodiments, the non-neutral aqueous medium comprises sulfuric acid at about 1.8% v/w by dry biomass weight. In some embodiments, the non-neutral aqueous medium comprises sulfuric acid at about 1% v/w by dry biomass weight. In some embodiments, mechanical size reduction comprises cutting, chipping, grinding, milling, shredding, screening, shearing, steam injection, steam explosion, acid-catalyzed steam explosion, ammonia fiber/freeze explosion (AFEX) or a combination thereof. In some embodiments, mechanical size reduction comprises milling that is hammer milling, ball milling, bead milling, pan milling, colloid milling, or a combination thereof. In some embodiments, mechanical size reduction comprises simultaneous cutting and steam injection. In some embodiments, mechanical size reduction comprises steam injection, cutting, and steam explosion. In some embodiments, mechanical size reduction comprises simultaneous cutting and steam injection using a rotating cutter with a plurality of cutting blades and a plurality of steam-injection holes. In some embodiments, pretreating the biomass composition further comprises dewatering the hydrated biomass composition to from about 10% to about 40% solids by dry biomass weight. In some embodiments, pretreating the biomass composition further comprises dewatering the hydrated biomass composition to about 30% solids by dry biomass weight. In some embodiments, pretreating further comprises steam explosion, acid-catalyzed steam explosion, ammonia fiber/freeze explosion (AFEX), or a combination thereof. In some embodiments, the pretreating is performed in a single unit operation. In some embodiments, the single unit operation comprises one or more of a hydration unit, one or more rotating cutters, one or more pumps, a dewatering unit, a steam injection unit, a heating unit, a steam explosion unit, or a combination thereof. In some embodiments, the hydration unit is a vortex mixer outfitted with one or more rotating cutters. Some embodiments comprise a rotating cutter that is outfitted with a plurality of cutting blades and a plurality of steam injection holes. In some embodiments, the pretreating is performed in a continuous mode of operation. In some embodiments, the continuous mode of operation comprises feeding the biomass composition to a hydration unit. In some embodiments, the hydration unit is a vortex mixer. In some embodiments, the pretreating is performed in a total time of from about 1 minute to about 3 hours. In some embodiments, the pretreating is performed in a total time of from about 5 minutes to about 90 minutes. In some embodiments, the pretreating is performed in a total time of from about 15 minutes to about 45 minutes. In some embodiments, the one or more enzymes comprise one or more cellulases. In some embodiments, the one or more enzymes comprise one or more hemicellulases. In some embodiments, the one or more enzymes comprise one or more cellulases and one or more hemicellulases. In some embodiments, the one or more enzymes do not comprise any hemicellulases. In some embodiments, the one or more enzymes is a cellulase and hemicellulase complex. In some embodiments, the cellulase and hemicellulase complex is not supplemented with additional hemicellulase enzymes. In some embodiments, the one or more enzymes are at a total level from about 1% to about 20% w/w by dry biomass weight. In some embodiments, the one or more enzymes are at a total level from about 1% to about 10% w/w by dry biomass weight. In some embodiments, the one or more enzymes are at a total level from about 1% to about 5% w/w by dry biomass weight. In some embodiments, the one or more enzymes are at a total level of less than 15% w/w by dry biomass weight. In some embodiments, the one or more enzymes are at a total level of less than 10% w/w by dry biomass weight. In some embodiments, the one or more enzymes are at a total level of less than 5% w/w by dry biomass weight. In some embodiments, the time sufficient to produce the composition comprising C6 and C5 saccharides is from about 10 hours to about 100 hours. In some embodiments, the time sufficient to produce the composition comprising C6 and C5 saccharides is from about 21 hours to about 50 hours. Some embodiments further comprise adjusting the water content and/or the pH of the pretreated biomass composition prior to hydrolyzing. In some embodiments, the water content of the pretreated biomass composition is adjusted to about 5% to about 30% solids by dry biomass weight. In some embodiments, the water content of the pretreated biomass composition is adjusted to about 5% to about 20% solids by dry biomass weight. In some embodiments, the pH of the pretreated biomass composition is adjusted to about 4 to about 7. In some embodiments, the pH of the pretreated biomass composition is adjusted to about 4.5 to about 5.5. In some embodiments, the hydrolyzing is done at a temperature of from about 30° C. to about 70° C. In some embodiments, the hydrolyzing is done at a temperature of from about 45° C. to about 60° C. In some embodiments, the composition comprising C6 and C5 saccharides comprises glucose, xylose, mannose, galactose, rhamnose, arabinose, or a combination thereof. In some embodiments, the composition comprising C5 and C6 saccharides is an aqueous composition. In some embodiments, the composition comprising C5 and C6 saccharides comprises glucose, xylose, mannose, galactose, rhamnose, arabinose, or a combination thereof. In some embodiments, the composition comprising C5 and C6 saccharides comprises a yield of glucose in a yield that is 50%, 55%, 60%, 65%, 70%, 75%, 80%, 85%, 90%, 91%, 92%, 93%, 94%, 95%, 96%, 97%, 98%, 99%, 99.5%, or 100% of a theoretical maximum. In some embodiments, the composition comprising C5 and C6 saccharides comprises a yield of xylose in a yield that is 50%, 55%, 60%, 65%, 70%, 75%, 80%, 85%, 90%, 91%, 92%, 93%, 94%, 95%, 96%, 97%, 98%, 99%, 99.5%, or 100% of a theoretical maximum. In some embodiments, the theoretical maximum is mass of a given monosaccharide assuming 100% conversion of the oligosaccharides comprising the given monosaccharide in the biomass composition. In some embodiments, the theoretical maximum is the mass of a given monosaccharide measured after hydrolysis of the biomass composition with 72% sulfuric acid. In some embodiments, the composition comprising C6 and C5 saccharides comprises glucose in a yield that is greater than 55% of a theoretical maximum at 21 hours of hydrolysis. In some embodiments, the composition comprising C6 and C5 saccharides comprises glucose in a yield that is greater than 60% of a theoretical maximum at 21 hours of hydrolysis. In some embodiments, the composition comprising C6 and C5 saccharides comprises glucose in a yield that is greater than 70% of a theoretical maximum at 21 hours of hydrolysis. In some embodiments, the composition comprising C6 and C5 saccharides comprises glucose in a yield that is greater than 80% of a theoretical maximum at 21 hours of hydrolysis. In some embodiments, the composition comprising C6 and C5 saccharides comprises glucose in a yield that is greater than 90% of a theoretical maximum at 21 hours of hydrolysis. In some embodiments, the composition comprising C6 and C5 saccharides comprises glucose in a yield that is greater than 70% of a theoretical maximum at 48 hours of hydrolysis. In some embodiments, the composition comprising C6 and C5 saccharides comprises glucose in a yield that is greater than 80% of a theoretical maximum at 48 hours of hydrolysis. In some embodiments, the composition comprising C6 and C5 saccharides comprises glucose in a yield that is greater than 90% of a theoretical maximum at 48 hours of hydrolysis. In some embodiments, the composition comprising C6 and C5 saccharides comprises glucose in a yield that is greater than 95% of a theoretical maximum at 48 hours of hydrolysis. In some embodiments, the composition comprising C6 and C5 saccharides comprises xylose in a yield that is greater than 60% of a theoretical maximum at 21 hours of hydrolysis. In some embodiments, the composition comprising C6 and C5 saccharides comprises xylose in a yield that is greater than 70% of a theoretical maximum at 21 hours of hydrolysis. In some embodiments, the composition comprising C6 and C5 saccharides comprises xylose in a yield that is greater than 80% of a theoretical maximum at 21 hours of hydrolysis. In some embodiments, the composition comprising C6 and C5 saccharides comprises xylose in a yield that is greater than 90% of a theoretical maximum at 21 hours of hydrolysis. In some embodiments, the biomass composition comprises alfalfa, algae, bagasse, bamboo, corn stover, corn cobs, corn kernels, corn mash, corn steep liquor, corn steep solids, distiller's grains, distiller's dried solubles, distiller's dried grains, condensed distiller's solubles, distiller's wet grains, distiller's dried grains with solubles, eucalyptus, food waste, fruit peels, garden residue, grass, grain hulls, modified crop plants, municipal waste, oat hulls, paper, paper pulp, prairie bluestem, poplar, rice hulls, seed hulls, silage, sorghum, straw, sugarcane, switchgrass, wheat, wheat straw, wheat bran, de-starched wheat bran, willows, wood, plant cells, plant tissue cultures, tissue cultures, or a combination thereof. In some embodiments, the method is for industrial scale production. In some embodiments, industrial scale production comprises pretreating greater than 1 metric ton (MT) in 24 hours. In some embodiments, industrial scale production comprises pretreating greater than 20 MT in 24 hours. In some embodiments, industrial scale production comprises pretreating greater than 50 MT in 24 hours. In some embodiments, industrial scale production comprises pretreating greater than 100 MT in 24 hours. In some embodiments, mechanical size reduction does not comprise hammer milling. In some embodiments, mechanical size reduction does not comprise colloid milling. In some embodiments, mechanical size reduction does not comprise bead milling. In some embodiments, mechanical size reduction does not comprise milling. In some embodiments, mechanical size reduction does not comprise homogenization. In some embodiments, mechanical size reduction does not comprise high pressure bursting.

In another aspect, disclosed herein are methods for producing a composition comprising saccharides from a biomass comprising cellulose, hemicellulose, and/or lignocellulose, the methods comprising: (a) processing the biomass composition comprising cellulose, hemicellulose, and/or lignocellulose to produce a pretreated biomass composition having solid particles that are less than 1.5 mm in size and at least an 80% yield of C5 monomers and/or dimers, wherein processing comprises: (i) hydrating and cutting the biomass composition by feeding the biomass composition to a vortex mixer comprising at a rate that maintains a solids level of about 5% w/w by dry biomass weight, wherein the vortex mixer comprises: 1) an aqueous medium containing an acid at a level that is from about 0.1% to about 5% w/w by dry biomass weight, wherein the aqueous medium is at about 50° C., 2) one or more rotating cutters, wherein the rotating cutters generate a vortex in the aqueous medium that mixes the biomass composition and the aqueous medium and pulls the biomass composition into the blades to produce a first cut biomass composition, (ii) dewatering the first cut biomass composition to produce a solids plug comprising about 30% w/w solids by dry biomass weight, (iii) simultaneously heating and fine-cutting the solids plug by feeding the solids plug to a rotating cutter comprising: 1) a plurality of blades, wherein the plurality of blades fine-cut the biomass plug to produce a second cut biomass composition comprising solid particles that are less than 1.5 mm in size, and 2) a plurality of microholes, wherein steam is injected into the second cut biomass composition through the plurality of microholes to maintain a temperature of from about 160° C. to 180° C. and a pressure of about 135 psig, (iv) heating the second-cut biomass composition for a time sufficient to produce at least an 80% yield of monomer and dimer C5 saccharides, and (v) subjecting the solids plug to steam explosion to produce the first pretreated biomass composition having solid particles that are less than 1.5 mm in size; (b) optionally separating the soluble C5 saccharides from the solids; (c) adding water to the solids to from about 5% to about 25% solids by dry weight; (d) adding enzymes in an amount from 0.5 kg per kg biomass to about 20 kg per kg biomass; and (e) hydrolyzing the biomass for a time sufficient to the composition comprising C5 and C6 saccharides.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features disclosed herein are set forth with particularity in the appended claims. A better understanding of the features and advantages will be obtained by reference to the following detailed description that sets forth illustrative embodiments, in which the principles of the disclosure are utilized, and the accompanying drawings of which:

DETAILED DESCRIPTION

Figure 1:
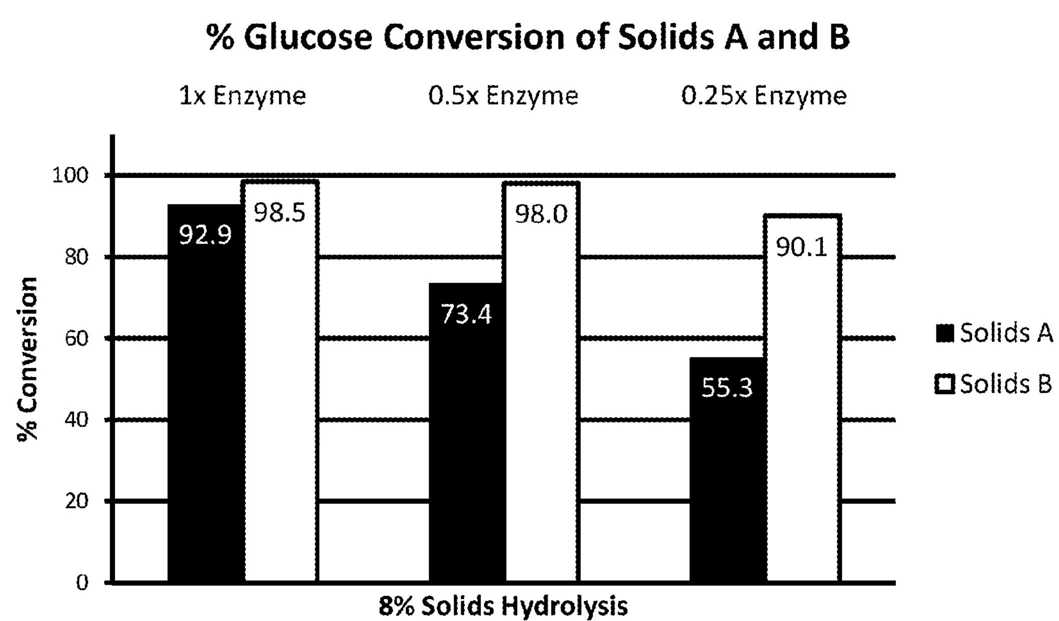
FIG. 1 shows glucose conversion from cellulose using 1×, 0.5×, and 0.25× enzyme loading with 8% solids.
Figure 2:
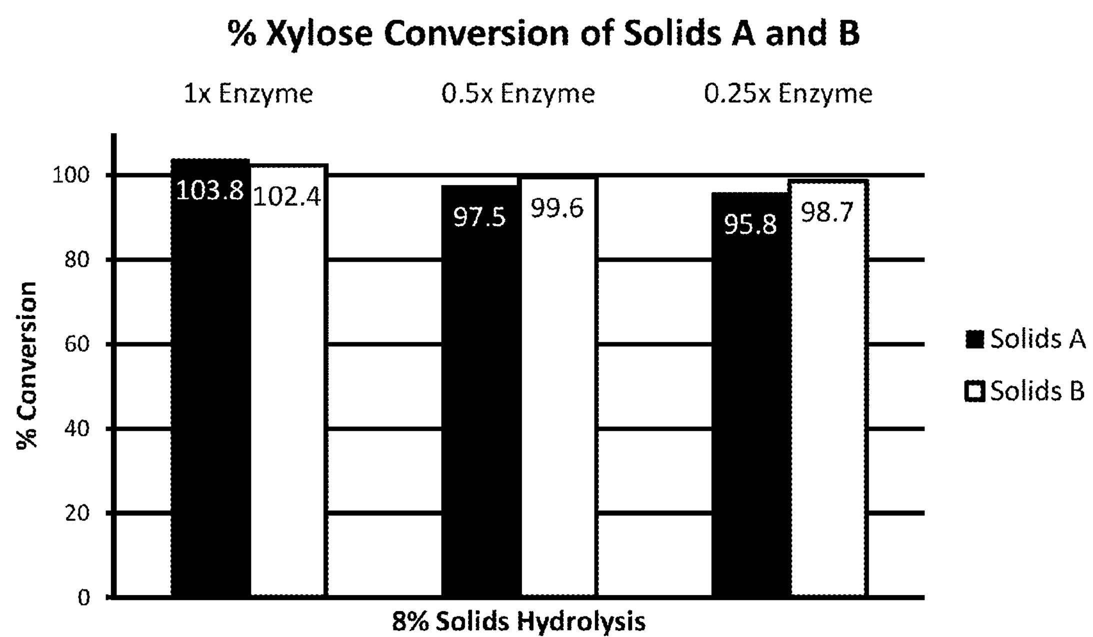
FIG. 2 shows xylose conversion from hemicellulose using 1×, 0.5×, and 0.25× enzyme loading with 8% solids.
Figure 3:
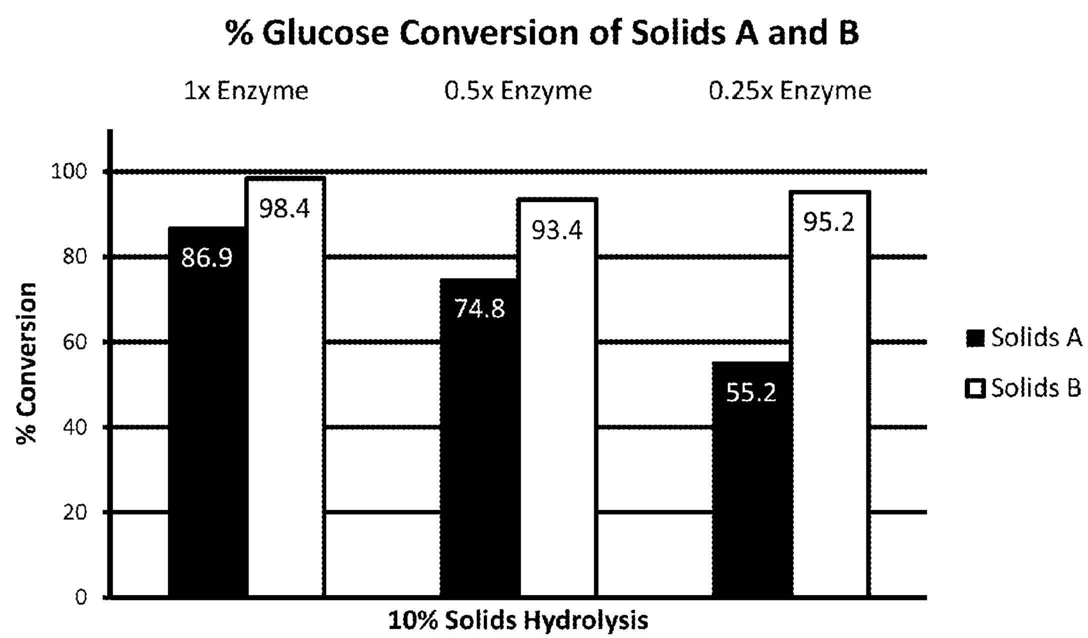
FIG. 3 shows glucose conversion from cellulose using 1×, 0.5×, and 0.25× enzyme loading with 10% solids.
Figure 4:
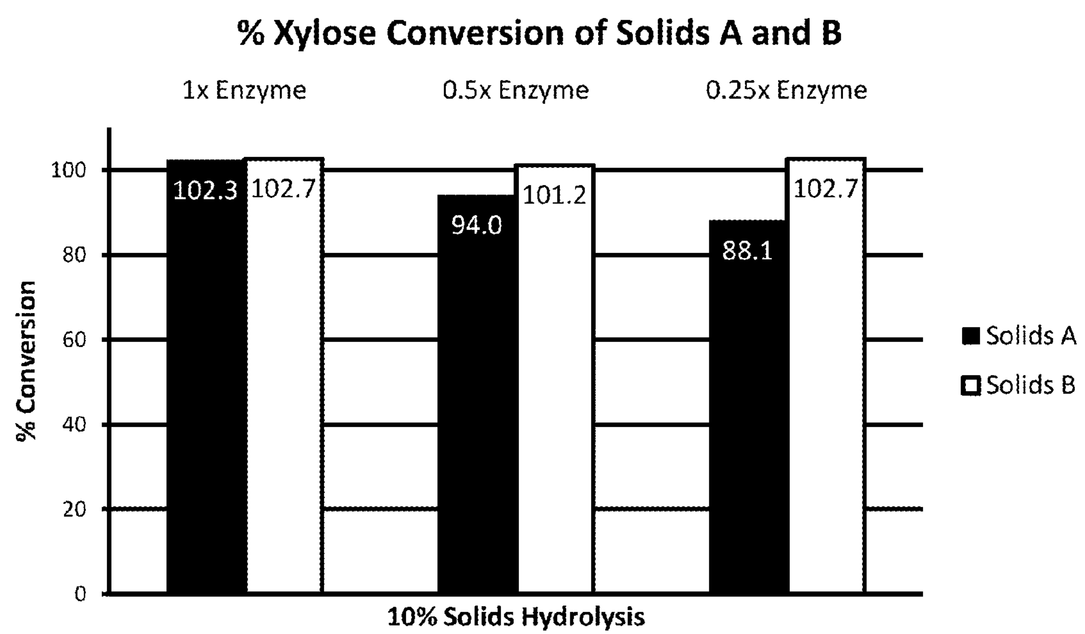
FIG. 4 shows xylose conversion from hemicellulose using 1×, 0.5×, and 0.25× enzyme loading with 10% solids.

As used in the specification and the appended claims, the singular forms "a," "an" and "the" include plural referents unless the context clearly dictates otherwise. Thus, for example, reference to "a purified monomer" includes mixtures of two or more purified monomers. The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that can vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Wherever the phrase "for example," "such as," "including" and the like are used herein, the phrase "and without limitation" is understood to follow unless explicitly stated otherwise. Therefore, "for example ethanol production" means "for example and without limitation ethanol production."

In this specification and in the claims that follow, reference will be made to a number of terms which shall be defined to have the following meanings. Unless characterized otherwise, technical and scientific terms used herein have the same meaning as commonly understood by one of ordinary skill in the art.

DEFINITIONS

"Optional" or "optionally" means that the subsequently described event or circumstance may or may not occur, and that the description includes instances where said event or circumstance occurs and instances where it does not. For example, the phrase "the medium can optionally contain glucose" means that the medium may or may not contain glucose as an ingredient and that the description includes both media containing glucose and media not containing glucose.

"About" means a referenced numeric indication plus or minus 10% of that referenced numeric indication. For example, the term about 4 would include a range of 3.6 to 4.4.

"Fermentive end-product" and "fermentation end-product" are used interchangeably herein to include biofuels, chemicals, compounds suitable as liquid fuels, gaseous fuels, triacylglycerols (TAGs), reagents, chemical feedstocks, chemical additives, processing aids, food additives, bioplastics and precursors to bioplastics, and other products. Examples of fermentive end-products include but are not limited to 1,4 diacids (succinic, fumaric and malic), 2,5 furan dicarboxylic acid, 3 hydroxy propionic acid, aspartic acid, glucaric acid, glutamic acid, itaconic acid, levulinic acid, 3-hydroxybutyrolactone, glycerol, sorbitol, xylitol/arabinitol, butanediol, butanol, methane, methanol, ethane, ethene, ethanol, n-propane, 1-propene, 1-propanol, propanal, acetone, propionate, n-butane, 1-butene, 1-butanol, butanal, butanoate, isobutanal, isobutanol, 2-methylbutanal, 2-methylbutanol, 3-methylbutanal, 3-methylbutanol, 2-butene, 2-butanol, 2-butanone, 2,3-butanediol, 3-hydroxy-2-butanone, 2,3-butanedione, ethylbenzene, ethenylbenzene, 2-phenylethanol, phenylacetaldehyde, 1-phenylbutane, 4-phenyl-1-butene, 4-phenyl-2-butene, 1-phenyl-2-butene, 1-phenyl-2-butanol, 4-phenyl-2-butanol, 1-phenyl-2-butanone, 4-phenyl-2-butanone, 1-phenyl-2,3-butandiol, 1-phenyl-3-hydroxy-2-butanone, 4-phenyl-3-hydroxy-2-butanone, 1-phenyl-2,3-butanedione, n-pentane, ethylphenol, ethenylphenol, 2-(4-hydroxyphenyl)ethanol, 4-hydroxyphenylacetaldehyde, 1-(4-hydroxyphenyl)butane, 4-(4-hydroxyphenyl)-1-butene, 4-(4-hydroxyphenyl)-2-butene, 1-(4-hydroxyphenyl)-1-butene, 1-(4-hydroxyphenyl)-2-butanol, 4-(4-hydroxyphenyl)-2-butanol, 1-(4-hydroxyphenyl)-2-butanone, 4-(4-hydroxyphenyl)-2-butanone, 1-(4-hydroxyphenyl)-2,3-butandiol, 1-(4-hydroxyphenyl)-3-hydroxy-2-butanone, 4-(4-hydroxyphenyl)-3-hydroxy-2-butanone, 1-(4-hydroxyphenyl)-2,3-butanonedione, indolylethane, indolylethene, 2-(indole-3-)ethanol, n-pentane, 1-pentene, 1-pentanol, pentanal, pentanoate, 2-pentene, 2-pentanol, 3-pentanol, 2-pentanone, 3-pentanone, 4-methylpentanal, 4-methylpentanol, 2,3-pentanediol, 2-hydroxy-3-pentanone, 3-hydroxy-2-pentanone, 2,3-pentanedione, 2-methylpentane, 4-methyl-1-pentene, 4-methyl-2-pentene, 4-methyl-3-pentene, 4-methyl-2-pentanol, 2-methyl-3-pentanol, 4-methyl-2-pentanone, 2-methyl-3-pentanone, 4-methyl-2,3-pentanediol, 4-methyl-2-hydroxy-3-pentanone, 4-methyl-3-hydroxy-2-pentanone, 4-methyl-2,3-pentanedione, 1-phenylpentane, 1-phenyl-1-pentene, 1-phenyl-2-pentene, 1-phenyl-3-pentene, 1-phenyl-2-pentanol, 1-phenyl-3-pentanol, 1-phenyl-2-pentanone, 1-phenyl-3-pentanone, 1-phenyl-2,3-pentanediol, 1-phenyl-2-hydroxy-3-pentanone, 1-phenyl-3-hydroxy-2-pentanone, 1-phenyl-2,3-pentanedione, 4-methyl-1-phenylpentane, 4-methyl-1-phenyl-1-pentene, 4-methyl-1-phenyl-2-pentene, 4-methyl-1-phenyl-3-pentene, 4-methyl-1-phenyl-3-pentanol, 4-methyl-1-phenyl-2-pentanol, 4-methyl-1-phenyl-3-pentanone, 4-methyl-1-phenyl-2-pentanone, 4-methyl-1-phenyl-2,3-pentanediol, 4-methyl-1-phenyl-2,3-pentanedione, 4-methyl-1-phenyl-3-hydroxy-2-pentanone, 4-methyl-1-phenyl-2-hydroxy-3-pentanone, 1-(4-hydroxyphenyl)pentane, 1-(4-hydroxyphenyl)-1-pentene, 1-(4-hydroxyphenyl)-2-pentene, 1-(4-hydroxyphenyl)-3-pentene, 1-(4-hydroxyphenyl)-2-pentanol, 1-(4-hydroxyphenyl)-3-pentanol, 1-(4-hydroxyphenyl)-2-pentanone, 1-(4-hydroxyphenyl)-3-pentanone, 1-(4-hydroxyphenyl)-2,3-pentanediol, 1-(4-hydroxyphenyl)-2-hydroxy-3-pentanone, 1-(4-hydroxyphenyl)-3-hydroxy-2-pentanone, 1-(4-hydroxyphenyl)-2,3-pentanedione, 4-methyl-1-(4-hydroxyphenyl)pentane, 4-methyl-1-(4-hydroxyphenyl)-2-pentene, 4-methyl-1-(4-hydroxyphenyl)-3-pentene, 4-methyl-1-(4-hydroxyphenyl)-1-pentene, 4-methyl-1-(4- hydroxyphenyl)-3-pentanol, 4-methyl-1-(4-hydroxyphenyl)-2-pentanol, 4-methyl-1-(4-hydroxyphenyl)-3-pentanone, 4-methyl-1-(4-hydroxyphenyl)-2-pentanone, 4-methyl-1-(4-hydroxyphenyl)-2,3-pentanediol, 4-methyl-1-(4-hydroxyphenyl)-2,3-pentanedione, 4-methyl-1-(4-hydroxyphenyl)-3-hydroxy-2-pentanone, 4-methyl-1-(4-hydroxyphenyl)-2-hydroxy-3-pentanone, 1-indole-3-pentane, 1-(indole-3)-1-pentene, 1-(indole-3)-2-pentene, 1-(indole-3)-3-pentene, 1-(indole-3)-2-pentanol, 1-(indole-3)-3-pentanol, 1-(indole-3)-2-pentanone, 1-(indole-3)-3-pentanone, 1-(indole-3)-2,3-pentanediol, 1-(indole-3)-2-hydroxy-3-pentanone, 1-(indole-3)-3-hydroxy-2-pentanone, 1-(indole-3)-2,3-pentanedione, 4-methyl-1-(indole-3-)pentane, 4-methyl-1-(indole-3)-2-pentene, 4-methyl-1-(indole-3)-3-pentene, 4-methyl-1-(indole-3)-1-pentene, 4-methyl-2-(indole-3)-3-pentanol, 4-methyl-1-(indole-3)-2-pentanol, 4-methyl-1-(indole-3)-3-pentanone, 4-methyl-1-(indole-3)-2-pentanone, 4-methyl-1-(indole-3)-2,3-pentanediol, 4-methyl-1-(indole-3)-2,3-pentanedione, 4-methyl-1-(indole-3)-3-hydroxy-2-pentanone, 4-methyl-1-(indole-3)-2-hydroxy-3-pentanone, n-hexane, 1-hexene, 1-hexanol, hexanal, hexanoate, 2-hexene, 3-hexene, 2-hexanol, 3-hexanol, 2-hexanone, 3-hexanone, 2,3-hexanediol, 2,3-hexanedione, 3,4-hexanediol, 3,4-hexanedione, 2-hydroxy-3-hexanone, 3-hydroxy-2-hexanone, 3-hydroxy-4-hexanone, 4-hydroxy-3-hexanone, 2-methylhexane, 3-methylhexane, 2-methyl-2-hexene, 2-methyl-3-hexene, 5-methyl-1-hexene, 5-methyl-2-hexene, 4-methyl-1-hexene, 4-methyl-2-hexene, 3-methyl-3-hexene, 3-methyl-2-hexene, 3-methyl-1-hexene, 2-methyl-3-hexanol, 5-methyl-2-hexanol, 5-methyl-3-hexanol, 2-methyl-3-hexanone, 5-methyl-2-hexanone, 5-methyl-3-hexanone, 2-methyl-3,4-hexanediol, 2-methyl-3,4-hexanedione, 5-methyl-2,3-hexanediol, 5-methyl-2,3-hexanedione, 4-methyl-2,3-hexanediol, 4-methyl-2,3-hexanedione, 2-methyl-3-hydroxy-4-hexanone, 2-methyl-4-hydroxy-3-hexanone, 5-methyl-2-hydroxy-3-hexanone, 5-methyl-3-hydroxy-2-hexanone, 4-methyl-2-hydroxy-3-hexanone, 4-methyl-3-hydroxy-2-hexanone, 2,5-dimethylhexane, 2,5-dimethyl-2-hexene, 2,5-dimethyl-3-hexene, 2,5-dimethyl-3-hexanol, 2,5-dimethyl-3-hexanone, 2,5-dimethyl-3,4-hexanediol, 2,5-dimethyl-3,4-hexanedione, 2,5-dimethyl-3-hydroxy-4-hexanone, 5-methyl-1-phenylhexane, 4-methyl-1-phenylhexane, 5-methyl-1-phenyl-1-hexene, 5-methyl-1-phenyl-2-hexene, 5-methyl-1-phenyl-3-hexene, 4-methyl-1-phenyl-1-hexene, 4-methyl-1-phenyl-2-hexene, 4-methyl-1-phenyl-3-hexene, 5-methyl-1-phenyl-2-hexanol, 5-methyl-1-phenyl-3-hexanol, 4-methyl-1-phenyl-2-hexanol, 4-methyl-1-phenyl-3-hexanol, 5-methyl-1-phenyl-2-hexanone, 5-methyl-1-phenyl-3-hexanone, 4-methyl-1-phenyl-2-hexanone, 4-methyl-1-phenyl-3-hexanone, 5-methyl-1-phenyl-2,3-hexanediol, 4-methyl-1-phenyl-2,3-hexanediol, 5-methyl-1-phenyl-3-hydroxy-2-hexanone, 5-methyl-1-phenyl-2-hydroxy-3-hexanone, 4-methyl-1-phenyl-3-hydroxy-2-hexanone, 4-methyl-1-phenyl-2-hydroxy-3-hexanone, 5-methyl-1-phenyl-2,3-hexanedione, 4-methyl-1-phenyl-2,3-hexanedione, 4-methyl-1-(4-hydroxyphenyl)hexane, 5-methyl-1-(4-hydroxyphenyl)-1-hexene, 5-methyl-1-(4-hydroxyphenyl)-2-hexene, 5-methyl-1-(4-hydroxyphenyl)-3-hexene, 4-methyl-1-(4-hydroxyphenyl)-1-hexene, 4-methyl-1-(4-hydroxyphenyl)-2-hexene, 4-methyl-1-(4-hydroxyphenyl)-3-hexene, 5-methyl-1-(4-hydroxyphenyl)-2-hexanol, 5-methyl-1-(4-hydroxyphenyl)-3-hexanol, 4-methyl-1-(4-hydroxyphenyl)-2-hexanol, 4-methyl-1-(4-hydroxyphenyl)-3-hexanol, 5-methyl-1-(4-hydroxyphenyl)-2-hexanone, 5-methyl-1-(4-hydroxyphenyl)-3-hexanone, 4-methyl-1-(4-hydroxyphenyl)-2-hexanone, 4-methyl-1-(4-hydroxyphenyl)-3-hexanone, 5-methyl-1-(4-hydroxyphenyl)-2,3-hexanediol, 4-methyl-1-(4-hydroxyphenyl)-2,3-hexanediol, 5-methyl-1-(4-hydroxyphenyl)-3-hydroxy-2-hexanone, 5-methyl-1-(4-hydroxyphenyl)-2-hydroxy-3-hexanone, 4-methyl-1-(4-hydroxyphenyl)-3-hydroxy-2-hexanone, 4-methyl-1-(4-hydroxyphenyl)-2-hydroxy-3-hexanone, 5-methyl-1-(4-hydroxyphenyl)-2,3-hexanedione, 4-methyl-1-(4-hydroxyphenyl)-2,3-hexanedione, 4-methyl-1-(indole-3-)hexane, 5-methyl-1-(indole-3)-1-hexene, 5-methyl-1-(indole-3)-2-hexene, 5-methyl-1-(indole-3)-3-hexene, 4-methyl-1-(indole-3)-1-hexene, 4-methyl-1-(indole-3)-2-hexene, 4-methyl-1-(indole-3)-3-hexene, 5-methyl-1-(indole-3)-2-hexanol, 5-methyl-1-(indole-3)-3-hexanol, 4-methyl-1-(indole-3)-2-hexanol, 4-methyl-1-(indole-3)-3-hexanol, 5-methyl-1-(indole-3)-2-hexanone, 5-methyl-1-(indole-3)-3-hexanone, 4-methyl-1-(indole-3)-2-hexanone, 4-methyl-1-(indole-3)-3-hexanone, 5-methyl-1-(indole-3)-2,3-hexanediol, 4-methyl-1-(indole-3)-2,3-hexanediol, 5-methyl-1-(indole-3)-3-hydroxy-2-hexanone, 5-methyl-1-(indole-3)-2-hydroxy-3-hexanone, 4-methyl-1-(indole-3)-3-hydroxy-2-hexanone, 4-methyl-1-(indole-3)-2-hydroxy-3-hexanone, 5-methyl-1-(indole-3)-2,3-hexanedione, 4-methyl-1-(indole-3)-2,3-hexanedione, n-heptane, 1-heptene, 1-heptanol, heptanal, heptanoate, 2-heptene, 3-heptene, 2-heptanol, 3-heptanol, 4-heptanol, 2-heptanone, 3-heptanone, 4-heptanone, 2,3-heptanediol, 2,3-heptanedione, 3,4-heptanediol, 3,4-heptanedione, 2-hydroxy-3-heptanone, 3-hydroxy-2-heptanone, 3-hydroxy-4-heptanone, 4-hydroxy-3-heptanone, 2-methylheptane, 3-methylheptane, 6-methyl-2-heptene, 6-methyl-3-heptene, 2-methyl-3-heptene, 2-methyl-2-heptene, 5-methyl-2-heptene, 5-methyl-3-heptene, 3-methyl-3-heptene, 2-methyl-3-heptanol, 2-methyl-4-heptanol, 6-methyl-3-heptanol, 5-methyl-3-heptanol, 3-methyl-4-heptanol, 2-methyl-3-heptanone, 2-methyl-4-heptanone, 6-methyl-3-heptanone, 5-methyl-3-heptanone, 3-methyl-4-heptanone, 2-methyl-3,4-heptanediol, 2-methyl-3,4-heptanedione, 6-methyl-3,4-heptanediol, 6-methyl-3,4-heptanedione, 5-methyl-3,4-heptanediol, 5-methyl-3,4-heptanedione, 2-methyl-3-hydroxy-4-heptanone, 2-methyl-4-hydroxy-3-heptanone, 6-methyl-3-hydroxy-4-heptanone, 6-methyl-4-hydroxy-3-heptanone, 5-methyl-3-hydroxy-4-heptanone, 5-methyl-4-hydroxy-3-heptanone, 2,6-dimethylheptane, 2,5-dimethylheptane, 2,6-dimethyl-2-heptene, 2,6-dimethyl-3-heptene, 2,5-dimethyl-2-heptene, 2,5-dimethyl-3-heptene, 3,6-dimethyl-3-heptene, 2,6-dimethyl-3-heptanol, 2,6-dimethyl-4-heptanol, 2,5-dimethyl-3-heptanol, 2,5-dimethyl-4-heptanol, 2,6-dimethyl-3,4-heptanediol, 2,6-dimethyl-3,4-heptanedione, 2,5-dimethyl-3,4-heptanediol, 2,5-dimethyl-3,4-heptanedione, 2,6-dimethyl-3-hydroxy-4-heptanone, 2,6-dimethyl-4-hydroxy-3-heptanone, 2,5-dimethyl-3-hydroxy-4-heptanone, 2,5-dimethyl-4-hydroxy-3-heptanone, n-octane, 1-octene, 2-octene, 1-octanol, octanal, octanoate, 3-octene, 4-octene, 4-octanol, 4-octanone, 4,5-octanediol, 4,5-octanedione, 4-hydroxy-5-octanone, 2-methyloctane, 2-methyl-3-octene, 2-methyl-4-octene, 7-methyl-3-octene, 3-methyl-3-octene, 3-methyl-4-octene, 6-methyl-3-octene, 2-methyl-4-octanol, 7-methyl-4-octanol, 3-methyl-4-octanol, 6-methyl-4-octanol, 2-methyl-4-octanone, 7-methyl-4-octanone, 3-methyl-4-octanone, 6-methyl-4-octanone, 2-methyl-4,5-octanediol, 2-methyl-4,5-octanedione, 3-methyl-4,5-octanediol, 3-methyl-4,5-octanedione, 2-methyl-4-hydroxy-5-octanone, 2-methyl-5-hydroxy-4-octanone, 3-methyl-4-hydroxy-5-octanone, 3-methyl-5-hydroxy-4-octanone, 2,7-dimethyloctane, 2,7-dimethyl-3-octene, 2,7-dimethyl-4-octene, 2,7-dimethyl-4-octanol, 2,7-dimethyl-4-octanone, 2,7-dimethyl-4,5-octanediol, 2,7-dimethyl-4,5-octanedione, 2,7-dimethyl-4-hydroxy-5-octanone, 2,6-dimethyloctane, 2,6-dimethyl-3- octene, 2,6-dimethyl-4-octene, 3,7-dimethyl-3-octene, 2,6-dimethyl-4-octanol, 3,7-dimethyl-4-octanol, 2,6-dimethyl-4-octanone, 3,7-dimethyl-4-octanone, 2,6-dimethyl-4,5-octanediol, 2,6-dimethyl-4,5-octanedione, 2,6-dimethyl-4-hydroxy-5-octanone, 2,6-dimethyl-5-hydroxy-4-octanone, 3,6-dimethyloctane, 3,6-dimethyl-3-octene, 3,6-dimethyl-4-octene, 3,6-dimethyl-4-octanol, 3,6-dimethyl-4-octanone, 3,6-dimethyl-4,5-octanediol, 3,6-dimethyl-4,5-octanedione, 3,6-dimethyl-4-hydroxy-5-octanone, n-nonane, 1-nonene, 1-nonanol, nonanal, nonanoate, 2-methylnonane, 2-methyl-4-nonene, 2-methyl-5-nonene, 8-methyl-4-nonene, 2-methyl-5-nonanol, 8-methyl-4-nonanol, 2-methyl-5-nonanone, 8-methyl-4-nonanone, 8-methyl-4,5-nonanediol, 8-methyl-4,5-nonanedione, 8-methyl-4-hydroxy-5-nonanone, 8-methyl-5-hydroxy-4-nonanone, 2,8-dimethylnonane, 2,8-dimethyl-3-nonene, 2,8-dimethyl-4-nonene, 2,8-dimethyl-5-nonene, 2,8-dimethyl-4-nonanol, 2,8-dimethyl-5-nonanol, 2,8-dimethyl-4-nonanone, 2,8-dimethyl-5-nonanone, 2,8-dimethyl-4,5-nonanediol, 2,8-dimethyl-4,5-nonanedione, 2,8-dimethyl-4-hydroxy-5-nonanone, 2,8-dimethyl-5-hydroxy-4-nonanone, 2,7-dimethylnonane, 3,8-dimethyl-3-nonene, 3,8-dimethyl-4-nonene, 3,8-dimethyl-5-nonene, 3,8-dimethyl-4-nonanol, 3,8-dimethyl-5-nonanol, 3,8-dimethyl-4-nonanone, 3,8-dimethyl-5-nonanone, 3,8-dimethyl-4,5-nonanediol, 3,8-dimethyl-4,5-nonanedione, 3,8-dimethyl-4-hydroxy-5-nonanone, 3,8-dimethyl-5-hydroxy-4-nonanone, n-decane, 1-decene, 1-decanol, decanoate, 2,9-dimethyldecane, 2,9-dimethyl-3-decene, 2,9-dimethyl-4-decene, 2,9-dimethyl-5-decanol, 2,9-dimethyl-5-decanone, 2,9-dimethyl-5,6-decanediol, 2,9-dimethyl-6-hydroxy-5-decanone, 2,9-dimethyl-5,6-decanedionen-undecane, 1-undecene, 1-undecanol, undecanal, undecanoate, n-dodecane, 1-dodecene, 1-dodecanol, dodecanal, dodecanoate, n-dodecane, 1-decadecene, n-tridecane, 1-tridecene, 1-tridecanol, tridecanal, tridecanoate, n-tetradecane, 1-tetradecene, 1-tetradecanol, tetradecanal, tetradecanoate, n-pentadecane, 1-pentadecene, 1-pentadecanol, pentadecanal, pentadecanoate, n-hexadecane, 1-hexadecene, 1-hexadecanol, hexadecanal, hexadecanoate, n-heptadecane, 1-heptadecene, 1-heptadecanol, heptadecanal, heptadecanoate, n-octadecane, 1-octadecene, 1-octadecanol, octadecanal, octadecanoate, n-nonadecane, 1-nonadecene, 1-nonadecanol, nonadecanal, nonadecanoate, eicosane, 1-eicosene, 1-eicosanol, eicosanal, eicosanoate, 3-hydroxy propanal, 1,3-propanediol, 4-hydroxybutanal, 1,4-butanediol, 3-hydroxy-2-butanone, 2,3-butandiol, 1,5-pentane diol, homocitrate, homoisocitorate, b-hydroxy adipate, glutarate, glutarsemialdehyde, glutaraldehyde, 2-hydroxy-1-cyclopentanone, 1,2-cyclopentanediol, cyclopentanone, cyclopentanol, (S)-2-acetolactate, (R)-2,3-Dihydroxy-isovalerate, 2-oxoisovalerate, isobutyryl-CoA, isobutyrate, isobutyraldehyde, 5-amino pentaldehyde, 1,10-diaminodecane, 1,10-diamino-5-decene, 1,10-diamino-5-hydroxydecane, 1,10-diamino-5-decanone, 1,10-diamino-5,6-decanediol, 1,10-diamino-6-hydroxy-5-decanone, phenylacetoaldehyde, 1,4-diphenylbutane, 1,4-diphenyl-1-butene, 1,4-diphenyl-2-butene, 1,4-diphenyl-2-butanol, 1,4-diphenyl-2-butanone, 1,4-diphenyl-2,3-butanediol, 1,4-diphenyl-3-hydroxy-2-butanone, 1-(4-hydeoxyphenyl)-4-phenylbutane, 1-(4-hydeoxyphenyl)-4-phenyl-1-butene, 1-(4-hydeoxyphenyl)-4-phenyl-2-butene, 1-(4-hydeoxyphenyl)-4-phenyl-2-butanol, 1-(4-hydeoxyphenyl)-4-phenyl-2-butanone, 1-(4-hydeoxyphenyl)-4-phenyl-2,3-butanediol, 1-(4-hydeoxyphenyl)-4-phenyl-3-hydroxy-2-butanone, 1-(indole-3)-4-phenylbutane, 1-(indole-3)-4-phenyl-1-butene, 1-(indole-3)-4-phenyl-2-butene, 1-(indole-3)-4-phenyl-2-butanol, 1-(indole-3)-4-phenyl-2-butanone, 1-(indole-3)-4-phenyl-2,3-butanediol, 1-(indole-3)-4-phenyl-3-hydroxy-2-butanone, 4-hydroxyphenylacetoaldehyde, 1,4-di(4-hydroxyphenyl)butane, 1,4-di(4-hydroxyphenyl)-1-butene, 1,4-di(4-hydroxyphenyl)-2-butene, 1,4-di(4-hydroxyphenyl)-2-butanol, 1,4-di(4-hydroxyphenyl)-2-butanone, 1,4-di(4-hydroxyphenyl)-2,3-butanediol, 1,4-di(4-hydroxyphenyl)-3-hydroxy-2-butanone, 1-(4-hydroxyphenyl)-4-(indole-3-)butane, 1-(4-hydroxyphenyl)-4-(indole-3)-1-butene, 1-di(4-hydroxyphenyl)-4-(indole-3)-2-butene, 1-(4-hydroxyphenyl)-4-(indole-3)-2-butanol, 1-(4-hydroxyphenyl)-4-(indole-3)-2-butanone, 1-(4-hydroxyphenyl)-4-(indole-3)-2,3-butanediol, 1-(4-hydroxyphenyl-4-(indole-3)-3-hydroxy-2-butanone, indole-3-acetoaldehyde, 1,4-di(indole-3-) butane, 1,4-di(indole-3)-1-butene, 1,4-di(indole-3)-2-butene, 1,4-di(indole-3)-2-butanol, 1,4-di(indole-3)-2-butanone, 1,4-di(indole-3)-2,3-butanediol, 1,4-di(indole-3)-3-hydroxy-2-butanone, succinate semialdehyde, hexane-1,8-dicarboxylic acid, 3-hexene-1,8-dicarboxylic acid, 3-hydroxy-hexane-1,8-dicarboxylic acid, 3-hexanone-1,8-dicarboxylic acid, 3,4-hexanediol-1,8-dicarboxylic acid, 4-hydroxy-3-hexanone-1,8-dicarboxylic acid, glycerol, fucoidan, iodine, chlorophyll, carotenoid, calcium, magnesium, iron, sodium, potassium, phosphate, lactic acid, acetic acid, formic acid, isoprenoids, and polyisoprenes, including rubber. Further, such products can include succinic acid, pyruvic acid, enzymes such as cellulases, polysaccharases, lipases, proteases, ligninases, and hemicellulases and may be present as a pure compound, a mixture, or an impure or diluted form.

The term "fatty acid comprising material" as used herein has its ordinary meaning as known to those skilled in the art and can comprise one or more chemical compounds that include one or more fatty acid moieties as well as derivatives of these compounds and materials that comprise one or more of these compounds. Common examples of compounds that include one or more fatty acid moieties include triacylglycerides, diacylglycerides, monoacylglycerides, phospholipids, lysophospholipids, free fatty acids, fatty acid salts, soaps, fatty acid comprising amides, esters of fatty acids and monohydric alcohols, esters of fatty acids and polyhydric alcohols including glycols (e.g. ethylene glycol, propylene glycol, etc.), esters of fatty acids and polyethylene glycol, esters of fatty acids and polyethers, esters of fatty acids and polyglycol, esters of fatty acids and saccharides, esters of fatty acids with other hydroxyl-containing compounds, etc. A fatty acid comprising material can be one or more of these compounds in an isolated or purified form. It can be a material that includes one or more of these compounds that is combined or blended with other similar or different materials. It can be a material where the fatty acid comprising material occurs with or is provided with other similar or different materials, such as vegetable and animal oils; mixtures of vegetable and animal oils; vegetable and animal oil byproducts; mixtures of vegetable and animal oil byproducts; vegetable and animal wax esters; mixtures, derivatives and byproducts of vegetable and animal wax esters; seeds; processed seeds; seed byproducts; nuts; processed nuts; nut byproducts; animal matter; processed animal matter; byproducts of animal matter; corn; processed corn; corn byproducts; distiller's grains; beans; processed beans; bean byproducts; soy products; lipid containing plant, fish or animal matter; processed lipid containing plant or animal matter; byproducts of lipid containing plant, fish or animal matter; lipid containing microbial material; processed lipid containing microbial material; and byproducts of lipid containing microbial matter. Such materials can be utilized in liquid or solid forms. Solid forms include whole forms, such as cells, beans, and seeds; ground, chopped, slurried, extracted, flaked, milled, etc. The fatty acid portion of the fatty acid comprising compound can be a simple fatty acid, such as one that includes a carboxyl group attached to a substituted or un-substituted alkyl group. The substituted or unsubstituted alkyl group can be straight or branched, saturated or unsaturated. Substitutions on the alkyl group can include hydroxyls, phosphates, halogens, alkoxy, or aryl groups. The substituted or unsubstituted alkyl group can have 7 to 29 carbons and preferably 11 to 23 carbons (e.g., 8 to 30 carbons and preferably 12 to 24 carbons counting the carboxyl group) arranged in a linear chain with or without side chains and/or substitutions. Addition of the fatty acid comprising compound can be by way of adding a material comprising the fatty acid comprising compound.

The term "pH modifier" as used herein has its ordinary meaning as known to those skilled in the art and can include any material that will tend to increase, decrease or hold steady the pH of the broth or medium. A pH modifier can be an acid, a base, a buffer, or a material that reacts with other materials present to serve to raise, lower, or hold steady the pH. In one embodiment, more than one pH modifier can be used, such as more than one acid, more than one base, one or more acid with one or more bases, one or more acids with one or more buffers, one or more bases with one or more buffers, or one or more acids with one or more bases with one or more buffers. In one embodiment, a buffer can be produced in the broth or medium or separately and used as an ingredient by at least partially reacting in acid or base with a base or an acid, respectively. When more than one pH modifiers are utilized, they can be added at the same time or at different times. In one embodiment, one or more acids and one or more bases are combined, resulting in a buffer. In one embodiment, media components, such as a carbon source or a nitrogen source serve as a pH modifier; suitable media components include those with high or low pH or those with buffering capacity. Exemplary media components include acid- or base-hydrolyzed plant polysaccharides having residual acid or base, ammonia fiber explosion (AFEX) treated plant material with residual ammonia, lactic acid, corn steep solids or liquor.

The term "fermentation" as used herein has its ordinary meaning as known to those skilled in the art and can include culturing of a microorganism or group of microorganisms in or on a suitable medium for the microorganisms. The microorganisms can be aerobes, anaerobes, facultative anaerobes, heterotrophs, autotrophs, photoautotrophs, photoheterotrophs, chemoautotrophs, and/or chemoheterotrophs. The microorganisms can be growing aerobically or anaerobically. They can be in any phase of growth, including lag (or conduction), exponential, transition, stationary, death, dormant, vegetative, sporulating, etc.

"Growth phase" is used herein to describe the type of cellular growth that occurs after the "Initiation phase" and before the "Stationary phase" and the "Death phase." The growth phase is sometimes referred to as the exponential phase or log phase or logarithmic phase.

The term "plant polysaccharide" as used herein has its ordinary meaning as known to those skilled in the art and can comprise one or more polymers of saccharides and saccharide derivatives as well as derivatives of saccharide polymers and/or other polymeric materials that occur in plant matter. Exemplary plant polysaccharides include lignin, cellulose, starch, pectin, and hemicellulose. Others are chitin, sulfonated polysaccharides such as alginic acid, agarose, carrageenan, porphyran, furcelleran and funoran. Generally, the polysaccharide can have two or more saccharide units or derivatives of saccharide units. The saccharide units and/or derivatives of saccharide units can repeat in a regular pattern, or otherwise. The saccharide units can be hexose units or pentose units, or combinations of these. The derivatives of saccharide units can be sugar alcohols, sugar acids, amino sugars, etc. The polysaccharides can be linear, branched, cross-linked, or a mixture thereof. One type or class of polysaccharide can be cross-linked to another type or class of polysaccharide.

The term "fermentable saccharides" as used herein has its ordinary meaning as known to those skilled in the art and can include one or more saccharides and/or saccharide derivatives that can be utilized as a carbon source by the microorganism, including monomers, dimers, and polymers of these compounds including two or more of these compounds. In some cases, the organism can break down these polymers, such as by hydrolysis, prior to incorporating the broken down material. Exemplary fermentable saccharides include, but are not limited to glucose, dextrose, xylose, arabinose, galactose, mannose, rhamnose, cellobiose, lactose, sucrose, maltose, and fructose.

The term "saccharification" as used herein has its ordinary meaning as known to those skilled in the art and can include conversion of plant polysaccharides to lower molecular weight species that can be utilized by the organism at hand. For some organisms, this would include conversion to monosaccharides, disaccharides, trisaccharides, and oligosaccharides of up to about seven monomer units, as well as similar sized chains of saccharide derivatives and combinations of saccharides and saccharide derivatives. The terms "SSF" and "SHF" are known to those skilled in the art; SSF meaning simultaneous saccharification and fermentation, or the conversion from polysaccharides or oligosaccharides into monosaccharides at the same time and in the same fermentation vessel wherein monosaccharides are converted to another chemical product such as ethanol. "SHF" indicates a physical separation of the polymer hydrolysis or saccharification and fermentation processes.

The term "biomass" as used herein has its ordinary meaning as known to those skilled in the art and can include one or more biological materials that can be converted into a biofuel, chemical or other product. Biomass as used herein is synonymous with the term "feedstock" and includes corn syrup, molasses, silage, agricultural residues (corn stalks, grass, straw, grain hulls, bagasse, etc.), animal waste (manure from cattle, poultry, and hogs), Distillers Dried Solubles (DDS), Distillers Dried Grains (DDG), Condensed Distillers Solubles (CDS), Distillers Wet Grains (DWG), Distillers Dried Grains with Solubles (DDGS), woody materials (wood or bark, sawdust, timber slash, and mill scrap), municipal waste (waste paper, recycled toilet papers, yard clippings, etc.), and energy crops (poplars, willows, Eucalyptus, switchgrass, alfalfa, prairie bluestem, algae, including macroalgae, etc.). One exemplary source of biomass is plant matter. Plant matter can be, for example, woody plant matter, non-woody plant matter, cellulosic material, lignocellulosic material, hemicellulosic material, carbohydrates, pectin, starch, inulin, fructans, glucans, corn, sugar cane, grasses, switchgrass, sorghum, high biomass sorghum, bamboo, algae and material derived from these. Plants can be in their natural state or genetically modified, e.g., to increase the cellulosic or hemicellulosic portion of the cell wall, or to produce additional exogenous or endogenous enzymes to increase the separation of cell wall components. Plant matter can be further described by reference to the chemical species present, such as proteins, polysaccharides and oils. Polysaccharides include polymers of various monosaccharides and derivatives of monosaccharides including glucose, fructose, lactose, galacturonic acid, rhamnose, etc. Plant matter also includes agricultural waste byproducts or side streams such as pomace, corn steep liquor, corn steep solids, distillers grains, peels, pits, fermentation waste, straw, lumber, sewage, garbage and food leftovers. Peels can be citrus which include, but are not limited to, tangerine peel, grapefruit peel, orange peel, tangerine peel, lime peel and lemon peel. These materials can come from farms, forestry, industrial sources, households, etc. Another non-limiting example of biomass is animal matter, including, for example milk, meat, fat, animal processing waste, and animal waste. Biomass can include cell or tissue cultures; for example, biomass can include plant cell culture(s) or plant tissue culture(s). "Feedstock" is frequently used to refer to biomass being used for a process, such as those described herein.

"Broth" is used herein to refer to inoculated medium at any stage of growth, including the point immediately after inoculation and the period after any or all cellular activity has ceased and can include the material after post-fermentation processing. It includes the entire contents of the combination of soluble and insoluble matter, suspended matter, cells and medium, as appropriate.

The term "productivity" as used herein has its ordinary meaning as known to those skilled in the art and can include the mass of a material of interest produced in a given time in a given volume. Units can be, for example, grams per liter-hour, or some other combination of mass, volume, and time. In fermentation, productivity is frequently used to characterize how fast a product can be made within a given fermentation volume. The volume can be referenced to the total volume of the fermentation vessel, the working volume of the fermentation vessel, or the actual volume of broth being fermented. The context of the phrase will indicate the meaning intended to one of skill in the art. Productivity is different from "titer" in that productivity includes a time term, and titer is analogous to concentration. Titer and Productivity can generally be measured at any time during the fermentation, such as at the beginning, the end, or at some intermediate time, with titer relating the amount of a particular material present or produced at the point in time of interest and the productivity relating the amount of a particular material produced per liter in a given amount of time. The amount of time used in the productivity determination can be from the beginning of the fermentation or from some other time, and go to the end of the fermentation, such as when no additional material is produced or when harvest occurs, or some other time as indicated by the context of the use of the term. "Overall productivity" refers to the productivity determined by utilizing the final titer and the overall fermentation time.

"Titer" refers to the amount of a particular material present in a fermentation broth. It is similar to concentration and can refer to the amount of material made by the organism in the broth from all fermentation cycles, or the amount of material made in the current fermentation cycle or over a given period of time, or the amount of material present from whatever source, such as produced by the organism or added to the broth. Frequently, the titer of soluble species will be referenced to the liquid portion of the broth, with insolubles removed, and the titer of insoluble species will be referenced to the total amount of broth with insoluble species being present, however, the titer of soluble species can be referenced to the total broth volume and the titer of insoluble species can be referenced to the liquid portion, with the context indicating the which system is used with both reference systems intended in some cases. Frequently, the value determined referenced to one system will be the same or a sufficient approximation of the value referenced to the other.

"Concentration" when referring to material in the broth generally refers to the amount of a material present from all sources, whether made by the organism or added to the broth. Concentration can refer to soluble species or insoluble species, and is referenced to either the liquid portion of the broth or the total volume of the broth, as for "titer."

The term "biocatalyst" as used herein has its ordinary meaning as known to those skilled in the art and can include one or more enzymes and/or microorganisms, including solutions, suspensions, and mixtures of enzymes and microorganisms. In some contexts this word will refer to the possible use of either enzymes or microorganisms to serve a particular function, in other contexts the word will refer to the combined use of the two, and in other contexts the word will refer to only one of the two. The context of the phrase will indicate the meaning intended to one of skill in the art.

The terms "conversion efficiency" or "yield" as used herein have their ordinary meaning as known to those skilled in the art and can include the mass of product made from a mass of substrate. The term can be expressed as a percentage yield of the product from a starting mass of substrate. For the production of C5 and C6 saccharides (e.g., monosaccharides, e.g., glucose, xylose, arabinose, etc.), the yield is based upon the actual weight of the saccharides released compared to the weight of the oligosaccharides (e.g., cellulose, hemicellulose) in the input biomass. For the production of ethanol from glucose, the net reaction is generally accepted as:

$$C_6—H_{12}O_6 \rightarrow 2C_2H_5OH+2CO_2$$

and the theoretical maximum conversion efficiency, or yield, is 51% (wt.). Frequently, the conversion efficiency will be referenced to the theoretical maximum, for example, "80% of the theoretical maximum." In the case of conversion of glucose to ethanol, this statement would indicate a conversion efficiency of 41% (wt.). The context of the phrase will indicate the substrate and product intended to one of skill in the art.

For substrates (e.g., a biomass composition) comprising a mixture of different carbon sources (e.g., xylan, xylose, glucose, cellobiose, arabinose, cellulose, hemicellulose, etc.), the theoretical maximum conversion efficiency of the biomass to saccharides or ethanol can be calculated as an average of the maximum yields or conversion efficiencies of the individual carbon source constituents weighted by the relative concentration of each carbon source. In some cases, the theoretical maximum conversion efficiency can be calculated based on an assumed saccharification efficiency. By way of example only, given a carbon source comprising 10 g of cellulose, the theoretical maximum conversion efficiency can be calculated by assuming saccharification of the cellulose to the assimilable carbon source (glucose) of about 75% by weight. In this example, 10 g of cellulose can provide 7.5 g of glucose which can provide a maximum theoretical conversion efficiency of about 7.5 g*51% or 3.8 g of ethanol. In other cases, the efficiency of the saccharification step can be calculated or determined based upon a measurement of the sugars content of an input biomass, e.g., following hydrolysis with 72% sulfuric acid. See A Sluiter, et al., Determination of Structural Carbohydrates and Lignin in Biomass (NREL, revised June 2010), which is hereby incorporated by reference in its entirety. Saccharification efficiencies anticipated by the present invention include about 10%, 20%, 30%, 40%, 50%, 60%, 70%, 80%, 90%, 95%, 99% or about 100% for any carbohydrate carbon sources larger than a single monosaccharide subunit.

"Pretreatment" or "pretreated" is used herein to refer to any mechanical, chemical, thermal, biochemical process or combination of these processes whether in a combined step or performed sequentially, that achieves disruption or expansion of the biomass so as to render the biomass more susceptible to attack by enzymes and/or microbes. In one embodiment, pretreatment includes removal or disruption of lignin so as to make the cellulose and hemicellulose polymers in the plant biomass more available to cellulolytic and/or hemicellulolytic enzymes and/or microbes, for example, by treatment with acid or base. In one embodiment, pretreatment includes disruption or expansion of cellulosic and/or hemicellulosic material. Steam explosion, and ammonia fiber expansion (or explosion) (AFEX) are well known thermal/chemical techniques. Hydrolysis, including methods that utilize acids, bases, and/or enzymes can be used. Other thermal, chemical, biochemical, enzymatic techniques can also be used.

"Fed-batch" or "fed-batch fermentation" is used herein to include methods of culturing microorganisms where nutrients, other medium components, or biocatalysts (including, for example, enzymes, fresh organisms, extracellular broth, genetically modified plants and/or organisms, etc.) are supplied to the fermentor during cultivation, but culture broth is not harvested from the fermentor until the end of the fermentation, although it can also include "self seeding" or "partial harvest" techniques where a portion of the fermentor volume is harvested and then fresh medium is added to the remaining broth in the fermentor, with at least a portion of the inoculum being the broth that was left in the fermentor. During a fed-batch fermentation, the broth volume can increase, at least for a period, by adding medium or nutrients to the broth while fermentation organisms are present. Suitable nutrients which can be utilized include those that are soluble, insoluble, and partially soluble, including gasses, liquids and solids. In one embodiment, a fed-batch process is referred to with a phrase such as, "fed-batch with cell augmentation." This phrase can include an operation where nutrients and cells are added or one where cells with no substantial amount of nutrients are added. The more general phrase "fed-batch" encompasses these operations as well. The context where any of these phrases is used will indicate to one of skill in the art the techniques being considered.

"Saccharide compounds" or "saccharide streams" is used herein to indicate mostly monosaccharide saccharides, dissolved, crystallized, evaporated, or partially dissolved, including but not limited to hexoses and pentoses; sugar alcohols; sugar acids; sugar amines; compounds containing two or more of these linked together directly or indirectly through covalent or ionic bonds; and mixtures thereof. Included within this description are disaccharides; trisaccharides; oligosaccharides; polysaccharides; and saccharide chains, branched and/or linear, of any length. A saccharide stream can consist of primarily or substantially C6 saccharides, C5 saccharides, or mixtures of both C6 and C5 saccharides in varying ratios of said saccharides. C6 saccharides have a six-carbon molecular backbone and C5 saccharides have a five-carbon molecular backbone.

DESCRIPTION

The following description and examples illustrate some exemplary embodiments of the disclosure in detail. Those of skill in the art will recognize that there are numerous variations and modifications of this disclosure that are encompassed by its scope. Accordingly, the description of a certain exemplary embodiment should not be deemed to limit the scope of the present disclosure.

Introduction

Many of the methods used to make the hemicellulose and cellulose of biomass more accessible can generate inhibitor compounds that can negatively affect downstream processing, such as saccharification and/or fermentation. There is a need for pretreatment process that provides a biomass fraction that is accessible to effective enzymatic hydrolysis without the formation or release of large volumes of inhibitors.

Some methods used in pretreating biomass utilize high temperatures, pressure and/or steam without a highly satisfactory result to extract most or all the carbohydrate in biomass. Alkali pretreatment can be used, but can be costly because of the high volume of water that may be necessary to rinse the biomass. Acid hydrolysis can be used to extract and reduce the hemicellulose and cellulose to C5 and C6 saccharides. Because the process uses acid, process equipment such as pumps and pipes must be corrosion resistant and can be more expensive than those used to process grains. This process can also generate neutralization byproducts, such as calcium sulfate or gypsum, which may need to be isolated and disposed of. The processes described can also produce inhibitors that can be difficult to remove and can negatively affect the fermentation process.

Methods of pretreating biomass to avoid acid processing have also been investigated. For example, U.S. Pat. No. 5,846,787 discloses a process in which cellulose-containing material is pretreated by combining the material with water in a reactor and heating the resultant combination to a temperature of 160° C. to 220° C. while maintaining the pH at 5 to 8. The resultant material may then be hydrolyzed using enzymes. This process, however, only works on herbaceous materials and biomass that has been preprocessed (municipal sewage waste, recycled materials, etc.) It may not work well on a woody biomass. Furthermore, the above methods only result in process slurries that must be significantly diluted to be manageable. And, prior acid and steam explosion processes may be limited to 8% to 15% by weight solids based on the total weight of the slurry.

The processes describe above are designed to make the carbohydrate polymers accessible to enzymatic hydrolysis to produce monomers, whether the addition of enzymes is separate from downstream fermentation to biofuels and chemical products, or whether simultaneous saccharification and fermentation through isolated enzyme addition and/or microbial enzymatic action in the conversion of polymers to end product. Further, the enzyme loads necessary to hydrolyze such imperfectly processed materials can be high and therefore costly. Despite high enzyme loads, inhibitors released during pretreatment can interfere with enzymatic hydrolysis and simultaneous or subsequent fermentation.

Biomass and Pretreatment of Biomass Compositions

Disclosed herein are methods of producing compositions comprising C5 and/or C6 saccharides from a biomass composition comprising cellulose, hemicellulose, and/or lignocellulose. The methods can comprise pretreatment of the biomass composition and/or enzymatic hydrolysis of the pretreated biomass. Pretreatment of the biomass composition can reduce solid particle size. Reducing the size of biomass solids can increase the efficiency of other processing steps such as chemical treatment, thermal treatment, enzymatic treatment. Increased efficiency can mean that less time is required in another processing step. Increased efficiency can mean that a higher yield of a desirable product such as C5 and/or C6 saccharides is produced in another processing step. Increased efficiency can mean that fewer inhibitors are produced in another processing step.

Biomass can be derived from agricultural crops, crop residues, trees, woodchips, sawdust, paper, cardboard, grasses, algae, municipal waste and other sources as described supra. In one embodiment, the biomass contains cellulosic, hemicellulosic, and/or lignocellulosic material. In one embodiment the biomass is woody (poplar, Eucalyptus, willow, pine, etc.). In another embodiment, the biomass is non-woody plant material, such as grasses, dicots, monocots, etc. Other biomasses include algal biomass, nonvascular plant biomass, and processed materials derived from plants; e.g., hulls, distiller's grains, municipal sewage waste, and the like.

In one embodiment, a biomass composition comprising cellulose, hemicellulose, and/or lignocellulose comprises alfalfa, algae, bagasse, bamboo, corn stover, corn cobs, corn kernels, corn mash, corn steep liquor, corn steep solids, distiller's grains, distiller's dried solubles, distiller's dried grains, condensed distiller's solubles, distiller's wet grains, distiller's dried grains with solubles, eucalyptus, food waste, fruit peels, garden residue, grass, grain hulls, modified crop plants, municipal waste, oat hulls, paper, paper pulp, prairie bluestem, poplar, rice hulls, seed hulls, silage, sorghum, straw, sugarcane, switchgrass, wheat, wheat straw, wheat bran, de-starched wheat bran, willows, wood, plant cells, plant tissue cultures, tissue cultures, or a combination thereof.

Cellulose can be a linear polymer of glucose where the glucose units are connected via $\beta(1\rightarrow4)$ linkages. Hemicellulose can be a branched polymer of a number of saccharide monomers including glucose, xylose, mannose, galactose, rhamnose and arabinose, and can have sugar acids such as mannuronic acid and galacturonic acid present as well. Lignin can be a cross-linked, racemic macromolecule of p-coumaryl alcohol, conferyl alcohol and sinapyl alcohol. These three polymers can occur together in lignocellulosic materials in biomass. The different characteristics of the three polymers can make hydrolysis of the combination difficult as each polymer tends to shield the others from enzymatic attack.

Prior to pretreatment of a biomass composition, some processing can occur. For example, debris, such as soil, inert matter (rocks, pebbles) and other non-biological material can be removed by sifting or sorting in some manner. The biomass composition can be cleaned by washing with water or other chemicals. The biomass composition can be dried. The biomass composition can be mechanically processed (e.g., coarse chopped or ground) to reduce the size of any solids prior to pretreatment. The amount of mechanical processing prior to pretreatment can depend upon the biomass. For example, woody materials can be chipped, cut, milled, ground prior or otherwise reduced in size prior to pretreatment. In one embodiment, woody materials are reduced in size to about a cm or less prior to pretreatment. In another embodiment, woody materials are reduced to less than 0.5 cm prior to pretreatment. In another example, agricultural residues (e.g., corn stover, wheat, straw, etc.) can be cut, chopped, shredded, or otherwise reduced in size prior to pretreatment. In one embodiment, agricultural residues are reduced in size to less than 10 cm in length prior to pretreatment. In another embodiment, agricultural residues are reduced in size to less than 5 cm in length prior to pretreatment.

See, e.g., U.S. Pat. No. 5,865,898, U.S. Pat. No. 8,110,383, U.S. Pat. No. 7,932,063, or U.S. Pat. No. 7,503,981, which are hereby incorporated by reference in their entireties.

In some embodiments, the preferred biomass particle size to be suspended varies depending on a number of factors, including: the composition of the biomass material, the composition of the liquid hydrocarbon material, the velocity of the liquid hydrocarbon material, the temperature and pressure of the suspension, the material of the conduit (e.g. pipe or tank), holding the suspension, the amount of time the suspension is to remain together and the like considerations. In one embodiment, the suspension of the biomass material and liquid hydrocarbon material is contained within a pipe at a refinery and the biomass material may be considered efficiently carried by the liquid hydrocarbon material so long as the pipe does not substantially plug after continued use.

Consumers of saccharide streams produced from biomass have a variety of needs regarding the purity and concentration of the saccharides. In general, the more reduced the inhibitor concentration, the more fermentable the saccharides. Purified saccharides can be used to produce concentrated, clean end-products of fermentation such as succinic acid which is used as a precursor for plastic manufacture. To satisfy a wide range of consumers of saccharides, the amount of C5 and C6 saccharides that go into each batch for distribution must be controlled. The ability to solubilize nearly all C5 saccharides in the pretreatment, is the only way to separate the streams efficiently. A pretreatment that results in a fine, homogeneous particle size allows solubilization of over 85% of the available hemicellulose prior to enzymatic hydrolyzation. This reduces the evaporation needed to achieve a concentrated C5 stream and, therefore reduces the phenolics and other inhibitors present in the system making the C5 stream more fermentable than what could be achieved by poor solubilization of hemicellulose during pretreatment. When the particle size is reduced, the cooking of the material during pretreatment is much more uniform. With heterogeneous material, some particles are undercooked and some are overcooked. As the particle size becomes more homogenous, cooking can be optimized across the entire system. This even heating prevents charring of the material that can lead to significant losses in saccharides and higher production of inhibitors. Uniform heat throughout the biomass also prevents undercooking which can lead to unhydrolyzed cellulose during enzyme hydrolysis.

Pretreating a biomass composition can comprise mechanical, thermal, pressure, chemical, thermochemical, and/or biochemical processes. These processes can be performed individually or in combination. Pretreatment of the biomass composition can be performed such that any solids are reduced in size. Reducing the size of solids in the biomass composition can be advantageous because smaller particles have larger surface area to volume ratios. Increasing the ratio of surface area to volume can be advantageous because it can, for example, increase the rate of particle wetting (e.g., with water or a chemical agent such as an acid or a base), increase the accessibility of enzymes to the polysaccharides in the biomass, enable the use of a smaller dose of enzymes during a hydrolysis of the biomass, enable the use of fewer or lower amounts of chemicals (e.g., acids or bases) during a pretreatment and/or hydrolysis step, enable the use of weaker acids or bases in a pretreatment or hydrolysis step, enable the use of higher concentrations of solids in any further processing step (e.g., during a hydrolysis step), and/or increase the yield of saccharides from the hydrolysis of the biomass.

Biomass compositions can be reduced in size to a mixture of particles having a uniform, or substantially uniform, size. Such mixtures can be referred to as homogeneous mixtures. Homogeneous mixtures of particles can have many advantages over mixtures of particles having heterogeneous sizes with respect to further pretreatment processes and/or during hydrolysis to produce saccharide streams. For example, heterogeneous mixtures of particles can experience uneven heating during thermal and thermochemical processing steps. Uneven heating can lead to overcooking (e.g., charring/burning) of particles and/or undercooking of particles. Charring or burning of particles can reduce the yield of saccharide from the hydrolysis of the particles; this can be due to degradation or denaturation of saccharide polymers such as starch, hemicellulose, and/or cellulose. Undercooking of particles can lead to unhydrolyzed saccharide polymers (e.g., starch, hemicellulose, cellulose) during enzymatic or chemical hydrolysis, which can also reduce the yield of saccharide. In contrast, uniform heating, wetting, chemical treatment (e.g., acid or base treatment), and/or enzyme hydrolysis can be achieved with mixtures of particles having uniform sizes (e.g., homogeneous mixtures).

In one embodiment, methods are provided for the pretreatment of biomass used in the production of saccharide streams and/or production of fermentation end-products such as biofuels and chemicals.

In one embodiment, methods are provided for the pretreatment of feedstock used in the fermentation and production of the biofuels and chemicals. The pretreatment steps can include mechanical, thermal, pressure, chemical, thermochemical, and/or biochemical tests pretreatment prior to being used in a bioprocess for the production of fuels and chemicals, but untreated biomass material can be used in the process as well. Mechanical processes can reduce the particle size of the biomass material so that it can be more conveniently handled in the bioprocess and can increase the surface area of the feedstock to facilitate contact with chemicals/biochemicals/biocatalysts. Mechanical processes can also separate one type of biomass material from another. The biomass material can also be subjected to thermal and/or chemical pretreatments to render plant polymers more accessible. Multiple steps of treatment can also be used. Mechanical processes include, are not limited to, washing, soaking, milling, size reduction, screening, shearing, chopping, pressurization, and the like, as well as size classification and density classification processes. Any process can be used that reduces the size of the feedstock to a homogeneous mixture of particles of less than 10 mm, 7.5 mm, 5 mm, 2.5 mm, 2 mm, 1.5 mm, or 1 mm in size (e.g., diameter or length). One such method is to use a vortex generator and cutting system such as that found in U.S. Patent Applications Nos. 2002192774A1, 2012037325A1, and 2011275860A1.

In one embodiment, biomass is conveyed into a vortex mixer outfitted with blades. Water with or without one or more acids, bases, or other chemicals (e.g., dilute sulfuric acid) is dispersed with these solids in a mix of 5% solids to 95% water at about 50° C. The vortex is intended to pull the materials through while the pH is adjusted and temperature maintained. The material is deposited in a second chamber where dewatering takes place until the feedstock is a plug. The feedstock plug then goes through other blades with microholes. Steam is added to maintain heat and pressure and the plug is subjected to even 160° C. to 180° C. temperatures and thorough cooking and mixing for a period of time as it is pushed through a pipe. At the end of the pipe, the material is subjected to steam explosion and is collected into a bin where water is added to a desired solid to liquid ratio.

Chemical pretreatment processes include, but are not limited to, bleaching, oxidation, reduction, acid treatment, base treatment, sulfite treatment, acid sulfite treatment, basic sulfite treatment, ammonia treatment, and hydrolysis. Thermal pretreatment processes include, but are not limited to, sterilization, ammonia fiber expansion or explosion ("AFEX"), steam explosion, holding at elevated temperatures, pressurized or unpressurized, in the presence or absence of water, and freezing. Biochemical processes include, but are not limited to, treatment with enzymes, including enzymes produced by genetically-modified plants, and treatment with microorganisms. Various enzymes that can be utilized include cellulase, amylase, β-glucosidase, xylanase, gluconase, and other polysaccharases; lysozyme; laccase, and other lignin-modifying enzymes; lipoxygenase, peroxidase, and other oxidative enzymes; proteases; and lipases. One or more of the mechanical, chemical, thermal, thermochemical, and biochemical processes can be combined or used separately. Such combined processes can also include those used in the production of paper, cellulose products, microcrystalline cellulose, and cellulosics and can include pulping, kraft pulping, acidic sulfite processing. The feedstock can be a side stream or waste stream from a facility that utilizes one or more of these processes on a biomass material, such as cellulosic, hemicellulosic or lignocellulosic material. Examples include paper plants, cellulosics plants, distillation plants, cotton processing plants, and microcrystalline cellulose plants. The feedstock can also include cellulose-containing or cellulosic containing waste materials. The feedstock can also be biomass materials, such as wood, grasses, corn, starch, or saccharide, produced or harvested as an intended feedstock for production of ethanol or other products such as by biocatalysts.

In another embodiment, a method can utilize a pretreatment process disclosed in U.S. Patents and Patent Applications US20040152881, US20040171136, US20040168960, US20080121359, US20060069244, US20060188980, US20080176301, U.S. Pat. No. 5,693,296, U.S. Pat. No. 6,262,313, US20060024801, U.S. Pat. No. 5,969,189, U.S. Pat. No. 6,043,392, US20020038058, U.S. Pat. No. 5,865,898, U.S. Pat. No. 5,865,898, U.S. Pat. No. 6,478,965, U.S. Pat. No. 5,986,133, or US20080280338, each of which is incorporated by reference herein in its entirety In another embodiment, the AFEX process is be used for pretreatment of biomass. The AFEX process can be used in the preparation of cellulosic, hemicellulosic or lignocellulosic materials for fermentation to ethanol or other products. The process generally includes combining the feedstock with ammonia, heating under pressure, and suddenly releasing the pressure. Water can be present in various amounts. The AFEX process has been the subject of numerous patents and publications.

In another embodiment, the pretreatment of biomass comprises the addition of calcium hydroxide to a biomass to render the biomass susceptible to degradation. Pretreatment comprises the addition of calcium hydroxide and water to the biomass to form a mixture, and maintaining the mixture at a relatively high temperature. Alternatively, an oxidizing agent, selected from the group consisting of oxygen and oxygen-containing gasses, can be added under pressure to the mixture. Examples of carbon hydroxide treatments are disclosed in U.S. Pat. No. 5,865,898 to Holtzapple and S. Kim and M. T. Holzapple, Bioresource Technology, 96, (2005) 1994, incorporated by reference herein in its entirety.

In one embodiment, pretreatment of biomass comprises dilute acid hydrolysis. Example of dilute acid hydrolysis treatment are disclosed in T. A. Lloyd and C. E Wyman, Bioresource Technology, (2005) 96, 1967), incorporated by reference herein in its entirety.

In another embodiment, pretreatment of biomass comprises pH controlled liquid hot water treatment. Examples of pH controlled liquid hot water treatments are disclosed in N. Mosier et al., Bioresource Technology, (2005) 96, 1986, incorporated by reference herein in its entirety.

In one embodiment, pretreatment of biomass comprises aqueous ammonia recycle process (ARP). Examples of aqueous ammonia recycle process are described in T. H. Kim and Y. Y. Lee, Bioresource Technology, $(2005)_{96}$, 2007, incorporated by reference herein in its entirety.

In one embodiment, the above mentioned methods have two steps: a pretreatment step that leads to a wash stream, and an enzymatic hydrolysis step of pretreated-biomass that produces a hydrolysate stream. In the above methods, the pH at which the pretreatment step is carried out includes acid hydrolysis, hot water pretreatment, steam explosion or alkaline reagent based methods (AFEX, ARP, and lime pretreatments). Dilute acid and hot water treatment methods solubilize mostly hemicellulose, whereas methods employing alkaline reagents remove most lignin during the pretreatment step. As a result, the wash stream from the pretreatment step in the former methods contains mostly hemicellulose-based saccharides, whereas this stream has mostly lignin for the high-pH methods. The subsequent enzymatic hydrolysis of the residual biomass leads to mixed saccharides (C5 and C6) in the alkali based pretreatment methods, while glucose is the major product in the hydrolyzate from the low and neutral pH methods. In one embodiment, the treated material is additionally treated with catalase or another similar chemical, chelating agents, surfactants, and other compounds to remove impurities or toxic chemicals or further release polysaccharides.

In one embodiment, pretreatment of biomass comprises ionic liquid (IL) pretreatment. Biomass can be pretreated by incubation with an ionic liquid, followed by IL extraction with a wash solvent such as alcohol or water. The treated biomass can then be separated from the ionic liquid/wash-solvent solution by centrifugation or filtration, and sent to the saccharification reactor or vessel. Examples of ionic liquid pretreatment are disclosed in US publication No. 2008/0227162, incorporated herein by reference in its entirety.

In another embodiment, a method can utilize a pretreatment process disclosed in U.S. Pat. No. 4,600,590 to Dale, U.S. Pat. No. 4,644,060 to Chou, U.S. Pat. No. 5,037,663 to Dale. U.S. Pat. No. 5,171,592 to Holtzapple, et al., U.S. Pat. No. 5,939,544 to Karstens, et al., U.S. Pat. No. 5,473,061 to Bredereck, et al., U.S. Pat. No. 6,416,621 to Karstens., U.S. Pat. No. 6,106,888 to Dale, et al., U.S. Pat. No. 6,176,176 to Dale, et al., PCT publication WO2008/020901 to Dale, et al., Felix, A., et al., Anim Prod. 51, 47-61 (1990), Wais, A. C., Jr., et al., Journal of Animal Science, 35, No. 1, 109-112 (1972), which are incorporated herein by reference in their entireties.

Alteration of the pH of a pretreated feedstock can be accomplished by washing the feedstock (e.g., with water) one or more times to remove an alkaline or acidic substance, or other substance used or produced during pretreatment. Washing can comprise exposing the pretreated feedstock to an equal volume of water 2, 3, 4, 5, 6, 7, 8, 9, 10, 11, 12, 13, 14, 15, 16, 17, 18, 19, 20, 21, 22, 23, 24, 25 or more times. In another embodiment, a pH modifier can be added. For example, an acid, a buffer, or a material that reacts with other materials present can be added to modulate the pH of the feedstock. In one embodiment, more than one pH modifier can be used, such as one or more bases, one or more bases with one or more buffers, one or more acids, one or more acids with one or more buffers, or one or more buffers. When more than one pH modifiers are utilized, they can be added at the same time or at different times. Other non-limiting exemplary methods for neutralizing feedstocks treated with alkaline substances have been described, for example in U.S. Pat. Nos. 4,048,341; 4,182,780; and 5,693,296.

In one embodiment, one or more acids can be combined, resulting in a buffer. Suitable acids and buffers that can be used as pH modifiers include any liquid or gaseous acid that is compatible with the microorganism. Non-limiting examples include peroxyacetic acid, sulfuric acid, lactic acid, citric acid, phosphoric acid, and hydrochloric acid. In some instances, the pH can be lowered to neutral pH or acidic pH, for example a pH of 7.0, 6.5, 6.0, 5.5, 5.0, 4.5, 4.0, or lower. In some embodiments, the pH is lowered and/or maintained within a range of about pH 4.5 to about 7.1, or about 4.5 to about 6.9, or about pH 5.0 to about 6.3, or about pH 5.5 to about 6.3, or about pH 6.0 to about 6.5, or about pH 5.5 to about 6.9 or about pH 6.2 to about 6.7.

In another embodiment, biomass can be pre-treated at an elevated temperature and/or pressure. In one embodiment biomass is pre treated at a temperature range of 20° C. to 400° C. In another embodiment biomass is pretreated at a temperature of about 20° C., 25° C., 30° C., 35° C., 40° C., 45° C., 50° C., 55° C., 60° C., 65° C., 80° C., 90° C., 100° C., 120° C., 150° C., 200° C., 250° C., 300° C., 350° C., 400° C. or higher. In another embodiment, elevated temperatures are provided by the use of steam, hot water, or hot gases. In one embodiment steam can be injected into a biomass containing vessel. In another embodiment the steam, hot water, or hot gas can be injected into a vessel jacket such that it heats, but does not directly contact the biomass.

In another embodiment, a biomass can be treated at an elevated pressure. In one embodiment biomass is pre treated at a pressure range of about 1 psi to about 30 psi. In another embodiment biomass is pre treated at a pressure or about 1 psi, 2 psi, 3 psi, 4 psi, 5 psi, 6 psi, 7 psi, 8 psi, 9 psi, 10 psi, 12 psi, 15 psi, 18 psi, 20 psi, 22 psi, 24 psi, 26 psi, 28 psi, 30 psi or more. In some embodiments, biomass can be treated with elevated pressures by the injection of steam into a biomass containing vessel. In one embodiment, the biomass can be treated to vacuum conditions prior or subsequent to alkaline or acid treatment or any other treatment methods provided herein.

In one embodiment alkaline or acid pretreated biomass is washed (e.g. with water (hot or cold) or other solvent such as alcohol (e.g. ethanol)), pH neutralized with an acid, base, or buffering agent (e.g. phosphate, citrate, borate, or carbonate salt) or dried prior to fermentation. In one embodiment, the drying step can be performed under vacuum to increase the rate of evaporation of water or other solvents. Alternatively, or additionally, the drying step can be performed at elevated temperatures such as about 20° C., 25° C., 30° C., 35° C., 40° C., 45° C., 50° C., 55° C., 60° C., 65° C., 80° C., 90° C., 100° C., 120° C., 150° C., 200° C., 250° C., 300° C. or more.

In one embodiment of the present invention, the pretreatment step includes a step of solids recovery. The solids recovery step can be during or after pretreatment (e.g., acid or alkali pretreatment), or before the drying step. In one embodiment, the solids recovery step provided by the methods of the present invention includes the use of a sieve, filter, screen, or a membrane for separating the liquid and solids fractions. In one embodiment a suitable sieve pore diameter size ranges from about 0.001 microns to 8 mm, such as about 0.005 microns to 3 mm or about 0.01 microns to 1 mm. In one embodiment a sieve pore size has a pore diameter of about 0.01 microns, 0.02 microns, 0.05 microns, 0.1 microns, 0.5 microns, 1 micron, 2 microns, 4 microns, 5 microns, 10 microns, 20 microns, 25 microns, 50 microns, 75 microns, 100 microns, 125 microns, 150 microns, 200 microns, 250 microns, 300 microns, 400 microns, 500 microns, 750 microns, 1 mm or more. In one embodiment, biomass (e.g. corn stover) is processed or pretreated prior to fermentation. In one embodiment a method of pre-treatment includes but is not limited to, biomass particle size reduction, such as for example shredding, milling, chipping, crushing, grinding, or pulverizing. In one embodiment, biomass particle size reduction can include size separation methods such as sieving, or other suitable methods known in the art to separate materials based on size. In one embodiment size separation can provide for enhanced yields. In one embodiment, separation of finely shredded biomass (e.g. particles smaller than about 3 mm in diameter, such as, 3, 2.9, 2.7, 2.5, 2.3, 2, 1.9, 1.7, 1.5, 1.3, 1, 0.9, 0.8, 0.7, 0.6, 0.5, 0.4, 0.3, 0.2, or 0.1 mm) from larger particles allows the recycling of the larger particles back into the size reduction process, thereby increasing the final yield of processed biomass. In one embodiment, a fermentative mixture is provided which comprises a pretreated lignocellulosic feedstock comprising less than about 50% of a lignin component present in the feedstock prior to pretreatment and comprising more than about 60% of a hemicellulose component present in the feedstock prior to pretreatment; and a microorganism capable of fermenting a five-carbon saccharide, such as xylose, arabinose or a combination thereof, and a six-carbon saccharide, such as glucose, galactose, mannose or a combination thereof. In some instances, pretreatment of the lignocellulosic feedstock comprises adding an alkaline substance which raises the pH to an alkaline level, for example NaOH. In one embodiment, NaOH is added at a concentration of about 0.5% to about 2% by weight of the feedstock. In one embodiment, pretreatment also comprises addition of a chelating agent.

Disclosed herein are methods of producing a composition comprising C5 and/or C6 saccharides from a biomass composition comprising cellulose, hemicellulose, and/or lignocellulose. In some embodiments, the methods comprise pretreating the biomass composition to produce a pretreated biomass composition. Pretreating the biomass composition can comprise hydrating the biomass composition, mechanically reducing the size of solids in the biomass composition, heating the biomass composition, or a combination thereof. In some embodiments, the pretreated biomass composition comprises solid particles that are less than 10 mm, 7.5 mm, 5 mm, 2.5 mm, 2 mm, 1.5 mm, or 1 mm in size. In some embodiments, the pretreated biomass composition further comprises a yield of C5 monosaccharides and/or disaccharides that is at least 50% of a theoretical maximum.

In some embodiments, pretreatment of a biomass composition comprises hydration of the biomass composition to produce a hydrated biomass composition. Hydration of the biomass composition can comprise mixing or soaking the biomass composition in an aqueous medium. The aqueous medium can be a non-neutral aqueous medium. The non-neutral aqueous medium can comprise one or more acids or one or more bases. The one or more acids can be sulfuric acid, peroxyacetic acid, lactic acid, formic acid, acetic acid, citric acid, phosphoric acid, hydrochloric acid, sulfurous acid, chloroacetic acid, dichloroacetic acid, trichloroacetic acid, trifluoroacetic acid, oxalic acid, benzoic acid, or a combination thereof. The one or more bases can be sodium hydroxide, calcium hydroxide, potassium hydroxide, ammonia, ammonia hydroxide, hydrogen peroxide or a combination thereof. Hydration of the biomass composition with one or more acids or one or more bases can precondition the biomass composition for thermochemical hydrolysis by impregnating the solids of the biomass composition with the one or more acids or the one or more bases. In some embodiments, the hydrolysis conditions are such that there is no or substantially no hydrolysis of cellulose, hemicellulose, and/or lignocellulose in the biomass composition.

In some embodiments, pretreatment of a biomass composition comprises hydration of the biomass composition in a non-neutral aqueous medium comprises from about 0.1% to about 50% w/w or v/w by dry biomass weight of one or more acids or one or more bases. For example, the non-neutral aqueous medium can comprise about 25-50%, 10-50%, 10-25%, 5-50%, 5-25%, 5-10%, 4-50%, 4-25%, 4-10%, 4-5%, 3-50%, 3-25%, 3-10%, 3-5%, 3-4%, 2-50%, 2-25%, 2-10%, 2-5%, 2-4%, 2-3%, 1-50%, 1-25%, 1-10%, 1-5%, 1-4%, 1-3%, 1-2%, 0.5-50%, 0.5-25%, 0.5-10%, 0.5-5%, 0.5-4%, 0.5-3%, 0.5-2%, 0.5-1%, 0.5-%, 0.1-50%, 0.1-25%, 0.1-10%, 0.1-5%, 0.1-4%, 0.1-3%, 0.1-2%, 0.1-1%, 0.1-0.5%, 50%, 45%, 40%, 35%, 30%, 25%, 24%, 23%, 22%, 21%, 20%, 19%, 18%, 17%, 16%, 15%, 14%, 13%, 12%, 11%, 10%, 9.5%, 9%, 8.5%, 8%, 7.5%, 7%, 6.5%, 6%, 5.5%, 5%, 4.9%, 4.8%, 4.7%, 4.6%, 4.5%, 4.4%, 4.3%, 4.2%, 4.1%, 4%, 3.9%, 3.8%, 3.7%, 3.6%, 3.5%, 3.4%, 3.3%, 3.2%, 3.1%, 3%, 2.9%, 2.8%, 2.7%, 2.6%, 2.5%, 2.4%, 2.3%, 2.2%, 2.1%, 2%, 1.9%, 1.8%, 1.7%, 1.6%, 1.5%, 1.4%, 1.3%, 1.2%, 1.1%, 1%, 0.9%, 0.8%, 0.7%, 0.6%, 0.5%, 0.4%, 0.3%, 0.2%, or 0.1% of the one or more acids or the one or more bases. The one or more acids can be sulfuric acid, peroxyacetic acid, lactic acid, formic acid, acetic acid, citric acid, phosphoric acid, hydrochloric acid, sulfurous acid, chloroacetic acid, dichloroacetic acid, trichloroacetic acid, trifluoroacetic acid, oxalic acid, benzoic acid, or a combination thereof. The one or more bases can be sodium hydroxide, calcium hydroxide, potassium hydroxide, ammonia, ammonia hydroxide, hydrogen peroxide or a combination thereof. In some embodiments, the non-neutral aqueous medium comprises the one or more acids or the one or more bases at from about 0.1% to about 5% v/w by dry biomass weight. In some embodiments, the non-neutral aqueous medium comprises sulfuric acid at from about 0.1% to about 5% v/w by dry biomass weight. In some embodiments, the non-neutral aqueous medium comprises sulfuric acid at about 1.8% v/w by dry biomass weight. In some embodiments, the non-neutral aqueous medium comprises sulfuric acid at about 1% v/w by dry biomass weight.

In some embodiments, pretreatment of the biomass composition comprises hydration of the biomass composition in a non-neutral aqueous medium having a pH that is less than 7. For example, the non-neutral aqueous medium can have a pH that is less than 7, 6.5, 6, 5.5, 5, 4.5, 4, 3.5, 3, 2.5, 2, 1.5, or 1. For example, the non-neutral aqueous medium can have a pH that is about 6.5, 6.4, 6.3, 6.2, 6.1, 6, 5.9, 5.8, 5.7, 5.6, 5.5, 5.4, 5.3, 5.2, 5.1, 5, 4.9, 4.8, 4.7, 4.6, 4.5, 4.4, 4.3, 4.2, 4.1, 4, 3.9, 3.8, 3.7, 3.6, 3.5, 3.4, 3.3, 3.2, 3.1, 3, 2.9, 2.8, 2.7, 2.6, 2.5, 2.4, 2.3, 2.2, 2.1, 2, 1.9, 1.8, 1.7, 1.6, 1.5, 1.4, 1.3, 1.2, 1.1, 1, 0.9, 0.8, 0.7, 0.6, 0.5, 0.4, 0.3, 0.2, 0.1, or lower. The non-neutral aqueous medium having a pH that is less than 7 can comprise one or more acids such as sulfuric acid, peroxyacetic acid, lactic acid, formic acid, acetic acid, citric acid, phosphoric acid, hydrochloric acid, sulfurous acid, chloroacetic acid, dichloroacetic acid, trichloroacetic acid, trifluoroacetic acid, oxalic acid, benzoic acid, or a combination thereof. The one or more acids can be at any suitable concentration, such as any of the concentrations disclosed herein.

In some embodiments, pretreatment of the biomass composition comprises hydration of the biomass composition in a non-neutral aqueous medium having a pH that is greater than 7. For example, the non-neutral aqueous medium can have a pH that is greater than 7, 7.5, 8, 8.5, 9, 9.5, 10, 10.5, 11, 11.5, 12, 12.5, 13, 13.5 or higher. For example, the non-neutral aqueous medium can have a pH that is about 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.1, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4, 12.5, 12.6, 12.7, 12.8, 12.9, 13, 13.1, 13.2, 13.3, 13.4, 13.5, 13.6, 13.7, 13.8, 13.9, or higher. The non-neutral aqueous medium having a pH greater than 7 can comprise one or more bases such as sodium hydroxide, calcium hydroxide, potassium hydroxide, ammonia, ammonia hydroxide, hydrogen peroxide or a combination thereof. The one or more bases can be at any suitable concentration, such as any of the concentrations disclosed herein.

In some embodiments, hydration of a biomass composition in an aqueous medium, such as any of the aqueous media disclosed herein, can be performed at a temperature that is from about 10° C. to about 100° C. For example, the hydration temperature can be about 10-100° C., 20-80° C., 30-70° C., 40-60° C., 10° C., 15° C., 20° C., 25° C., 30° C., 35° C., 40° C., 45° C., 50° C., 55° C., 60° C., 65° C., 70° C., 75° C., 80° C., 85° C., 90° C., 95° C., or 100° C. In one embodiment, the temperature is from about 30° C. to about 70° C. In another embodiment, the temperature is from about 40° C. to about 60° C. In another embodiment, the temperature is about 50° C.

In some embodiments, hydration of a biomass composition in an aqueous medium, such as any of the aqueous media disclosed herein, is for a hydration time of from about 1 minute to about 24 hours. For example, the hydration time can be about 1-24 hr, 1-18 hr, 1-12 hr, 1-6 hr, 6-24 hr, 6-18 hr, 6-12 hr, 12-24 hr, 12-18 hr, 18-24 hr, 1 hr, 2 hr, 3 hr, 4 hr, 5 hr, 6 hr, 7 hr, 8 hr, 9 hr, 10 hr, 11 hr, 12 hr, 13 hr, 14 hr, 15 hr, 16 hr, 17 hr, 18 hr, 19 hr, 20 hr, 21 hr, 22 hr, 23 hr, 24 hr. In another example, the hydration time can be about 1-60 min, 1-45 min, 1-30 min, 1-15 min, 1-10 min, 1-5 min, 5-45 min, 5-30 min, 5-15 min, 5-10 min, 10-30 min, 10-15 min, 1 min, 2 min, 3 min, 4 min, 5 min, 6 min, 7 min, 8 min, 9 min, 10 min, 11 min, 12 min, 13 min, 14 min, 15 min, 16 min, 17 min, 18 min, 19 min, 20 min, 21 min, 22 min, 23 min, 24 min, 25 min, 26 min, 27 min, 28 min, 29 min, 30 min, 31 min, 32 min, 33 min, 34 min, 35 min, 36 min, 37 min, 38 min, 39 min, 40 min, 41 min, 42 min, 43 min, 44 min, 45 min, 46 min, 47 min, 48 min, 49 min, 50 min, 51 min, 52 min, 53 min, 54 min, 55 min, 56 min, 57 min, 58 min, 59 min, or 60 min. In one embodiment, hydration of the biomass composition is for about 1 minute to about 60 minutes. In another embodiment, hydration of the biomass composition is for about 5 minutes to about 30 minutes. In another embodiment, hydration of the biomass is for about 15 minutes to about 20 minutes.

In some embodiments, hydration of a biomass composition in an aqueous medium produces a hydrated biomass composition comprising from about 1% to about 40% solids by dry biomass weight. For example, the hydrated biomass composition can comprise about 1-40%, 1-30%, 1-20%, 1-10%, 1-5%, 1-2.5%, 2.5-20%, 2.5-10%, 2.5-5%, 5-20%, 5-10%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40% solids by dry biomass weight. In some embodiments, the hydrated biomass composition comprises from about 1% to about 20% solids by dry biomass weight. In some embodiments, the hydrated biomass composition comprises about 5% solids by biomass weight.

In some embodiments, a biomass composition is pretreated to produce a pretreated biomass composition, wherein pretreatment comprises mechanical size reduction of solids in the biomass composition. In some embodiments, the biomass composition is a hydrated biomass composition. In some embodiments, the pretreated biomass composition comprises solid particles that are less than 7.5 mm, 5 mm, 2.5 mm, 2 mm, 1.5 mm, 1 mm, or 0.5 mm in size, or less. Mechanical size reduction can comprise cutting, chipping, grinding, milling, shredding, screening, shearing, steam injection, steam explosion, acid-catalyzed steam explosion, ammonia fiber/freeze explosion (AFEX), or a combination thereof. In some embodiments, mechanical size reduction comprises milling that is hammer milling, ball milling, bead milling, pan milling, colloid milling, or a combination thereof. In some embodiments, mechanical size reduction does not comprise milling. In some embodiments, mechanical size reduction comprises simultaneous cutting and steam injection. In some embodiments, mechanical size reduction comprises steam injection, cutting, and steam explosion. In some embodiments, mechanical size reduction comprises simultaneous cutting and steam injection using a rotating cutter with a plurality of cutting blades and a plurality of steam-injection holes. In some embodiments, mechanical size reduction comprises cutting with a first rotating cutter and a second rotating cutter. In some embodiments, the second rotating cutter comprises a plurality of cutting blades and a plurality of steam-injection holes.

In some embodiments, a biomass composition is pretreated to produce a pretreated biomass composition, wherein pretreatment comprises mechanical size reduction of solids in the biomass composition. In some embodiments, the biomass composition is a hydrated biomass composition. In some embodiments, the pretreated biomass composition comprises solid particles that are less than about 10 mm in size (e.g., length, diameter). For example, the pretreated biomass composition can comprise solid particles having a size of less than about 0.01 mm, 0.02 mm, 0.03 mm, 0.04 mm, 0.05 mm, 0.06 mm, 0.07 mm, 0.08 mm, 0.09 mm, 0.1 mm, 0.15 mm, 0.2 mm, 0.25 mm, 0.3 mm, 0.35 mm, 0.4 mm, 0.45 mm, 0.5 mm, 0.55 mm, 0.6 mm, 0.65 mm, 0.7 mm, 0.75 mm, 0.8 mm, 0.85 mm, 0.9 mm, 0.95 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.5 mm, 3 mm, 3.5 mm, 4 mm, 4.5 mm, 5 mm, 6 mm, 7 mm, 8 mm, 9 mm, or 10 mm. In one embodiment, the pretreated biomass composition comprises solid particles that are less than about 7.5 mm in size. In another embodiment, the pretreated biomass composition comprises solid particles that are less than about 5 mm in size. In another embodiment, the pretreated biomass composition comprises solid particles that are less than about 1.5 mm in size. In another embodiment, the pretreated biomass composition comprises solid particles that are less than about 1 mm in size. In one embodiment, all of the solid particles in the pretreated biomass are less than 7.5 mm in size. In another embodiment, all of the solid particles in the pretreated biomass are less than 5 mm in size. In another embodiment, all of the solid particles in the pretreated biomass are less than 2.5 mm in size. In another embodiment, all of the solid particles in the pretreated biomass are less than 2 mm in size. In another embodiment, all of the solid particles in the pretreated biomass are less than 1.5 mm in size. In another embodiment, all of the solid particles in the pretreated biomass are less than 1 mm in size. In some embodiments, the particles in the pretreated biomass composition have uniform or substantially uniform sizes.

In some embodiments, a biomass composition is pretreated to produce a pretreated biomass composition, wherein pretreatment comprises mechanical size reduction of solids in the biomass composition. In some embodiments, the biomass composition is a hydrated biomass composition. In some embodiments, the pretreated biomass composition comprises solid particles having an average size (e.g., diameter or length) of from about 0.01 mm to about 10 mm. For example, the mixture of particles can have an average particle size (e.g., length or diameter) of about 0.01-10 mm, 0.01-7.5 mm, 0.01-5 mm, 0.01-2.5 mm, 0.01-2 mm, 0.01-1.5 mm, 0.01-1 mm, 0.01-0.5 mm, 0.01-0.1 mm, 0.1-10 mm, 0.1-7.5 mm, 0.1-5 mm, 0.1-2.5 mm, 0.1-2 mm, 0.1-1.5 mm, 0.1-1 mm, 0.1-0.5 mm, 0.5-10 mm, 0.5-7.5 mm, 0.5-5 mm, 0.5-2.5 mm, 0.5-2 mm, 0.5-1.5 mm, 0.5-1 mm, 1-10 mm, 1-7.5 mm, 1-5 mm, 1-2.5 mm, 1-2 mm, 1-1.5 mm, 1.5-10 mm, 1.5-7.5 mm, 1.5-5 mm, 1.5-2.5 mm, 1.5-2 mm, 2-10 mm, 2-7.5 mm, 2-5 mm, 2-2.5 mm, 2.5-10 mm, 2.5-7.5 mm, 2.5-5 mm, 5-10 mm, 5-7.5 mm, 7.5-10 mm, 0.01 mm, 0.05 mm, 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.75 mm, 3 mm, 3.25 mm, 3.5 mm, 3.75 mm, 4 mm, 4.25 mm, 4.5 mm, 4.75 mm, 5 mm, 5.25 mm, 5.5 mm, 5.75 mm, 6 mm, 6.25 mm, 6.5 mm, 6.75 mm, 7 mm, 7.25 mm, 7.5 mm, 8 mm, 8.5 mm, 9 mm, 9.5 mm, 10 mm. In one embodiment, the pretreated biomass composition comprises solid particles having an average size of from about 0.1 mm to about 7.5 mm. In another embodiment, the pretreated biomass composition comprises solid particles having an average size of from about 0.1 mm to about 5 mm. In another embodiment, the pretreated biomass composition comprises solid particles having an average size of from about 0.1 mm to about 1.5 mm. In another embodiment, the pretreated biomass composition comprises solid particles having an average size of from about 0.1 mm to about 1 mm. In another embodiment, the pretreated biomass composition comprises solid particles having an average size of from about 0.5 mm to about 1 mm. In some embodiments, the particles in the pretreated biomass composition have uniform or substantially uniform sizes.

In some embodiments, a biomass composition is pretreated to produce a pretreated biomass composition, wherein pretreatment comprises mechanical size reduction of solids in the biomass composition. In some embodiments, the biomass composition is a hydrated biomass composition. In some embodiments, the solid particles in the pretreated biomass composition are homogenous in size or substantially homogenous in size. The solid particles in the pretreated biomass composition can be considered to be homogenous or substantially homogeneous if greater than about 50% of the particles fall within a given size range. For example, the mixture of particles can be considered homogeneous or substantially homogeneous if about 50%, 55%, 60%, 65%, 70%, 75%, 80%, 85%, 90%, 95%, 96%, 97%, 98%, 99%, 99.5%, or 100% of the solid particles falls within a given size range. The given size range can be from about 0.01 mm to about 10 mm; for example, about 0.01-10 mm, 0.01-7.5 mm, 0.01-5 mm, 0.01-2.5 mm, 0.01-2 mm, 0.01-1.5 mm, 0.01-1 mm, 0.01-0.5 mm, 0.01-0.1 mm, 0.1-10 mm, 0.1-7.5 mm, 0.1-5 mm, 0.1-2.5 mm, 0.1-2 mm, 0.1-1.5 mm, 0.1-1 mm, 0.1-0.5 mm, 0.5-10 mm, 0.5-7.5 mm, 0.5-5 mm, 0.5-2.5 mm, 0.5-2 mm, 0.5-1.5 mm, 0.5-1 mm, 1-10 mm, 1-7.5 mm, 1-5 mm, 1-2.5 mm, 1-2 mm, 1-1.5 mm, 1.5-10 mm, 1.5-7.5 mm, 1.5-5 mm, 1.5-2.5 mm, 1.5-2 mm, 2-10 mm, 2-7.5 mm, 2-5 mm, 2-2.5 mm, 2.5-10 mm, 2.5-7.5 mm, 2.5-5 mm, 5-10 mm, 5-7.5 mm, or 7.5-10 mm. In one embodiment, the given size range is from about 0.1 mm to about 7.5 mm. In another embodiment, the given size range is from about 0.1 mm to about 5 mm. In another embodiment, the given size range is from about 0.1 mm to about 2.5 mm. In another embodiment, the given size range is from about 0.1 mm to about 2 mm. In another embodiment, the given size range is from about 0.1 mm to about 1.5 mm. In another embodiment, the given size range is from about 0.1 mm to about 1 mm In some embodiments, a biomass composition is pretreated to produce a pretreated biomass composition, wherein pretreatment comprises mechanical size reduction of solids in the biomass composition. In some embodiments, the biomass composition is a hydrated biomass composition. In one embodiment, a homogeneous mixture of particles is produced during pretreatment of a biomass composition wherein greater than 50% (e.g., about 50%, 55%, 60%, 65%, 70%, 75%, 80%, 85%, 90%, 95%, 96%, 97%, 98%, 99%, 99.5%, or 100%) of the particles in the mixture have a size (e.g., diameter or length) that is from about 0.01 to about 10 mm. In another embodiment, a homogeneous mixture of particles is produced during pretreatment of biomass wherein greater than 50% (e.g., about 50%, 55%, 60%, 65%, 70%, 75%, 80%, 85%, 90%, 95%, 96%, 97%, 98%, 99%, 99.5%, or 100%) of the particles in the mixture have a size (e.g., diameter or length) that is from about 0.1 to about 5 mm. In another embodiment, a homogeneous mixture of particles is produced during pretreatment of biomass wherein greater than 50% (e.g., about 50%, 55%, 60%, 65%, 70%, 75%, 80%, 85%, 90%, 95%, 96%, 97%, 98%, 99%, 99.5%, or 100%) of the particles in the mixture have a size (e.g., diameter or length) that is from about 0.1 to about 1.5 mm. In one embodiment, a homogeneous mixture of particles is produced during pretreatment of biomass wherein greater than 50% (e.g., about 50%, 55%, 60%, 65%, 70%, 75%, 80%, 85%, 90%, 95%, 96%, 97%, 98%, 99%, 99.5%, or 100%) of the particles in the mixture have a size (e.g., diameter or length) that is from about 0.1 mm to about 1 mm Some embodiments, where pretreatment comprises hydration of a biomass composition to product a hydrated biomass composition and mechanical size reduction of the hydrated biomass composition to produce solid particles less than 10 mm, 7.5 mm, 5 mm, 2.5 mm, 2 mm, 1.5 mm, or 1 mm in size, further comprise dewatering the hydrated biomass composition to a solids content of from about 5% to about 40% by dry biomass weight. For example, the solids content can be about 5-40%, 5-35%, 5-30%, 5-25%, 5-20%, 5-15%, 5-10%, 10-40%, 10-35%, 10-30%, 10-25%, 10-20%, 10-15%, 15-40%, 15-35%, 15-30%, 15-25%, 15-20%, 20-40%, 20-35%, 20-30%, 20-25%, 25-40%, 25-35%, 25-30%, 30-40%, 30-35%, 35-40%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40% by dry biomass weight. In one embodiment, the hydrated biomass is dewatered to a solids content of about 30% by dry biomass weight. Dewatering can be performed before, during, and/or after mechanical size reduction. Dewatering can be performed with a filter, a filter press, a centrifuge, or any other suitable apparatus.

In some embodiments, pretreatment of a biomass composition comprises heating the biomass composition. The pretreatment can further comprises hydrating the biomass composition and/or mechanically reducing the size of the solids in the biomass composition. Heating, hydrating, and/or mechanically reducing the size of the biomass composition during pretreatment can be performed in any order. Heating, hydrating, and/or mechanically reducing the size of the biomass composition can be performed sequentially, at the same time, or can partially overlap in time.

In some embodiments, heating the biomass composition hydrolyzes a portion of the hemicellulose of the biomass composition to C5 monosaccharides and disaccharides. In some embodiments, a yield of C5 monosaccharides and/or disaccharides is at least 50% of the theoretical maximum. In some embodiments, the yield of C5 monosaccharides and/or disaccharides is at least 60%, 65%, 70%, 75%, 80%, 85%, or 90% of the theoretical maximum. In some embodiments, the C5 monosaccharides and/or disaccharides are monosaccharides. In some embodiments, the biomass composition is a hydrated biomass composition. In some embodiments, the hydrated composition is impregnated with one or more acids or one or more bases.

In some embodiments, heating a biomass composition does not, or does not substantially hydrolyze the cellulose of the biomass composition. In some embodiments, a yield of glucose after heating the biomass composition is less than 20% of a theoretical maximum. In some embodiments, the yield of glucose is less than 15%, 10%, 5%, 2.5%, or 1% of the theoretical maximum.

In some embodiments, heating the biomass composition (that was optionally hydrated, mechanically reduced in size, and/or dewatered) is performed at a temperature of from about 100° C. to about 250° C. For example, the temperature can be about 100-250° C., 100-200° C., 100-180° C., 100-160° C., 100-140° C., 100-120° C., 120-200° C., 120-180° C., 120-160° C., 120-140° C., 140-180° C., 140-160° C., 160-180° C., 100° C., 110° C., 120° C., 130° C., 140° C., 150° C., 155° C., 160° C., 165° C., 170° C., 175° C., 180° C., 185° C., 190° C., 200° C., 210° C., 220° C., 230° C., 240° C., or 250° C. In one embodiment, heating of the biomass composition is at a temperature of from about 100° C. to about 250° C. In another embodiment, heating of the biomass composition is at a temperature of from about 150° C. to about 200° C. In another embodiment, heating of the biomass composition is at a temperature of from about 160° C. to about 180° C.

In some embodiments, heating the biomass composition (that was optionally hydrated, mechanically reduced in size, and/or dewatered) is performed at a pressure higher than atmospheric. The pressure can be from about 25 PSIG to about 250 PSIG. For example, the pressure can be about 25-250 PSIG, 25-225 PSIG, 25-200 PSIG, 25-175 PSIG, 25-150 PSIG, 25-125 PSIG, 25-100 PSIG, 25-75 PSIG, 25-50 PSIG, 50-225 PSIG, 50-200 PSIG, 50-175 PSIG, 50-150 PSIG, 50-125 PSIG, 50-100 PSIG, 50-75 PSIG, 75-200 PSIG, 75-175 PSIG, 75-150 PSIG, 75-125 PSIG, 75-100 PSIG, 100-175 PSIG, 100-150 PSIG, 100-125 PSIG, 125-150 PSIG, 25 PSIG, 30 PSIG, 35 PSIG, 40 PSIG, 45 PSIG, 50 PSIG, 55 PSIG, 60 PSIG, 65 PSIG, 70 PSIG, 75 PSIG, 80 PSIG, 85 PSIG, 90 PSIG, 95 PSIG, 100 PSIG, 105 PSIG, 110 PSIG, 115 PSIG, 120 PSIG, 125 PSIG, 130 PSIG, 135 PSIG, 140 PSIG, 145 PSIG, 150 PSIG, 155 PSIG, 160 PSIG, 165 PSIG, 170 PSIG, 175 PSIG, 180 PSIG, 185 PSIG, 190 PSIG, 195 PSIG, 200 PSIG, 205 PSIG, 210 PSIG, 215 PSIG, 220 PSIG, 225 PSIG, 230 PSIG, 235 PSIG, 240 PSIG, 245 PSIG, 250 PSIG. In one embodiment, the pressure is from about 25 PSIG to about 250 PSIG. In another embodiment, the pressure is from about 75 PSIG to about 200 PSIG. In another embodiment, the pressure is from about 100 PSIG to about 150 PSIG.

In some embodiments, pretreatment comprises heating a biomass composition (that was optionally hydrated, mechanically reduced in size, and/or dewatered) under any of the conditions disclosed herein for a time sufficient to produce a yield of C5 monosaccharides and/or disaccharides that is at least 50% of a theoretical maximum. The time sufficient to produce the yield of C5 monosaccharides and/or disaccharides can be from about 1 minute to about 120 minutes. For example, the time can be about 1-120 min, 1-90 min, 1-60 min, 1-30 min, 1-15 min, 1-10 min, 1-5 min, 5-60 min, 5-30 min, 5-15 min, 5-10 min, 120 min, 110 min, 100 min, 90 min, 80 min, 70 min, 60 min, 50 min, 45 min, 40 min, 35 min, 30 min, 25 min, 20 min, 19 min, 18 min, 17 min, 16 min, 15 min, 14 min, 13 min, 12 min, 11 min, 10 min, 9 min, 8 min, 7 min, 6 min, 5 min, 4 min, 3 min, 2 min, 1 min. In one embodiment, the time sufficient to produce the yield of C5 monosaccharides and/or disaccharides is from about 1 minute to about 60 minutes. In another embodiment, the time sufficient to produce the yield of C5 monosaccharides and/or disaccharides is from about 5 minutes to about 30 minutes. In another embodiment, the time sufficient to produce the yield of C5 monosaccharides and/or disaccharides is from about 7.5 minutes to about 12.5 minutes.

In some embodiments, the method disclosed herein are for industrial scale production of compositions comprising C5 and C6 saccharides. In one embodiment industrial scale production comprises pretreating greater than 1 metric ton (MT) in 24 hours. In another embodiment, industrial scale production comprises pretreating greater than 20 MT in 24 hours. In another embodiment, industrial scale production comprises pretreating greater than 50 MT in 24 hours. In another embodiment, industrial scale production comprises pretreating greater than 100 MT in 24 hours.

Hydrolysis

Disclosed herein are methods of producing a composition comprising C5 and/or C6 saccharides from a biomass composition comprising cellulose, hemicellulose, and/or lignocellulose. The methods can comprise pretreating the biomass composition according to any of the methods disclosed herein. In some embodiments, the biomass composition is pretreated to produce a pretreated biomass composition, wherein pretreatment comprises mechanical size reduction of solids in the biomass composition. In some embodiments, the pretreated biomass composition comprises solid particles that are less than 7.5 mm, 5 mm, 2.5 mm, 2 mm, 1.5 mm, 1 mm, or 0.5 mm in size, or less. The pretreated biomass composition can further comprise a yield of C5 monosaccharides and/or disaccharides that is at least 50%, 60%, 65%, 70%, 75%, 80%, 85%, or 90% of a theoretical maximum. The methods of producing a composition can further comprise hydrolyzing the biomass composition or pretreated biomass composition with one or more enzymes for a time sufficient to produce the composition comprising C5 and C6 saccharides. The C5 and C6 saccharides can comprise glucose, xylose, mannose, galactose, rhamnose, arabinose, or a combination thereof. The composition comprising C5 and/or C6 saccharides can be an aqueous composition.

In some embodiments, the one or more enzymes comprise one or more cellulase enzymes and optionally one or more hemicellulase enzymes. In one embodiment, the one or more enzymes is a cellulase and hemicellulase complex. In one embodiment, the cellulase and hemicellulase complex is not supplemented with additional hemicellulase enzymes. In some embodiments, the one or more enzymes comprise a commercially available enzyme cocktail (e.g., Accellerase™ 1000, CelluSeb-TL, CelluSeb-TS, Cellic™, Ctec, Cellic™, CTec2, Cellic™, CTec3, STARGEN™, Maxalig™, Spezyme®, Distillase®, G-Zyme®, Fermenzyme®, Fermgen™, GC 212, or Optimash™, etc.).

In some embodiments, the one or more enzymes are at a total level from about 1% to about 20% w/w or v/w by dry biomass weight. In some embodiments, the one or more enzymes are at a total level from about 1% to about 10% w/w or v/w by dry biomass weight. In some embodiments, the one or more enzymes are at a total level from about 1% to about 5% w/w or v/w by dry biomass weight. In some embodiments, the one or more enzymes are at a total level of less than 15% w/w or v/w by dry biomass weight. In some embodiments, the one or more enzymes are at a total level of less than 10% w/w or v/w by dry biomass weight. In some embodiments, the one or more enzymes are at a total level of less than 5% w/w or v/w by dry biomass weight.

In some embodiments, the time sufficient to produce the composition comprising C6 and C5 saccharides is from about 10 hours to about 100 hours. For example, the time can be about 10-100 hr, 10-75 hr, 10-50 hr, 10-20 hr, 20-100 hr, 20-75 hr, 20-50 hr, 50-100 hr, 50-75 hr, 75-100 hr, 10 hr, 11 hr, 12 hr, 13 hr, 14 hr, 15 hr, 16 hr, 17 hr, 18 hr, 19 hr, 20 hr, 21 hr, 22 hr, 23 hr, 24 hr, 25 hr, 30 hr, 35 hr, 40 hr, 45 hr, 50 hr, 55 hr, 60 hr, 65 hr, 70 hr, 75 hr, 80 hr, 85 hr, 90 hr, 95 hr, or 100 hr. In one embodiment, the time sufficient to produce the composition comprising C6 and C5 saccharides is from about 21 hours to about 50 hours.

In one embodiment, the composition comprising C6 and C5 saccharides comprises glucose in a yield that is greater than 55% of a theoretical maximum at 21 hours of hydrolysis. In another embodiment, the composition comprising C6 and C5 saccharides comprises glucose in a yield that is greater than 60% of a theoretical maximum at 21 hours of hydrolysis. In another embodiment, the composition comprising C6 and C5 saccharides comprises glucose in a yield that is greater than 70% of a theoretical maximum at 21 hours of hydrolysis. In another embodiment, the composition comprising C6 and C5 saccharides comprises glucose in a yield that is greater than 80% of a theoretical maximum at 21 hours of hydrolysis. In another embodiment, the composition comprising C6 and C5 saccharides comprises glucose in a yield that is greater than 90% of a theoretical maximum at 21 hours of hydrolysis. In another embodiment, the composition comprising C6 and C5 saccharides comprises glucose in a yield that is greater than 70% of a theoretical maximum at 48 hours of hydrolysis. In another embodiment, the composition comprising C6 and C5 saccharides comprises glucose in a yield that is greater than 80% of a theoretical maximum at 48 hours of hydrolysis. In another embodiment, the composition comprising C6 and C5 saccharides comprises glucose in a yield that is greater than 90% of a theoretical maximum at 48 hours of hydrolysis. In another embodiment, the composition comprising C6 and C5 saccharides comprises glucose in a yield that is greater than 95% of a theoretical maximum at 48 hours of hydrolysis. In another embodiment, the composition comprising C6 and C5 saccharides comprises xylose in a yield that is greater than 60% of a theoretical maximum at 21 hours of hydrolysis. In another embodiment, the composition comprising C6 and C5 saccharides comprises xylose in a yield that is greater than 70% of a theoretical maximum at 21 hours of hydrolysis. In another embodiment, the composition comprising C6 and C5 saccharides comprises xylose in a yield that is greater than 80% of a theoretical maximum at 21 hours of hydrolysis. In another embodiment, the composition comprising C6 and C5 saccharides comprises xylose in a yield that is greater than 90% of a theoretical maximum at 21 hours of hydrolysis.

Some embodiments comprise adjusting the water content and/or the pH of a pretreated biomass prior to hydrolyzing with one or more enzymes.

The water content of a pretreated biomass composition can be adjusted to from about 5% to about 30% solids by dry biomass weight prior to hydrolyzing with one or more enzymes. For example, the water content can be adjusted to about 5-30%, 5-25%, 5-20%, 5-15%, 5-12%, 5-10%, 5-8%, 8-30%, 8-25%, 8-20%, 8-15%, 8-12%, 8-10%, 10-30%, 10-25%, 10-20%, 10-15%, 10-12%, 12-30%, 12-25%, 12-20%, 12-15%, 15-30%, 15-25%, 15-20%, 20-30%, 20-25%, 25-30%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% solids by dry biomass weight. In one embodiment, the water content of the pretreated biomass composition is adjusted to about 5% to about 30% solids by dry biomass weight. In another embodiment, the water content of the pretreated biomass composition is adjusted to about 5% to about 20% solids by dry biomass weight.

The pH of a pretreated biomass composition can be adjusted to from about 3 to about 8 prior to hydrolyzing with one or more enzymes. For example, the pH can be adjusted to about 3-8, 3-7, 3-6, 3-5.5, 3-4.5, 3-4, 4-7, 4-6, 4-5.5, 4-4.5, 4.5-6, 4.5-5.5, 3, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.5, 7, 7.5, or 8. In one embodiment, the pH of the pretreated biomass composition is adjusted to about 4 to about 7. In another embodiment, the pH of the pretreated biomass composition is adjusted to about 4.5 to about 5.5.

Hydrolysis of a pretreated biomass composition with one or more enzymes can be done at a temperature of from about 30° C. to about 70° C. For example, the temperature of hydrolysis can be about 30-70° C., 30-65° C., 30-60° C., 30-55° C., 30-50° C., 30-45° C., 30-40° C., 40-65° C., 40-60° C., 40-55° C., 40-50° C., 40-45° C., 45-60° C., 45-55° C., 45-50° C., 50-60° C., 50-55° C. In one embodiment, the temperature of hydrolysis is from about 45° C. to about 60° C.

In one embodiment, the biomass hydrolyzing unit provides useful advantages for the conversion of biomass to biofuels and chemical products. One advantage of this unit is its ability to produce monomeric saccharides from multiple types of biomass, including mixtures of different biomass materials, and is capable of hydrolyzing polysaccharides and higher molecular weight saccharides to lower molecular weight saccharides. In one embodiment, the hydrolyzing unit utilizes a pretreatment process and a hydrolytic enzyme which facilitates the production of a saccharide stream containing a concentration of a monomeric saccharide or several monomeric saccharides derived from cellulosic and/or hemicellulosic polymers. Examples of biomass material that can be pretreated and hydrolyzed to manufacture saccharide monomers include, but are not limited to, cellulosic, hemicellulosic, lignocellulosic materials; pectins; starches; wood; paper; agricultural products; forest waste; tree waste; tree bark; leaves; grasses; sawgrass; woody plant matter; non-woody plant matter; carbohydrates; starch; inulin; fructans; glucans; corn; sugar cane; sorghum, other grasses; bamboo, algae, and material derived from these materials. This ability to use a very wide range of pretreatment methods and hydrolytic enzymes gives distinct advantages in biomass fermentations. Various pretreatment conditions and enzyme hydrolysis can enhance the extraction of saccharides from biomass, resulting in higher yields, higher productivity, greater product selectivity, and/or greater conversion efficiency.

In one embodiment, the enzyme treatment is used to hydrolyze various higher saccharides (higher molecular weight) present in biomass to lower saccharides (lower molecular weight), such as in preparation for fermentation by biocatalysts such as yeasts to produce ethanol, hydrogen, or other chemicals such as organic acids including succinic acid, formic acid, acetic acid, and lactic acid. These enzymes and/or the hydrolysate can be used in fermentations to produce various products including fuels, and other chemicals.

In one example, the process for converting biomass material into ethanol includes pretreating the biomass material (e.g., "feedstock"), hydrolyzing the pretreated biomass to convert polysaccharides to oligosaccharides, further hydrolyzing the oligosaccharides to monosaccharides, and converting the monosaccharides to biofuels and chemical products. Enzymes such as cellulases, polysaccharases, lipases, proteases, ligninases, and hemicellulases, help produce the monosaccharides can be used in the biosynthesis of fermentation end-products. Biomass material that can be utilized includes woody plant matter, non-woody plant matter, cellulosic material, lignocellulosic material, hemicellulosic material, carbohydrates, pectin, starch, inulin, fructans, glucans, corn, algae, sugarcane, other grasses, switchgrass, bagasse, wheat straw, barley straw, rice straw, corncobs, bamboo, citrus peels, sorghum, high biomass sorghum, seed hulls, and material derived from these. The final product can then be separated and/or purified, as indicated by the properties for the desired final product. In some instances, compounds related to saccharides such as sugar alcohols or sugar acids can be utilized as well.

Chemicals used in the methods of the present invention are readily available and can be purchased from a commercial supplier, such as Sigma-Aldrich. Additionally, commercial enzyme cocktails (e.g. Accellerase™ 1000, CelluSeb-TL, CelluSeb-TS, Celtic™, Ctec, Cellic™, CTec2, CTec3, STARGEN™, Maxalig™, Spezyme®, Distillase®, G-Zyme®, Fermenzyme®, Fermgen™, GC 212, or Optimash™) or any other commercial enzyme cocktail can be purchased from vendors such as Specialty Enzymes & Biochemicals Co., Genencor, or Novozymes. Alternatively, enzyme cocktails can be prepared by growing one or more organisms such as for example a fungi (e.g. a *Trichoderma*, a *Saccharomyces*, a *Pichia*, a White Rot Fungus etc.), a bacteria (e.g. a *Clostridium*, or a coliform bacterium, a *Zymomonas* bacterium, *Sacharophagus degradans* etc.) in a suitable medium and harvesting enzymes produced therefrom. In some embodiments, the harvesting can include one or more steps of purification of enzymes.

In one embodiment, treatment of biomass comprises enzyme hydrolysis. In one embodiment a biomass is treated with an enzyme or a mixture of enzymes, e.g., endoglucanases, exoglucanases, cellobiohydrolases, cellulase, beta-glucosidases, glycoside hydrolases, glycosyltransferases, lyases, esterases and proteins containing carbohydrate-binding modules. In one embodiment, the enzyme or mixture of enzymes is one or more individual enzymes with distinct activities. In another embodiment, the enzyme or mixture of enzymes can be enzyme domains with a particular catalytic activity. For example, an enzyme with multiple activities can have multiple enzyme domains, including for example glycoside hydrolases, glycosyltransferases, lyases and/or esterases catalytic domains.

As used herein, a multi-enzyme product is one that can be obtained from or derived from a microbial, plant, or other source or combination thereof, and will contain enzymes capable of degrading lignocellulosic material. Examples of enzymes comprising the multi-enzyme products of the invention include cellulases (such as cellobiohydrolases, endoglucanase, β-glucosidases, hemicellulases (such as xylanases, including endoxylanases, exoxylanase, and β-xylosidase), ligninases, amylases, α-arabinofuranosidases, α-glucuronidases, α-glucuronidases, arabinases, glucuronidases, proteases, esterases (including ferulic acid esterase and acetylxylan esterase), lipases, glucomannanases, and xyloglugluconases.

In some embodiments, the multi-enzyme product comprises a hemicellulase. Hemicellulose is a complex polymer, and its composition often varies widely from organism to organism, and from one tissue type to another. In general, a main component of hemicellulose is beta-1,4-linked xylose, a five carbon saccharide. However, this xylose is often branched as beta-1,3 linkages, and can be substituted with linkages to arabinose, galactose, mannose, glucuronic acid, or by esterification to acetic acid. Hemicellulose can also contain glucan, which is a general term for beta-linked six carbon saccharides. Those hemicelluloses include xyloglucan, glucomannan, and galactomannan.

The composition, nature of substitution, and degree of branching of hemicellulose is very different in dicotyledonous plants (dicots, e.g., plant whose seeds have two cotyledons or seed leaves such as lima beans, peanuts, almonds, peas, kidney beans) as compared to monocotyledonous plants (monocots; e.g., plants having a single cotyledon or seed leaf such as corn, wheat, rice, grasses, barley). In dicots, hemicellulose is comprised mainly of xyloglucans that are 1,4-beta-linked glucose chains with 1,6-beta-linked xylosyl side chains. In monocots, including most grain crops, the principal components of hemicellulose are heteroxylans. These are primarily comprised of 1,4-beta-linked xylose backbone polymers with 1,3-beta linkages to arabinose, galactose and mannose as well as xylose modified by ester-linked acetic acids. Also present are branched beta glucans comprised of 1,3- and 1,4-beta-linked glucosyl chains. In monocots, cellulose, heteroxylans and beta glucans are present in roughly equal amounts, each comprising about 15-25% of the dry matter of cell walls.

Hemicellulolytic enzymes, e.g. hemicellulases, include includes both exohydrolytic and endohydrolytic enzymes, such as xylanase, β-xylosidase and esterases, which actively cleave hemicellulosic material through hydrolysis. These xylanase and esterase enzymes cleave the xylan and acetyl side chains of xylan and the remaining xylo-oligomers are unsubstituted and can thus be hydrolyzed with xylosidase only. In addition, several less known side activities have been found in enzyme preparations which hydrolyze hemicellulose. While the multi-enzyme product may contain many types of enzymes, mixtures comprising enzymes that increase or enhance saccharide release from biomass are preferred, including hemicellulases. In one embodiment, the hemicellulase is a xylanase, an arabinofuranosidase, an acetyl xylan esterase, a glucuronidase, an endo-galactanase, a mannanase, an endo arabinase, an exo arabinase, an exo-galactanase, a ferulic acid esterase, a galactomannanase, a xyloglucanase, or mixtures of any of these. In particular, the enzymes can include glucoamylase, β-xylosidase and/or β-glucosidase. The enzymes of the multi-enzyme product can be provided by a variety of sources. In one embodiment, the enzymes can be produced by growing microorganisms or plants that produce the enzymes naturally or by virtue of being genetically modified to express the enzyme or enzymes. In another embodiment, at least one enzyme of the multi-enzyme product is commercially available.

In one embodiment, enzymes that degrade polysaccharides are used for the hydrolysis of biomass and can include enzymes that degrade cellulose, namely, cellulases. Examples of some cellulases include endocellulases and exo-cellulases that hydrolyze beta-1,4-glucosidic bonds.

In one embodiment, enzymes that degrade polysaccharides are used for the hydrolysis of biomass and can include enzymes that have the ability to degrade hemicellulose, namely, hemicellulases. Hemicellulose can be a major component of plant biomass and can contain a mixture of pentoses and hexoses, for example, D-xylopyranose, L-arabinofuranose, D-mannopyranose, D-glucopyranose, D-galactopyranose, D-glucopyranosyluronic acid and other saccharides. In one embodiment, enzymes that degrade polysaccharides are used for the hydrolysis of biomass and can include enzymes that have the ability to degrade pectin, namely, pectinases. In plant cell walls, the cross-linked cellulose network can be embedded in a matrix of pectins that can be covalently cross-linked to xyloglucans and certain structural proteins. Pectin can comprise homogalacturonan (HG) or rhamnogalacturonan (RH).

In one embodiment, hydrolysis of biomass includes enzymes that can hydrolyze starch. Enzymes that hydrolyze starch include alpha-amylase, glucoamylase, beta-amylase, exo-alpha-1,4-glucanase, and pullulanase.

In one embodiment, hydrolysis of biomass comprises hydrolases that can include enzymes that hydrolyze chitin. In another embodiment, hydrolases can include enzymes that hydrolyze lichen, namely, lichenase.

In one embodiment, after pretreatment and/or hydrolysis by any of the above methods the feedstock contains cellulose, hemicellulose, soluble oligomers, simple saccharides, lignin, volatiles and ash. The parameters of the hydrolysis can be changed to vary the concentration of the components of the pretreated feedstock. For example, in one embodiment a hydrolysis is chosen so that the concentration of soluble C5 saccharides is high and the concentration of lignin is low after hydrolysis. Examples of parameters of the hydrolysis include temperature, pressure, time, concentration, composition and pH.

In one embodiment, the parameters of the pretreatment and hydrolysis are changed to vary the concentration of the components of the pretreated feedstock such that concentration of the components in the pretreated and hydrolyzed feedstock is optimal for fermentation with a microbe such as a yeast or bacterium microbe.

In one embodiment, the parameters of the pretreatment are changed to encourage the release of the components of a genetically modified feedstock such as enzymes stored within a vacuole to increase or complement the enzymes synthesized by biocatalyst to produce optimal release of the fermentable components during hydrolysis and fermentation.

In one embodiment, the parameters of the pretreatment and hydrolysis are changed such that concentration of accessible cellulose in the pretreated feedstock is 1%, 5%, 10%, 12%, 13%, 14%, 15%, 16%, 17%, 19%, 20%, 30%, 40% or 50%. In one embodiment, the parameters of the pretreatment are changed such that concentration of accessible cellulose in the pretreated feedstock is 5% to 30%. In one embodiment, the parameters of the pretreatment are changed such that concentration of accessible cellulose in the pretreated feedstock is 10% to 20%.

In one embodiment, the parameters of the pretreatment are changed such that concentration of hemicellulose in the pretreated feedstock is 1%, 5%, 10%, 12%, 13%, 14%, 15%, 16%, 17%, 19%, 20%, 21%, 22%, 23%, 24%, 25%, 26%, 27%, 28%, 29%, 30%, 40% or 50%. In one embodiment, the parameters of the pretreatment are changed such that concentration of hemicellulose in the pretreated feedstock is 5% to 40%. In one embodiment, the parameters of the pretreatment are changed such that concentration of hemicellulose in the pretreated feedstock is 10% to 30%.

In one embodiment, the parameters of the pretreatment and hydrolysis are changed such that concentration of soluble oligomers in the pretreated feedstock is 1%, 10%, 15%, 20%, 25%, 30%, 35%, 40%, 45%, 50%, 55%, 60%, 65%, 70%, 75%, 80%, 85%, 90%, 95%, or 99%. Examples of soluble oligomers include, but are not limited to, cellobiose and xylobiose. In one embodiment, the parameters of the pretreatment are changed such that concentration of soluble oligomers in the pretreated feedstock is 30% to 90%. In one embodiment, the parameters of the pretreatment and/or hydrolysis are changed such that concentration of soluble oligomers in the pretreated feedstock is 45% to 80%.

In one embodiment, the parameters of the pretreatment and hydrolysis are changed such that concentration of simple saccharides in the pretreated feedstock is 1%, 5%, 10%, 12%, 13%, 14%, 15%, 16%, 17%, 19%, 20%, 30%, 40% or 50%. In one embodiment, the parameters of the pretreatment and hydrolysis are changed such that concentration of simple saccharides in the pretreated feedstock is 0% to 20%. In one embodiment, the parameters of the pretreatment and hydrolysis are changed such that concentration of simple saccharides in the pretreated feedstock is 0% to 5%. Examples of simple saccharides include, but are not limited to, C5 and C6 monomers and dimers.

In one embodiment, the parameters of the pretreatment are changed such that concentration of lignin in the pretreated and/or hydrolyzed feedstock is 1%, 5%, 10%, 12%, 13%, 14%, 15%, 16%, 17%, 19%, 20%, 30%, 40% or 50%. In one embodiment, the parameters of the pretreatment and/or hydrolysis are changed such that concentration of lignin in the pretreated feedstock is 0% to 20%. In one embodiment, the parameters of the pretreatment and/or hydrolysis are changed such that concentration of lignin in the pretreated feedstock is 0% to 5%. In one embodiment, the parameters of the pretreatment and hydrolysis are changed such that concentration of lignin in the pretreated and/or hydrolyzed feedstock is less than 1% to 2%. In one embodiment, the parameters of the pretreatment and/or hydrolysis are changed such that the concentration of phenolics is minimized In one embodiment, the parameters of the pretreatment and/or hydrolysis are changed such that concentration of furfural and low molecular weight lignin in the pretreated and/or hydrolyzed feedstock is less than 10%, 9%, 8%, 7%, 6%, 5%, 4%, 3%, 2%, or 1%. In one embodiment, the parameters of the pretreatment and/or hydrolysis are changed such that concentration of furfural and low molecular weight lignin in the pretreated and/or hydrolyzed feedstock is less than 1% to 2%.

In one embodiment, the parameters of the pretreatment and/or hydrolysis are changed such that the concentration of simple saccharides is at least 75% to 85%, and the concentration of lignin is 0% to 5% and the concentration of furfural and low molecular weight lignin in the pretreated feedstock is less than 1% to 2%.

In one embodiment, the parameters of the pretreatment and/or hydrolysis are changed to obtain a high concentration of hemicellulose and a low concentration of lignin. In one embodiment, the parameters of the pretreatment and/or hydrolysis are changed to obtain a high concentration of hemicellulose and a low concentration of lignin such that concentration of the components in the pretreated stock is optimal for fermentation with a microbe such as biocatalyst.

In one embodiment, more than one of these steps can occur at any given time. For example, hydrolysis of the pretreated feedstock and hydrolysis of the oligosaccharides can occur simultaneously, and one or more of these can occur simultaneously to the conversion of monosaccharides to a fuel or chemical.

In another embodiment, an enzyme can directly convert the polysaccharide to monosaccharides. In some instances, an enzyme can hydrolyze the polysaccharide to oligosaccharides and the enzyme or another enzyme can hydrolyze the oligosaccharides to monosaccharides.

In another embodiment, the enzymes can be added to the fermentation or they can be produced by microorganisms present in the fermentation. In one embodiment, the microorganism present in the fermentation produces some enzymes. In another embodiment, enzymes are produced separately and added to the fermentation.

For the overall conversion of pretreated biomass to final product to occur at high rates, it is generally necessary for each of the necessary enzymes for each conversion step to be present with sufficiently high activity. If one of these enzymes is missing or is present in insufficient quantities, the production rate of an end product will be reduced. The production rate can also be reduced if the microorganisms responsible for the conversion of monosaccharides to product only slowly take up monosaccharides and/or have only limited capability for translocation of the monosaccharides and intermediates produced during the conversion to end product. Additions of fractions obtained from pretreatment and/or pretreatment and hydrolysis can increase initial or overall growth rates. In another embodiment, oligomers are taken up slowly by a biocatalyst, necessitating an almost complete conversion of polysaccharides and oligomers to monomeric saccharides.

In another embodiment, the enzymes of the method are produced by a biocatalyst, including a range of hydrolytic enzymes suitable for the biomass materials used in the fermentation methods. In one embodiment, a biocatalyst is grown under conditions appropriate to induce and/or promote production of the enzymes needed for the saccharification of the polysaccharide present. The production of these enzymes can occur in a separate vessel, such as a seed fermentation vessel or other fermentation vessel, or in the production fermentation vessel where ethanol production occurs. When the enzymes are produced in a separate vessel, they can, for example, be transferred to the production fermentation vessel along with the cells, or as a relatively cell free solution liquid containing the intercellular medium with the enzymes. When the enzymes are produced in a separate vessel, they can also be dried and/or purified prior to adding them to the hydrolysis or the production fermentation vessel. The conditions appropriate for production of the enzymes are frequently managed by growing the cells in a medium that includes the biomass that the cells will be expected to hydrolyze in subsequent fermentation steps. Additional medium components, such as salt supplements, growth factors, and cofactors including, but not limited to phytate, amino acids, and peptides can also assist in the production of the enzymes utilized by the microorganism in the production of the desired products.

Fermentation

The present disclosure also provides a fermentative mixture comprising: a cellulosic feedstock pre-treated with an alkaline or acid substance and at a temperature of from about 80° C. to about 120° C.; subsequently hydrolyzed with an enzyme mixture, and a microorganism capable of fermenting a five-carbon saccharide and/or a six-carbon saccharide. In one embodiment, the five-carbon saccharide is xylose, arabinose, or a combination thereof. In one embodiment, the six-carbon saccharide is glucose, galactose, mannose, or a combination thereof. In one embodiment, the alkaline substance is NaOH. In some embodiments, NaOH is added at a concentration of about 0.5% to about 2% by weight of the feedstock. In one embodiment, the acid is equal to or less than 2% HCl or $H_2SO_4$. In one embodiment, the microorganism is a *Rhodococcus* strain, a *Clostridium* strain, a *Trichoderma* strain, a *Saccharomyces* strain, a *Zymomonas* strain, or another microorganism suitable for fermentation of biomass. In another embodiment, the fermentation process comprises fermentation of the biomass using a microorganism that is *Clostridium phytofermentans, Clostridium algidixylanolyticum, Clostridium xylanolyticum, Clostridium cellulovorans, Clostridium cellulolyticum, Clostridium thermocellum, Clostridium josui, Clostridium papyrosolvens, Clostridium cellobioparum, Clostridium hungatei, Clostridium cellulosi, Clostridium stercorarium, Clostridium termitidis, Clostridium thermocopriae, Clostridium celerecrescens, Clostridium polysaccharolyticum, Clostridium populeti, Clostridium lentocellum, Clostridium chartatabidum, Clostridium aldrichii, Clostridium herbivorans, Acetivibrio cellulolyticus, Bacteroides cellulosolvens, Caldicellulosiruptor saccharolyticum, Rhodococcus opacus, Ruminococcus albus, Ruminococcus flavefaciens, Fibrobacter succinogenes, Eubacterium cellulosolvens, Butyrivibrio fibrisolvens, Anaerocellum thermophilum, Halocella cellulolytica, Thermoanaerobacterium thermosaccharolyticum, Sacharophagus degradans*, or *Thermoanaerobacterium saccharolyticum*. In still another embodiment, the microorganism is genetically modified to enhance activity of one or more hydrolytic enzymes, such as a genetically-modified *Saccharomyces cerevisiae.*

In one embodiment a wild type or a genetically-improved microorganism can be used for chemical production by fermentation. Methods to produce a genetically-improved strain can include genetic modification, mutagenesis, and adaptive processes, such as directed evolution. For example, yeasts can be genetically-modified to ferment C5 saccharides. Other useful yeasts are species of *Candida, Cryptococcus, Debaryomyces, Deddera, Hanseniaspora, Kluyveromyces, Pichia, Schizosaccharomyces*, and *Zygosaccharomyces. Rhodococcus* strains, such as *Rhodococcus opacus* variants are a source of triacylglycerols and other storage lipids. (See, e.g., Walternann, et al., Microbiology 146:1143-1149 (2000)). Other useful organisms for fermentation include, but are not limited to, yeasts, especially *Saccaromyces* strains and bacteria such as *Clostridium phytofermentans, Thermoanaerobacter ethanolicus, Clostridium thermocellum, Clostridium beijerinickii, Clostridium acetobutylicum, Clostridium tyrobutyricum, Clostridium thermobutyricum, Thermoanaerobacterium saccharolyticum, Thermoanaerobacter thermohydrosulfuricus, Clostridium acetobutylicum, Moorella* ssp., *Carboxydocella* ssp., *Zymomonas mobilis*, recombinant *E. Coli, Klebsiella oxytoca, Rhodococcus opacus* and *Clostridium beijerickii.*

An advantage of yeasts are their ability to grow under conditions that include elevated ethanol concentration, high saccharide concentration, low saccharide concentration, and/or operate under anaerobic conditions. These characteristics, in various combinations, can be used to achieve operation with long or short fermentation cycles and can be used in combination with batch fermentations, fed batch fermentations, self-seeding/partial harvest fermentations, and recycle of cells from the final fermentation as inoculum.

In one embodiment, fed-batch fermentation is performed on the treated biomass to produce a fermentation end-product, such as alcohol, ethanol, organic acid, succinic acid, TAG, or hydrogen. In one embodiment, the fermentation process comprises simultaneous hydrolysis and fermentation (SSF) of the biomass using one or more microorganisms such as a *Rhodococcus* strain, a *Clostridium* strain, a *Trichoderma* strain, a *Saccharomyces* strain, a *Zymomonas* strain, or another microorganism suitable for fermentation of biomass. In another embodiment, the fermentation process comprises simultaneous hydrolysis and fermentation of the biomass using a microorganism that is *Clostridium algidixylanolyticum, Clostridium xylanolyticum, Clostridium cellulovorans, Clostridium cellulolyticum, Clostridium thermocellum, Clostridium josui, Clostridium papyrosolvens, Clostridium cellobioparum, Clostridium hungatei, Clostridium cellulosi, Clostridium stercorarium, Clostridium termitidis, Clostridium thermocopriae, Clostridium celerecrescens, Clostridium polysaccharolyticum, Clostridium populeti, Clostridium lentocellum, Clostridium chartatabidum, Clostridium aldrichii, Clostridium herbivorans, Clostridium phytofermentans, Acetivibrio cellulolyticus, Bacteroides cellulosolvens, Caldicellulosiruptor saccharolyticum, Ruminococcus albus, Ruminococcus flavefaciens, Fibrobacter succinogenes, Eubacterium cellulosolvens, Butyrivibrio fibrisolvens, Anaerocellum thermophilum, Halocella cellu-*

*lolytica, Thermoanaerobacterium thermosaccharolyticum, Sacharophagus degradans*, or *Thermoanaerobacterium saccharolyticum*.

In one embodiment, the fermentation process can include separate hydrolysis and fermentation (SHF) of a biomass with one or more enzymes, such as a xylanases, endo-1,4-beta-xylanases, xylosidases, beta-D-xylosidases, cellulases, hemicellulases, carbohydrases, glucanases, endoglucanases, endo-1,4-beta-glucanases, exoglucanases, glucosidases, beta-D-glucosidases, amylases, cellobiohydrolases, exocellobiohydrolases, phytases, proteases, peroxidase, pectate lyases, galacturonases, or laccases. In one embodiment one or more enzymes used to treat a biomass is thermostable. In another embodiment a biomass is treated with one or more enzymes, such as those provided herein, prior to fermentation. In another embodiment a biomass is treated with one or more enzymes, such as those provided herein, during fermentation. In another embodiment a biomass is treated with one or more enzymes, such as those provided herein, prior to fermentation and during fermentation. In another embodiment an enzyme used for hydrolysis of a biomass is the same as those added during fermentation. In another embodiment an enzyme used for hydrolysis of biomass is different from those added during fermentation.

In some embodiments, fermentation can be performed in an apparatus such as bioreactor, a fermentation vessel, a stirred tank reactor, or a fluidized bed reactor. In one embodiment the treated biomass can be supplemented with suitable chemicals to facilitate robust growth of the one or more fermenting organisms. In one embodiment a useful supplement includes but is not limited to, a source of nitrogen and/or amino acids such as yeast extract, cysteine, or ammonium salts (e.g. nitrate, sulfate, phosphate, etc.); a source of simple carbohydrates such as corn steep liquor, and malt syrup; a source of vitamins such as yeast extract; buffering agents such as salts (including but not limited to citrate salts, phosphate salts, or carbonate salts); or mineral nutrients such as salts of magnesium, calcium, or iron. In some embodiments redox modifiers are added to the fermentation mixture including but not limited to cysteine or mercaptoethanol.

In one embodiment the titer and/or productivity of fermentation end-product production by a microorganism is improved by culturing the microorganism in a medium comprising one or more compounds comprising hexose and/or pentose saccharides. In one embodiment, a process comprises conversion of a starting material (such as a biomass) to a biofuel, such as one or more alcohols. In one embodiment, methods of the invention comprise contacting substrate comprising both hexose (e.g. glucose, cellobiose) and pentose (e.g. xylose, arabinose) saccharides with a microorganism that can hydrolyze C5 and C6 saccharides to produce ethanol. In another embodiment, methods of the invention comprise contacting substrate comprising both hexose (e.g. glucose, cellobiose) and pentose (e.g. xylose, arabinose) saccharides with *R. opacus* to produce TAG.

In some embodiments of the present invention, batch fermentation with a microorganism of a mixture of hexose and pentose saccharides using the methods of the present invention provides uptake rates of about 0.1-8 g/L/h or more of hexose and about 0.1-8 g/L/h or more of pentose (xylose, arabinose, etc.). In some embodiments of the present invention, batch fermentation with a microorganism of a mixture of hexose and pentose saccharides using the methods of the present invention provides uptake rates of about 0.1, 0.2, 0.4, 0.5, 0.6 0.7, 0.8, 1, 2, 3, 4, 5, or 6 g/L/h or more of hexose and about 0.1, 0.2, 0.4, 0.5, 0.6 0.7, 0.8, 1, 2, 3, 4, 5, or 6 g/L/h or more of pentose.

In one embodiment, a method for production of ethanol or another alcohol produces about 10 g/l to 120 gain 40 hours or less. In another embodiment a method for production of ethanol produces about 10 g/l, 11 g/L, 12 g/L, 13 g/L, 14 g/L, 15 g/L, 16 g/L, 17 g/L, 18 g/L, 19 g/L, 20 g/L, 21 g/L, 22 g/L, 23 g/L, 24 g/L, 25 g/L, 26 g/L, 27 g/L, 28 g/L, 29 g/L, 30 g/L, 31 g/L, 32 g/L, 33 g/L, 34 g/L, 35 g/L, 36 g/L, 37 g/L, 38 g/L, 39 g/L, 40 g/L, 41 g/L, 42 g/L, 43 g/L, 44 g/L, 45 g/L, 46 g/L, 47 g/L, 48 g/L, 49 g/L, 50 g/L, 51 g/L, 52 g/L, 53 g/L, 54 g/L, 55 g/L, 56 g/L, 57 g/L, 58 g/L, 59 g/L, 60 g/L, 61 g/L, 62 g/L, 63 g/L, 64 g/L, 65 g/L, 66 g/L, 67 g/L, 68 g/L, 69 g/L, 70 g/L, 71 g/L, 72 g/L, 73 g/L, 74 g/L, 75 g/L, 76 g/L, 77 g/L, 78 g/L, 79 g/L, 80 g/L, 81 g/L, 82 g/L, 83 g/L, 84 g/L, 85 g/L, 86 g/L, 87 g/L, 88 g/L, 89 g/L, 90 g/L, 91 g/L, 92 g/L, 93 g/L, 94 g/L, 95 g/L, 96 g/L, 97 g/L, 98 g/L, 99 g/L, 100 g/L, 110 g/l, 120 g/l, or more alcohol in 40 hours by the fermentation of biomass. In another embodiment, alcohol is produced by a method comprising simultaneous fermentation of hexose and pentose saccharides. In another embodiment, alcohol is produced by a microorganism comprising simultaneous fermentation of hexose and pentose saccharides.

In another embodiment, the level of a medium component is maintained at a desired level by adding additional medium component as the component is consumed or taken up by the organism. Examples of medium components included, but are not limited to, carbon substrate, nitrogen substrate, vitamins, minerals, growth factors, cofactors, and biocatalysts. The medium component can be added continuously or at regular or irregular intervals. In one embodiment, additional medium component is added prior to the complete depletion of the medium component in the medium. In one embodiment, complete depletion can effectively be used, for example to initiate different metabolic pathways, to simplify downstream operations, or for other reasons as well. In one embodiment, the medium component level is allowed to vary by about 10% around a midpoint, in one embodiment, it is allowed to vary by about 30% around a midpoint, and in one embodiment, it is allowed to vary by 60% or more around a midpoint. In one embodiment, the medium component level is maintained by allowing the medium component to be depleted to an appropriate level, followed by increasing the medium component level to another appropriate level. In one embodiment, a medium component, such as vitamin, is added at two different time points during fermentation process. For example, one-half of a total amount of vitamin is added at the beginning of fermentation and the other half is added at midpoint of fermentation.

In another embodiment, the nitrogen level is maintained at a desired level by adding additional nitrogen-containing material as nitrogen is consumed or taken up by the organism. The nitrogen-containing material can be added continuously or at regular or irregular intervals. Useful nitrogen levels include levels of about 5 to about 10 g/L. In one embodiment levels of about Ito about 12 g/L can also be usefully employed. In another embodiment levels, such as about 0.5, 0.1 g/L or even lower, and higher levels, such as about 20, 30 g/L or even higher are used. In another embodiment a useful nitrogen level is about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22 23, 24, 25, 26, 27, 28, 29 or 30 g/L. Nitrogen can be supplied as a simple nitrogen-containing material, such as an ammonium compounds (e.g. ammonium sulfate, ammonium hydroxide, ammonia, ammonium nitrate, or any other compound or mixture containing an ammonium moiety), nitrate or nitrite compounds (e.g. potassium, sodium, ammonium, calcium, or other compound or mixture containing a nitrate or nitrite moiety), or as a more complex nitrogen-containing material, such as amino acids, proteins, hydrolyzed protein, hydrolyzed yeast, yeast extract, dried brewer's yeast, yeast hydrolysates, distillers' grains, soy protein, hydrolyzed soy protein, fermentation products, and processed or corn steep powder or unprocessed protein-rich vegetable or animal matter, including those derived from bean, seeds, soy, legumes, nuts, milk, pig, cattle, mammal, fish, as well as other parts of plants and other types of animals. Nitrogen-containing materials useful in various embodiments also include materials that contain a nitrogen-containing material, including, but not limited to mixtures of a simple or more complex nitrogen-containing material mixed with a carbon source, another nitrogen-containing material, or other nutrients or non-nutrients, and AFEX treated plant matter.

In another embodiment, the carbon level is maintained at a desired level by adding saccharide compounds or material containing saccharide compounds ("saccharide-containing material") as saccharide is consumed or taken up by the organism. The saccharide-containing material can be added continuously or at regular or irregular intervals. In one embodiment, additional saccharide-containing material is added prior to the complete depletion of the saccharide compounds available in the medium. In one embodiment, complete depletion can effectively be used, for example to initiate different metabolic pathways, to simplify downstream operations, or for other reasons as well. In one embodiment, the carbon level (as measured by the grams of saccharide present in the saccharide-containing material per liter of broth) is allowed to vary by about 10% around a midpoint, in one embodiment, it is allowed to vary by about 30% around a midpoint, and in one embodiment, it is allowed to vary by 60% or more around a midpoint. In one embodiment, the carbon level is maintained by allowing the carbon to be depleted to an appropriate level, followed by increasing the carbon level to another appropriate level. In some embodiments, the carbon level can be maintained at a level of about 5 to about 120 g/L. However, levels of about 30 to about 100 g/L can also be usefully employed as well as levels of about 60 to about 80 g/L. In one embodiment, the carbon level is maintained at greater than 25 g/L for a portion of the culturing. In another embodiment, the carbon level is maintained at about 5 g/L, 6 g/L, 7 g/L, 8 g/L, 9 g/L, 10 g/L, 11 g/L, 12 g/L, 13 g/L, 14 g/L, 15 g/L, 16 g/L, 17 g/L, 18 g/L, 19 g/L, 20 g/L, 21 g/L, 22 g/L, 23 g/L, 24 g/L, 25 g/L, 26 g/L, 27 g/L, 28 g/L, 29 g/L, 30 g/L, 31 g/L, 32 g/L, 33 g/L, 34 g/L, 35 g/L, 36 g/L, 37 g/L, 38 g/L, 39 g/L, 40 g/L, 41 g/L, 42 g/L, 43 g/L, 44 g/L, 45 g/L, 46 g/L, 47 g/L, 48 g/L, 49 g/L, 50 g/L, 51 g/L, 52 g/L, 53 g/L, 54 g/L, 55 g/L, 56 g/L, 57 g/L, 58 g/L, 59 g/L, 60 g/L, 61 g/L, 62 g/L, 63 g/L, 64 g/L, 65 g/L, 66 g/L, 67 g/L, 68 g/L, 69 g/L, 70 g/L, 71 g/L, 72 g/L, 73 g/L, 74 g/L, 75 g/L, 76 g/L, 77 g/L, 78 g/L, 79 g/L, 80 g/L, 81 g/L, 82 g/L, 83 g/L, 84 g/L, 85 g/L, 86 g/L, 87 g/L, 88 g/L, 89 g/L, 90 g/L, 91 g/L, 92 g/L, 93 g/L, 94 g/L, 95 g/L, 96 g/L, 97 g/L, 98 g/L, 99 g/L, 100 g/L, 101 g/L, 102 g/L, 103 g/L, 104 g/L, 105 g/L, 106 g/L, 107 g/L, 108 g/L, 109 g/L, 110 g/L, 111 g/L, 112 g/L, 113 g/L, 114 g/L, 115 g/L, 116 g/L, 117 g/L, 118 g/L, 119 g/L, 120 g/L, 121 g/L, 122 g/L, 123 g/L, 124 g/L, 125 g/L, 126 g/L, 127 g/L, 128 g/L, 129 g/L, 130 g/L, 131 g/L, 132 g/L, 133 g/L, 134 g/L, 135 g/L, 136 g/L, 137 g/L, 138 g/L, 139 g/L, 140 g/L, 141 g/L, 142 g/L, 143 g/L, 144 g/L, 145 g/L, 146 g/L, 147 g/L, 148 g/L, 149 g/L, or 150 g/L.

The carbon substrate, like the nitrogen substrate, is necessary for cell production and enzyme production, but unlike the nitrogen substrate, it serves as the raw material for production of end products. Frequently, more carbon substrate can lead to greater production of end products. In another embodiment, it can be advantageous to operate with the carbon level and nitrogen level related to each other for at least a portion of the fermentation time. In one embodiment, the ratio of carbon to nitrogen is maintained within a range of about 30:1 to about 10:1. In another embodiment, the ratio of carbon nitrogen is maintained from about 20:1 to about 10:1 or more preferably from about 15:1 to about 10:1. In another embodiment the ratio of carbon nitrogen is about 30:1, 29:1, 28:1, 27:1, 26:1, 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, or 1:1.

Maintaining the ratio of carbon and nitrogen ratio within particular ranges can result in benefits to the operation such as the rate of metabolism of carbon substrate, which depends on the amount of carbon substrate and the amount and activity of enzymes present, being balanced to the rate of end product production. Balancing the carbon to nitrogen ratio can, for example, facilitate the sustained production of these enzymes such as to replace those which have lost activity.

In another embodiment, the amount and/or timing of carbon, nitrogen, or other medium component addition can be related to measurements taken during the fermentation. For example, the amount of monosaccharides present, the amount of insoluble polysaccharide present, the polysaccharase activity, the amount of product present, the amount of cellular material (for example, packed cell volume, dry cell weight, etc.) and/or the amount of nitrogen (for example, nitrate, nitrite, ammonia, urea, proteins, amino acids, etc.) present can be measured. The concentration of the particular species, the total amount of the species present in the fermentor, the number of hours the fermentation has been running, and the volume of the fermentor can be considered. In various embodiments, these measurements can be compared to each other and/or they can be compared to previous measurements of the same parameter previously taken from the same fermentation or another fermentation. Adjustments to the amount of a medium component can be accomplished such as by changing the flow rate of a stream containing that component or by changing the frequency of the additions for that component. For example, the amount of saccharide can be increased when the cell production increases faster than the end product production. In another embodiment the amount of nitrogen can be increased when the enzyme activity level decreases.

In another embodiment, a fed batch operation can be employed, wherein medium components and/or fresh cells are added during the fermentation without removal of a portion of the broth for harvest prior to the end of the fermentation. In one embodiment a fed-batch process is based on feeding a growth limiting nutrient medium to a culture of microorganisms. In one embodiment the feed medium is highly concentrated to avoid dilution of the bioreactor. In another embodiment the controlled addition of the nutrient directly affects the growth rate of the culture and avoids overflow metabolism such as the formation of side metabolites. In one embodiment the growth limiting nutrient is a nitrogen source or a saccharide source.

In various embodiments, particular medium components can have beneficial effects on the performance of the fermentation, such as increasing the titer of desired products, or increasing the rate that the desired products are produced. Specific compounds can be supplied as a specific, pure ingredient, such as a particular amino acid, or it can be supplied as a component of a more complex ingredient, such as using a microbial, plant or animal product as a medium ingredient to provide a particular amino acid, promoter, cofactor, or other beneficial compound. In some cases, the particular compound supplied in the medium ingredient can be combined with other compounds by the organism resulting in a fermentation-beneficial compound. One example of this situation would be where a medium ingredient provides a specific amino acid which the organism uses to make an enzyme beneficial to the fermentation. Other examples can include medium components that are used to generate growth or product promoters, etc. In such cases, it can be possible to obtain a fermentation-beneficial result by supplementing the enzyme, promoter, growth factor, etc. or by adding the precursor. In some situations, the specific mechanism whereby the medium component benefits the fermentation is not known, only that a beneficial result is achieved.

In one embodiment, a fermentation to produce a fuel is performed by culturing a strain of *R. opacus* in a medium having a supplement of lignin component and a concentration of one or more carbon sources. The resulting production of end product such as TAG can be up to 1-fold, 2-fold, 3-fold, 4-fold, 5-fold, 6-fold, 7-fold, 8-fold, 9-fold, and in some cases up to 10-fold and higher in volumetric productivity than a process using only the addition of a relatively pure saccharide source, and can achieve a carbon conversion efficiency approaching the theoretical maximum. The theoretical maximum can vary with the substrate and product. For example, the generally accepted maximum efficiency for conversion of glucose to ethanol is 0.51 g ethanol/g glucose. In one embodiment a biocatalyst can produce about 40-100% of a theoretical maximum yield of ethanol. In another embodiment, a biocatalyst can produce up to about 40%, 50%, 60%, 70%, 80%, 90%, 95% and even 100% of the theoretical maximum yield of ethanol. In one embodiment a biocatalyst can produce up to about 1% 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.99%, or 100% of a theoretical maximum yield of a fuel. It can be possible to obtain a fermentation-beneficial result by supplementing the medium with a pretreatment or hydrolysis component. In some situations, the specific mechanism whereby the medium component benefits the fermentation is not known, only that a beneficial result is achieved.

Various embodiments offer benefits relating to improving the titer and/or productivity of fermentation end-product production by a biocatalyst by culturing the organism in a medium comprising one or more compounds comprising particular fatty acid moieties and/or culturing the organism under conditions of controlled pH.

In one embodiment, the pH of the medium is controlled at less than about pH 7.2 for at least a portion of the fermentation. In one embodiment, the pH is controlled within a range of about pH 3.0 to about 7.1 or about pH 4.5 to about 7.1, or about pH 5.0 to about 6.3, or about pH 5.5 to about 6.3, or about pH 6.0 to about 6.5, or about pH 5.5 to about 6.9 or about pH 6.2 to about 6.7. The pH can be controlled by the addition of a pH modifier. In one embodiment, a pH modifier is an acid, a base, a buffer, or a material that reacts with other materials present to serve to raise of lower the pH. In one embodiment, more than one pH modifier can be used, such as more than one acid, more than one base, one or more acid with one or more bases, one or more acids with one or more buffers, one or more bases with one or more buffers, or one or more acids with one or more bases with one or more buffers. When more than one pH modifiers are utilized, they can be added at the same time or at different times. In one embodiment, one or more acids and one or more bases can be combined, resulting in a buffer. In one embodiment, media components, such as a carbon source or a nitrogen source can also serve as a pH modifier; suitable media components include those with high or low pH or those with buffering capacity. Exemplary media components include acid- or base-hydrolyzed plant polysaccharides having with residual acid or base, AFEX treated plant material with residual ammonia, lactic acid, corn steep solids or liquor.

In one embodiment, a constant pH can be utilized throughout the fermentation. In one embodiment, the timing and/or amount of pH reduction can be related to the growth conditions of the cells, such as in relation to the cell count, the end product produced, the end product present, or the rate of end product production. In one embodiment, the pH reduction can be made in relation to physical or chemical properties of the fermentation, such as viscosity, medium composition, gas production, off gas composition, etc.

Recovery of Fermentive End Products

In another aspect, methods are provided for the recovery of the fermentive end products, such as an alcohol (e.g. ethanol, propanol, methanol, butanol, etc.) another biofuel or chemical product. In one embodiment, broth will be harvested at some point during of the fermentation, and fermentive end product or products will be recovered. The broth with end product to be recovered will include both end product and impurities. The impurities include materials such as water, cell bodies, cellular debris, excess carbon substrate, excess nitrogen substrate, other remaining nutrients, other metabolites, and other medium components or digested medium components. During the course of processing the broth, the broth can be heated and/or reacted with various reagents, resulting in additional impurities in the broth.

In one embodiment, the processing steps to recover end product frequently includes several separation steps, including, for example, distillation of a high concentration alcohol material from a less pure alcohol-containing material. In one embodiment, the high concentration ethanol material can be further concentrated to achieve very high concentration alcohol, such as 98% or 99% or 99.5% (wt.) or even higher. Other separation steps, such as filtration, centrifugation, extraction, adsorption, etc. can also be a part of some recovery processes for alcohol as a product or biofuel, or other biofuels or chemical products.

In one embodiment a process can be scaled to produce commercially useful biofuels. In another embodiment biocatalyst is used to produce an alcohol, e.g., ethanol, butanol, propanol, methanol, or a fuel such as hydrocarbons hydrogen, TAG, and hydroxy compounds. In another embodiment biocatalyst is used to produce a carbonyl compound such as an aldehyde or ketone (e.g. acetone, formaldehyde, 1-propanal, etc.), an organic acid, a derivative of an organic acid such as an ester (e.g. wax ester, glyceride, etc.), 1, 2-propanediol, 1,3-propanediol, lactic acid, formic acid, acetic acid, succinic acid, pyruvic acid, or an enzyme such as a cellulase, polysaccharase, lipases, protease, ligninase, and hemicellulase.

TAG biosynthesis is widely distributed in nature and the occurrence of TAG as reserve compounds is widespread among plants, animals, yeast and fungi. In contrast, however, TAGs have not been regarded as common storage compounds in bacteria. Biosynthesis and accumulation of TAGs have been described only for a few bacteria belonging to the actinomycetes group, such as genera of *Streptomyces, Nocardia, Rhodococcus, Mycobacterium, Dietzia* and *Gordonia*, and, to a minor extent, also in a few other bacteria, such as *Acineto-*

*bacter baylyi* and *Alcanivorax borkumensis*. Since the mid-1990's, TAG production in hydrocarbon-degrading strains of those genera has been frequently reported. TAGs are stored in spherical lipid bodies as intracellular inclusions, with the amounts depending on the respective species, cultural conditions and growth phase. Commonly, the important factor for the production of TAGs is the amount of nitrogen that is supplied to the culture medium. The excess carbon, which is available to the culture after nitrogen exhaustion, continues to be assimilated by the cells and, by virtue of oleaginous bacteria possessing the requisite enzymes, is converted directly into lipid. The compositions and structures of bacterial TAG molecules vary considerably depending on the bacterium and on the cultural conditions, especially the carbon sources. See, Brigham C J, et al. (2011) J Microbial Biochem Technol S3:002.

In one embodiment, useful biochemicals can be produced from non-food plant biomass, with a steam or hot-water extraction technique that is carried out by contacting a charge of non-food plant pretreated biomass material such as corn stover or sorghum with water and/or acid (with or without additional process enhancing compounds or materials), in a pressurized vessel at an elevated temperature up to about 160-220° C. and at a pH below about 7.0, to yield an aqueous (extract solution) mixture of useful saccharides including long-chain saccharides (saccharides), acetic acid, and lignin, while leaving the structural (cellulose and lignin) portion of the lignocellulosic material largely intact. In combination, these potential inhibitory chemicals especially saccharide degradation products are low, and the plant derived nutrients that are naturally occurring lignocellulosic-based components are also recovered that are beneficial to a C5 and C6 fermenting organism. Toward this objective, the aqueous extract is concentrated (by centrifugation, filtration, solvent extraction, flocculation, evaporation), by producing a concentrated saccharide stream, apart from the other hemicellulose (C5 rich) and cellulosic derived saccharides (C6 rich) which are channeled into a fermentable stream.

In another embodiment, following enzyme/acid hydrolysis, additional chemical compounds that are released are recovered with the saccharide stream resulting in a short-chain saccharide solution containing xylose, mannose, arabinose, rhamnose, galactose, and glucose (5 and 6-carbon saccharides). The saccharide stream, now significantly rich in C5 and C6 substances can be converted by microbial fermentation or chemical catalysis into such products as triacylglycerol or TAG and further refined to produce stream rich in JP8 or jet fuels. If C5 saccharide percentage correction has not been performed, it can be performed before fermentation to satisfy desired combination of C5 and C6 saccharides for the fermentation organism and corresponding end product.

Biofuel Plant and Process of Producing Biofuel:

Generally, there are several basic approaches to producing fuels and chemical end-products from biomass on a large scale utilizing of microbial cells. In the one method, one first pretreats and hydrolyzes a biomass material that includes high molecular weight carbohydrates to lower molecular weight carbohydrates, and then ferments the lower molecular weight carbohydrates utilizing of microbial cells to produce fuel or other products. In the second method, one treats the biomass material itself using mechanical, chemical and/or enzymatic methods. In all methods, depending on the type of biomass and its physical manifestation, one of the processes can comprise a milling of the carbonaceous material, via wet or dry milling, to reduce the material in size and increase the surface to volume ratio (physical modification).

In one embodiment, hydrolysis can be accomplished using acids, e.g., Bronsted acids (e.g., sulfuric or hydrochloric acid), bases, e.g., sodium hydroxide, hydrothermal processes, ammonia fiber explosion processes ("AFEX"), lime processes, enzymes, or combination of these. Hydrogen, and other end products of the fermentation can be captured and purified if desired, or disposed of, e.g., by burning. For example, the hydrogen gas can be flared, or used as an energy source in the process, e.g., to drive a steam boiler, e.g., by burning. Hydrolysis and/or steam treatment of the biomass can, e.g., increase porosity and/or surface area of the biomass, often leaving the cellulosic materials more exposed to the biocatalyst cells, which can increase fermentation rate and yield. Removal of lignin can, e.g., provide a combustible fuel for driving a boiler, and can also, e.g., increase porosity and/or surface area of the biomass, often increasing fermentation rate and yield. Generally, in any of the these embodiments, the initial concentration of the carbohydrates in the medium is greater than 20 mM, e.g., greater than 30 mM, 50 mM, 75 mM, 100 mM, 150 mM, 200 mM, or even greater than 500 mM.

Biomass Processing Plant and Process of Producing Products from Biomass

In one aspect, a fuel or chemical plant that includes a pretreatment unit to prepare biomass for improved exposure and biopolymer separation, a hydrolysis unit configured to hydrolyze a biomass material that includes a high molecular weight carbohydrate, and one or more product recovery system(s) to isolate a product or products and associated by-products and co-products is provided. In another aspect, methods of purifying lower molecular weight carbohydrate from solid byproducts and/or toxic impurities is provided.

In another aspect, methods of making a product or products that include combining biocatalyst cells of a microorganism and a biomass feed in a medium wherein the biomass feed contains lower molecular weight carbohydrates and unseparated solids and/or other liquids from pretreatment and hydrolysis, and fermenting the biomass material under conditions and for a time sufficient to produce a biofuel, chemical product or fermentive end-products, e.g. ethanol, propanol, hydrogen, succinic acid, lignin, terpenoids, and the like as described above, is provided.

In another aspect, products made by any of the processes described herein is also provided herein.

Figure 9:
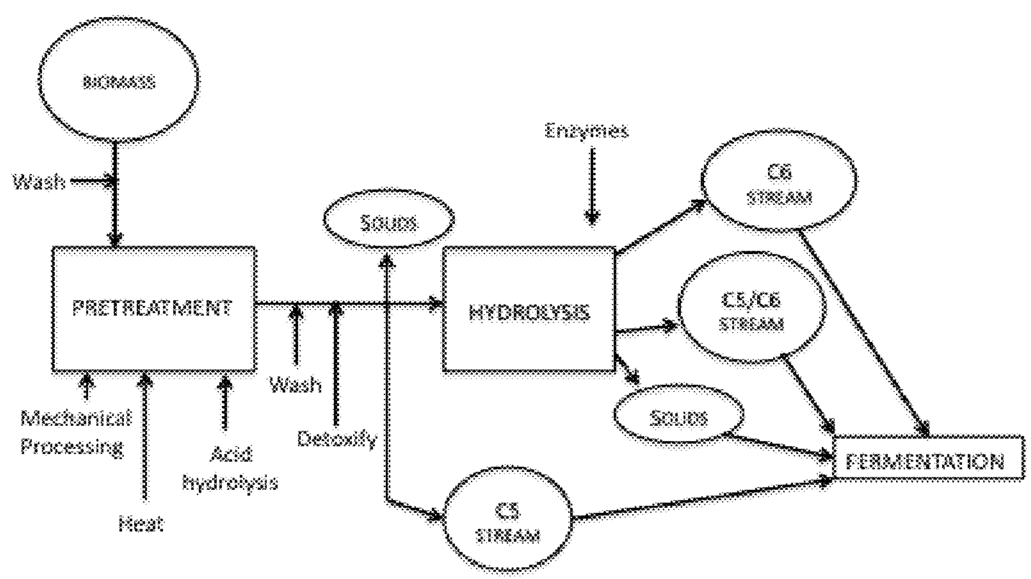
FIG. 9 shows a processing diagram for conversion of feedstock to saccharide streams and residuals.

FIG. 9 is an example of a method for producing chemical products from biomass by a first mechanical treatment that consists of one or more steps, depending on the condition of the biomass feedstock. In a first step, debris is removed by sifting, sorting, or other means to remove non-carbohydrate containing material. In another step, the feedstock is chopped, shredded, ground or otherwise reduced in size. This process can include dry processing or wet processing. If wet processing occurs, the feedstock can be swollen with steam or hot water and pressure applied to soften or swell the fibers in the material. The material can then be ground to very small size particles. If the feedstock is woody, it is expected that the majority of the processing will be chopping. If a more malleable feedstock is present, grinding, vortexing, or even just hot water and pressure can be all that is necessary. It is expected that the biomass is reduced in size to a fine powder or sludge (if wet) for further processing, if necessary, prior to further pretreatment to produce more accessible cellulose and hemicellulose prior to enzymatic hydrolysis of these polymers.

Biomass is then treated with an acid at elevated temperature and pressure in a hydrolysis unit. The biomass may first be heated by addition of hot water or steam. The biomass may be acidified by bubbling gaseous sulfur dioxide through the biomass that is suspended in water, or by adding a strong acid, e.g., sulfuric, hydrochloric, or nitric acid with or without preheating/presteaming/water addition. During the acidification, the pH is maintained at a low level, e.g., below about 5. The temperature and pressure may be elevated after acid addition. In addition to the acid already in the acidification unit, optionally, a metal salt such as ferrous sulfate, ferric sulfate, ferric chloride, aluminum sulfate, aluminum chloride, magnesium sulfate, or mixtures of these can be added to aid in the acid hydrolysis of the biomass. The acid-impregnated biomass is fed into the hydrolysis section of the pretreatment unit. Steam is injected into the hydrolysis portion of the pretreatment unit to directly contact and heat the biomass to the desired temperature. The temperature of the biomass after steam addition is, e.g., between about 130° C. and 220° C. The acid hydrolysate is then discharged into the flash tank portion of the pretreatment unit, and is held in the tank for a period of time to further hydrolyze the biomass, e.g., into oligosaccharides and monomeric saccharides. Other methods can also be used to further break down biomass. Alternatively, the biomass can be subject to discharge through a pressure lock for any high-pressure pretreatment process. Hydrolysate is then discharged from the pretreatment reactor, with or without the addition of water, e.g., at solids concentrations between about 10% and 60%.

After pretreatment, the biomass may be dewatered and/or washed with a quantity of water, e.g. by squeezing or by centrifugation, or by filtration using, e.g. a countercurrent extractor, wash press, filter press, pressure filter, a screw conveyor extractor, or a vacuum belt extractor to remove acidified fluid. Wash fluids can be collected to concentrate the C5 saccharides in the wash stream. The acidified fluid, with or without further treatment, e.g. addition of alkali (e.g. lime) and or ammonia (e.g. ammonium phosphate), can be re-used, e.g., in the acidification portion of the pretreatment unit, or added to the fermentation, or collected for other use/treatment. Products may be derived from treatment of the acidified fluid, e.g., gypsum or ammonium phosphate. Enzymes or a mixture of enzymes can be added during pretreatment to hydrolyze, e.g. endoglucanases, exoglucanases, cellobiohydrolases (CBH), beta-glucosidases, glycoside hydrolases, glycosyltransferases, alphyamylases, chitinases, pectinases, lyases, and esterases active against components of cellulose, hemicelluloses, pectin, and starch, in the hydrolysis of high molecular weight components.

One aspect of this invention is the reduction in size and uniformity of biomass particles, whether a single feedstock or mixed feedstocks are used. Without being limited by theory, it is believed that an unexpected increase in the conversion of the feedstock to fermentable saccharides is achieved if the size of any feedstock fed to the enzyme hydrolysis reactor is small and uniform, as long as sufficient enzyme is present for hydrolysis of the feedstock. If the cellulosic feedstock that is fed to a hot water, acid, or steam explosion reactor is not uniform and cannot be uniformly treated, then a smaller percentage of the available sites of the feedstock are activated and/or hydrolyzed than would be expected. Further, it is difficult to mix larger-sized particles and process a batch of heterogeneous material so that heat and moisture is evenly distributed; thus resulting in an uneven autohydrolysis reaction. Even transfer of heat, chemicals, and moisture results in reduced processing time, less release of inhibitors, and improved release of hemicellulose and cellulose, especially microcrystalline cellulose. If the temperature in parts of the processing feedstock are too high, then some percentage of the hemicellulose saccharides are degraded to inhibitory compounds. Further, even heat prevents charring of the material that can lead to significant losses in saccharides. This also prevents undercooking which can lead to unhydrolyzed cellulose during enzyme hydrolysis.

Feedstocks pretreated under any of the conditions described above, which are reduced to a uniform size of less than 10 mm, 7.5 mm, 5 mm, 2.5 mm, 2 mm, 1.5 mm, or 1 mm in size (e.g., diameter or length, are then hydrolyzed with enzymes to reduce the carbohydrate polymers to disaccharides or monomeric saccharides. In one embodiment, the particle size is reduced wherein approximately all of the particles are 1.5, 1.4, 1.3, 1.2, 1.1, 1.0, 0.9, 0.8, 0.7, 0.6, 0.5, 0.4, 0.3, 0.2 or 0.1 mm in diameter (or length). In one embodiment wherein isolated enzymes are used, the standard addition or "normal load" is 5% (5 kg)/per 100 kg of the feedstock solids wherein the solids are at 1-25% w/v. The enzymes can be any combination of cellulases, hemicellulases, amylases, lipases, chitinases, pectinases, etc., depending on the combination and kind of polymers in the solids mix. In another embodiment of this invention, wherein the particle size of the feedstock is uniformly reduced to a size of less than 10 mm, 7.5 mm, 5 mm, 2.5 mm, 2 mm, 1.5 mm, or 1 mm in size (e.g., diameter or length), the enzyme addition can be reduced to 20% (1.0 kg per 100 kg solids), 25% (1.25 kg per 100 kg solids), 30% (1.5 kg per 100 kg solids), 35% (1.75 kg per 100 kg solids), 40% (2.0 kg per 100 kg solids), 45% (2.25 kg per 100 kg solids), 50% (2.50 kg per 100 kg solids), 55% (2.75 kg per 100 kg solids), 60% (3.0 kg per 100 kg solids), 65% (3.25 kg per 100 kg solids), 70% (3.5 kg per 100 kg solids), 75% (3.75 kg per 100 kg solids), 80 (4.0 kg per 100 kg solids), 85% (4.25 kg per 100 kg solids), or 90% (4.5 kg per 100 kg solids) of a normal load. Preferably, the total enzyme addition is 1% (1 kg) per 100 kg solids for particles less than 1 mm in diameter or length.

The commercial viability of a hydrolysis process is dependent on the character of the feedstock provided to the hydrolysis unit. If such an activated feedstock is provided to an enzymatic hydrolysis unit, then at least 60%, preferably more than 75% and more preferably over 90% of the cellulose and hemicelluloses may be converted to monomeric saccharides. This saccharide rich process stream may subsequently be subjected to fermentation to produce an alcohol stream. The alcohol stream from the fermentation stage (e.g., the raw alcohol stream) may have an alcohol content of about 3-22% v/v, preferably about 5-15% and more preferably more about 8-12%.

In another embodiment, a combination of isolated enzymes and a microorganism that produces carbohydrate polymerases can be used to hydrolyze the polymers in an SSF reaction whereby the microorganism's enzymatic metabolism is supplemented by the addition of enzymes. In one embodiment, the additional enzymes are primarily hemicellulases and the microorganism is able to produce C6 monomeric saccharides or oligomers from polymers. An example would be yeasts, *C. thermocellum*, or *C. beijerinckii*, and the product produced from the saccharides is an alcohol, such as ethanol or butanol. In another embodiment, the microorganism is a C5/C6 hydrolyzing microorganism, such as *C. phytofermentans* and the addition of other enzymes speeds up the fermentation process. In either type of process, the additional enzymes can be added prior to microorganism in an SHF process or simultaneously with the microorganism (SSF), or in a "fed-batch" type process wherein the exogenous enzyme is added partially before or through the fermentation process with a microorganism. The reduced particle size can assist such microorganisms in accessibility of, not only the exogenous enzyme which amount can be reduced, but in making the carbohydrate polymers more available to the endogenously-produced enzymes of the microorganism.

Examples of such organisms, in addition to those described supra, *Clostridium thermohydrosulfuricum, Thermoanaerobacter ethanolicus, Theroanaerobium brockii, T reesei, Aspergilus* sp., *Rhizopus* sp., *Zygmitis* sp., *Trichosporon cutaneum, R. albus, B. succinogenes, B. fibrisolvens, R. flavefaciens, E. cellulosolvens, C. cellobioparum, Chlorella* sp., and the like. Also, recombinant cellulolytic or xylanolytic microorganisms have been developed by expressing heterologous cellulases or hemicellulases, such as *S. cerevisiae, Z. mobilis, E. coli, K. marxianus, A. aculeatus, Thermoanaerobacterium saccharolyticum, Pichia stipitis, H. polymorpha, Klebsiella oxytoca, R. opacus*, and the like. Further, there are examples of amylolytic microorganisms that can benefit from the addition of exogenous enzymes to make starch more accessible. In one embodiment, examples of amylolytic yeasts and bacteria are *Saccharomyces castelli, S. diastaticus, Edomycopsis filbuligera, C. thermohydrosulfuricum.*

In another embodiment, it would be understood by those of skill in the art that the microorganism enzymes are more efficient in such processes as those described supra since the small particle size benefits the microorganism's enzyme. The same advantages of uniform small particle size and access to hemicellulose and cellulose fractions would apply to any enzyme, whether enmeshed in a cellulosome or extracellular docking type molecules. The reduced inhibitor fraction and additional available microcrystalline cellulose can reduce lag periods of initial growth.

A fermenter, attached or at a separate site, can be fed with hydrolyzed biomass, any liquid fraction from biomass pretreatment, an active seed culture of a biocatalyst, such as a yeast, if desired a co-fermenting microbe, e.g., another yeast or *E. coli*, and, if required, nutrients to promote growth of the biocatalyst or other microbes. Alternatively, the pretreated biomass or liquid fraction can be split into multiple fermenters, each containing a different strain of a biocatalyst and/or other microbes, and each operating under specific physical conditions. Fermentation is allowed to proceed for a period of time, e.g., between about 1 and 150 hours, while maintaining a temperature of, e.g., between about 25° C. and 50° C. Gas produced during the fermentation is swept from fermentor and is discharged, collected, or flared with or without additional processing, e.g. hydrogen gas may be collected and used as a power source or purified as a co-product.

In another aspect, methods of making a fuel or fuels that include combining one or more biocatalyst and a lignocellulosic material (and/or other biomass material) in a medium, adding a lignin fraction from pretreatment, and fermenting the lignocellulosic material under conditions and for a time sufficient to produce a fuel or fuels, e.g., ethanol, propanol and/or hydrogen or another chemical compound is provided herein.

In another aspect, the products made by any of the processes described herein is provided.

EXAMPLES

The following examples serve to illustrate certain embodiments and aspects and are not to be construed as limiting the scope thereof.

Example 1

Pretreatment of Corn Stover and Wheat Straw

This is a direct comparison of saccharification yields between pretreated biomass compositions comprising larger and heterogeneous lignocellulosic biomass particles (solids A) and small, homogeneous biomass particles (solids B).

Solids A is wheat straw that was ground using standard milling techniques to produce particles sizes of 0.5 to 2.5 cm in length with about a 1 mm thickness. These solids were soaked for 16 hours at about 35% total solids in water containing 1% v/w sulfuric acid based on the dry weight of the solids. The acid soaked material (pH about 2.9) was then charged to a pressurized steam explosion batch reactor where they were held at a temperature of about 200° C. and a pressure of 231 psig for 7.5 minutes before explosive pressure release.

Solids B is wheat straw that was pretreated according to the methods disclosed herein. Briefly, the wheat straw was hydrated in water containing 1.8% v/w sulfuric acid based on dry biomass weight for 15-20 minutes at about 50° C. The hydrated material was then cut by rotating blades and dewatered to a solids content of about 30% by dry biomass weight. The dewatered solids were then simultaneously injected with steam and cut by a second set of rotating blades to produce solid particles less than 1.5 mm in size. The small, homogenous particles were maintained at a temperature of about 160° C. to 180° C. and a pressure of about 135 psig for about 10 minutes before explosive pressure release.

The water content of both the Solids A and Solids B samples were determined and adjusted to a solids content of about 8% (w/v) solids (moisture content of about 85% (w/v) using a 24 hour soaking treatment. Other samples were adjusted to a solids content of 8%, or 10% solids.

Table 1 shows the percent cellulose, hemicellulose, lignin and other components of corn stover and wheat straw.

TABLE 1

| % Composition | Corn Stover | Wheat Straw |
|---|---|---|
| Cellulose -C6 | 49.4 | 38.0 |
| Hemicellulose Xylan -C5 | 22.9 | 23.3 |
| Lignin | 20.6 | 21 |
| Others | 7.1 | 13.4 |

Example 2

Saccharification

The hemicellulase and cellulase enzymes used were provided by Novozymes (Novozymes A/S, Krogshoejvej 36, 2880 Bagsvaerd Denmark). When referring to an enzyme dosage (e.g., 1× or 5% based on dry solids (v/w)) it means that the enzymes were blended together to total 5% based on dry solids. All Samples were analyzed using HPLC and a Bio-Rad HPX-87H Aminex column.

Standard National Renewable Energy Laboratory (NREL) procedures were used to determine the theoretical yields of C6 and C5 saccharides by HPLC, including lignin and extractives. See A Sluiter, et al., Determination of Structural Carbohydrates and Lignin in Biomass (NREL, revised June 2010), which is hereby incorporated by reference in its entirety. Briefly, a 72% sulfuric acid hydrolysis is performed on the input, dried biomass solids. The results from the 72% acid hydrolysis indicate the total carbohydrate content of the dried biomass solids. This is considered the theoretical maximum amount of sugars. The amount of sugars released, as measured by HPLC, is then compared to the theoretical maximum of sugars that can be released from a given mass of starting solids.

Tables 2 and 3 directly compare solids taken from A and B treated material. Both solid sets were adjusted to 8% solids (w/v) and hydrolyzed using 1× the standard enzyme dosage (5% loading based on total dry solids) (v/w). The Tables show the percent conversion of xylan and cellulose based on the total theoretical yields of saccharides within the biomass.

Before enzymatic hydrolysis, Solids B contained an 87.42% theoretical yield of xylose. In comparison, Solids A did not contain any xylose. After only 21 hr, the conversion rates for cellulose and xylan are surprisingly superior for Solids B (e.g., after particle size reduction and in homogeneous material). The xylose saccharide stream is also more transparent in appearance, indicating the reduction in inhibitors.

TABLE 2

| "A" % Conversion - 8% Solids 1× Enzymes | | | | |
|---|---|---|---|---|
| Time (in Hours) | 0 | 21 | 48 | 96 |
| Glucose | 0.00 | 79.94 | 89.62 | 92.88 |
| Xylose | 0.00 | 86.87 | 97.63 | 103.79 |

TABLE 3

| "B" % Conversion - 8% Solids 1× Enzymes | | | | |
|---|---|---|---|---|
| Time (in Hours) | 0 | 21 | 48 | 96 |
| Glucose | 0.00 | 91.78 | 98.39 | 98.47 |
| Xylose | 87.42 | 93.06 | 100.71 | 102.39 |

Tables 4 and 5 directly compare solids taken from A and B treated material wherein both solid sets were adjusted to 8% solids (w/v) and hydrolyzed using 0.5× the standard enzyme dosage (2.5% loading based on total dry solids) (v/w). The Tables show the percent conversion of xylan and cellulose based on the total theoretical yields of saccharides within the biomass. Again, it only takes 21 hr, to demonstrate that the conversion rates for cellulose and xylan are highly superior after particle size reduction and in homogeneous material. The glucose saccharide stream shows almost complete conversion after 48-96 hrs.

TABLE 4

| "A" % Conversion - 8% Solids 0.5× Enzymes | | | | |
|---|---|---|---|---|
| Time (in Hours) | 0 | 21 | 48 | 96 |
| Glucose | 0.00 | 57.72 | 67.62 | 73.43 |
| Xylose | 0.00 | 79.14 | 91.49 | 97.49 |

TABLE 5

| "B" % Conversion - 8% Solids 0.5× Enzymes | | | | |
|---|---|---|---|---|
| Time (in Hours) | 0 | 21 | 48 | 96 |
| Glucose | 0.00 | 81.29 | 98.25 | 98.01 |
| Xylose | 87.42 | 91.50 | 99.72 | 99.61 |

Tables 6 and 7 directly compare solids taken from A and B treated material wherein both solid sets were adjusted to 8% solids (w/v) and hydrolyzed using 0.25× the standard enzyme dosage (1.25% loading based on total dry solids) (v/w). The Tables show the percent conversion of xylan and cellulose based on the total theoretical yields of saccharides within the biomass. At all time points, even reducing enzyme addition to only one-quarter of recommended levels, the conversion rates for cellulose and xylan are highly superior after particle size reduction and in homogeneous material.

TABLE 6

| "A" % Conversion - 8% Solids 0.25× Enzymes | | | | |
|---|---|---|---|---|
| Time (in Hours) | 0 | 21 | 48 | 96 |
| Glucose | 0.00 | 35.68 | 45.86 | 55.29 |
| Xylose | 0.00 | 67.24 | 86.58 | 95.76 |

TABLE 7

| "B" % Conversion - 8% Solids 0.25× Enzymes | | | | |
|---|---|---|---|---|
| Time (in Hours) | 0 | 21 | 48 | 96 |
| Glucose | 0.00 | 57.32 | 78.18 | 90.06 |
| Xylose | 87.42 | 88.90 | 98.23 | 98.69 |

Tables 8 and 9 directly compare solids taken from A and B treated material wherein both solid sets were adjusted to 10% solids (w/v) and hydrolyzed using 1× the standard enzyme dosage (5% loading based on total dry solids) (v/w). The Tables show the percent conversion of xylan and cellulose based on the total theoretical yields of saccharides within the biomass. At all time points, the conversion rates for cellulose and xylan are highly superior after particle size reduction and in homogeneous material showing clearly that, even under a high solids load, that biomass B mixes more evenly and provides better enzyme access to cellulose and hemicellulose polymers.

TABLE 8

| "A" % Conversion - 10% Solids 1× Enzymes | | | | |
|---|---|---|---|---|
| Time (in Hours) | 0 | 21 | 48 | 96 |
| Glucose | 0.00 | 74.15 | 84.24 | 86.89 |
| Xylose | 0.00 | 86.89 | 97.75 | 102.30 |

TABLE 9

| "B" % Conversion - 10% Solids 1× Enzymes | | | | |
|---|---|---|---|---|
| Time (in Hours) | 0 | 21 | 48 | 96 |
| Glucose | 0.00 | 92.90 | 97.56 | 98.41 |
| Xylose | 87.42 | 96.66 | 103.59 | 102.67 |

Tables 10 and 11 directly compare solids taken from A and B treated material wherein both solid sets were adjusted to 10% solids (w/v) and hydrolyzed using 0.5× the standard enzyme dosage (0.25% loading based on total dry solids) (v/w). The Tables show the percent conversion of xylan and cellulose based on the total theoretical yields of saccharides within the biomass. With half the normal complement of enzyme, the conversion rates for cellulose and xylan are highly superior after particle size reduction and in homogeneous material showing clearly that, even under a high solids load, that biomass B mixes more evenly and provides better enzyme access to cellulose and hemicellulose polymers.

TABLE 10

| "A" % Conversion - 10% Solids 0.5× Enzymes | | | | |
|---|---|---|---|---|
| Time (in Hours) | 0 | 21 | 48 | 96 |
| Glucose | 0.00 | 57.75 | 73.38 | 74.83 |
| Xylose | 0.00 | 77.37 | 97.75 | 94.04 |

TABLE 11

| "B" % Conversion - 10% Solids 0.5× Enzymes | | | | |
|---|---|---|---|---|
| Time (in Hours) | 0 | 21 | 48 | 96 |
| Glucose | 0.00 | 76.00 | 92.72 | 93.41 |
| Xylose | 87.42 | 94.66 | 100.41 | 101.19 |

Tables 12 and 13 directly compare solids taken from A and B treated material wherein both solid sets were adjusted to 10% solids (w/v) and hydrolyzed using 0.25× the standard enzyme dosage (1.25% loading based on total dry solids) (v/w). The Tables show the percent conversion of xylan and cellulose based on the total theoretical yields of saccharides within the biomass. At all time points, the conversion rates for cellulose and xylan are highly superior after particle size reduction and in homogeneous material showing clearly that, even under a high solids load, that biomass B mixes more evenly and provides better enzyme access to cellulose and hemicellulose polymers.

TABLE 12

| "A" % Conversion - 10% Solids 0.25× Enzymes | | | | |
|---|---|---|---|---|
| Time (in Hours) | 0 | 21 | 48 | 96 |
| Glucose | 0.00 | 40.02 | 49.98 | 55.24 |
| Xylose | 0.00 | 68.98 | 82.52 | 88.08 |

TABLE 13

| "B" % Conversion - 10% Solids 0.25× Enzymes | | | | |
|---|---|---|---|---|
| Time (in Hours) | 0 | 21 | 48 | 96 |
| Glucose | 0.00 | 62.22 | 83.96 | 95.23 |
| Xylose | 87.42 | 91.92 | 100.41 | 102.67 |

To sum up this data, FIGS. 1-4 show a direct comparison of polymer-to-saccharide conversion percentage with each enzyme dosage (1×, 0.5× and 0.25×) as well as a direct comparison between the percentage of solids used during enzymatic hydrolysis (8% and 10%).

Figure 5:
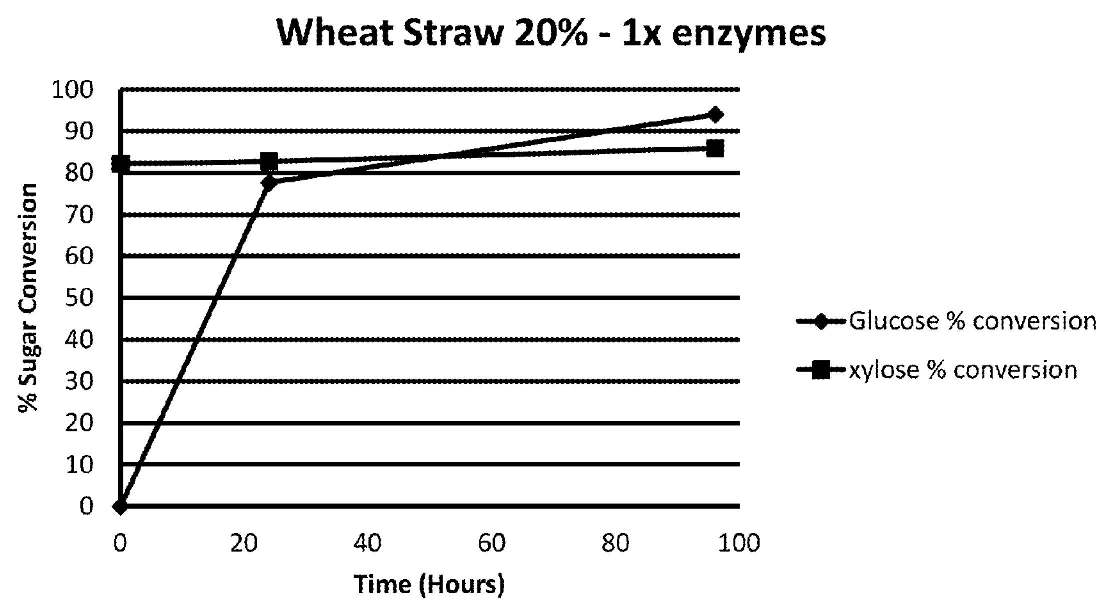
FIG. 5 shows glucose and xylose conversion from cellulose and hemicellulose, respectively, using 1× enzyme loading with 20% solids.
Figure 6:
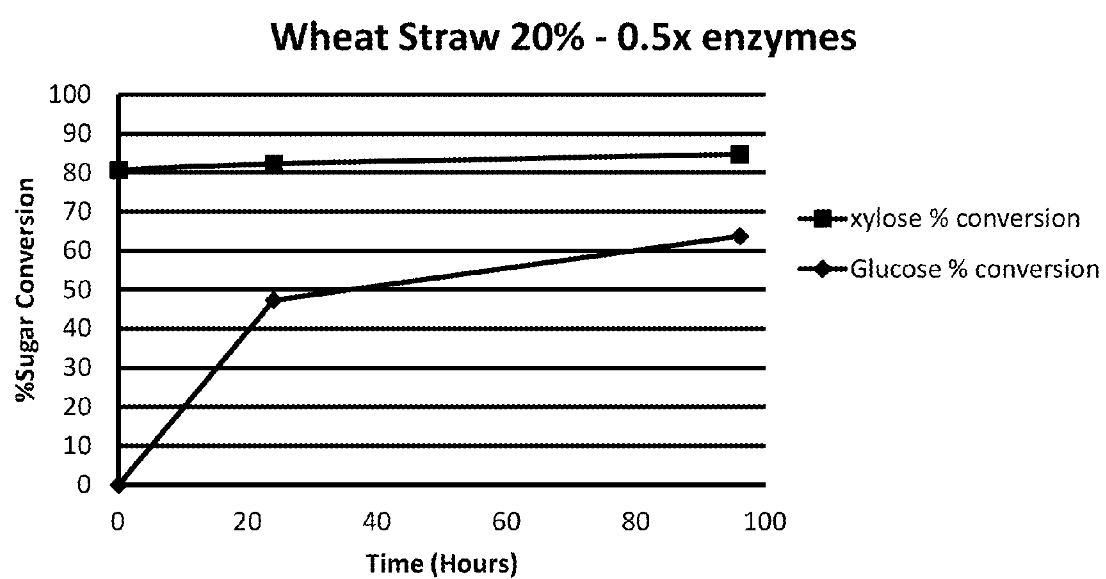
FIG. 6 shows glucose and xylose conversion from cellulose and hemicellulose, respectively, using 0.50× enzyme loading with 20% solids.
Figure 7:
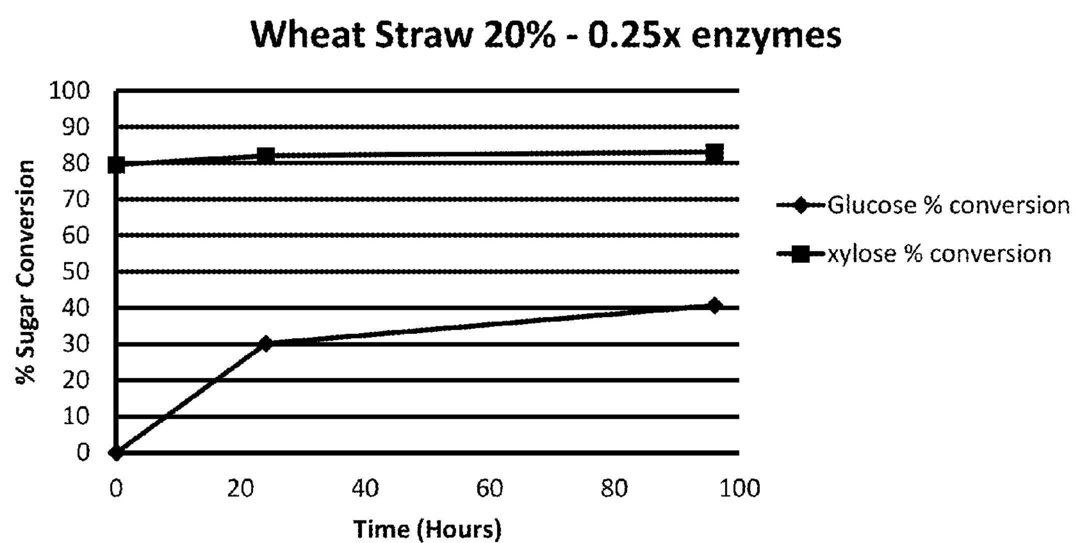
FIG. 7 shows glucose and xylose conversion from cellulose and hemicellulose, respectively, using 0.25× enzyme loading with 20% solids.

In addition to 8% and 10% solids, 20% solids were also tested with reduced enzyme doses. Wheat straw was processed as described above for "B" and the solids were made up to 20% w/v prior to enzyme addition. FIGS. 5, 6 and 7 directly compare the saccharification of wheat straw sets that were adjusted to 20% solids (w/v) and hydrolyzed using 1.0×, 0.50× and 0.25× the standard enzyme dosage (v/w). FIG. 5 shows the percent conversion of xylan and cellulose based on the total theoretical yields of saccharides within the biomass are rapid and very high suggesting that there is little, if any, inhibitor activity. FIG. 6 shows only a slight reduction in glucose conversion for a half-dose of enzymes and the rate of C5 conversion remains very high. FIG. 7 shows a slight reduction in xylose conversion from xylan and a slower rate of conversion of glucose from cellulose. At all time points, the conversion rates for cellulose and xylan were still considerable after particle size reduction and in homogeneous material showing clearly that, even under a high solids load, that biomass B mixes more evenly and provides better enzyme access to cellulose and hemicellulose polymers.

Example 3

Pretreatment and Hydrolysis of Corn Cobs

Figure 8:
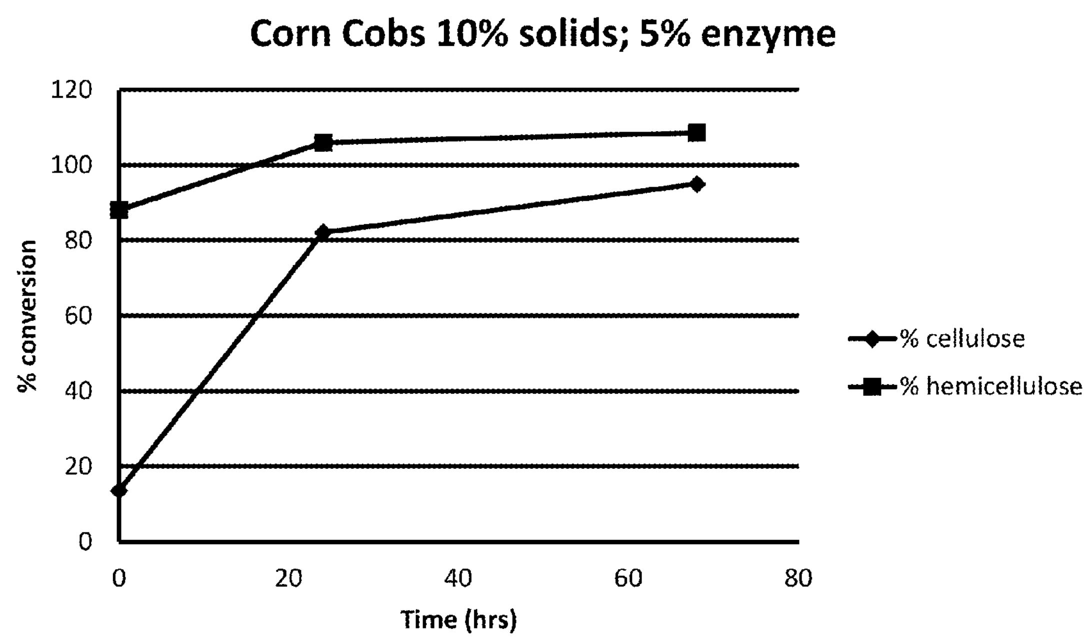
FIG. 8 shows glucose and xylose conversion from cellulose and hemicellulose, respectively, using 1× enzyme loading with 10% solids.

In this example, corn cobs were pretreated and hydrolyzed as described for solids B in Examples 1 and 2. The corncobs were hydrolyzed at 10% solids by dry biomass weight using a 5% v/w (1×) enzyme load. The yields of glucose and xylose were measured at 0, 24, and 68 hours of hydrolysis. The results are tabulated in Table 14 and graphed in FIG. 8. At time 0, the percent yield from the hemicellulose was 88.08% of the theoretical maximum while the yield of glucose was 13.60% of the theoretical maximum. By 24 hours, the yield of glucose had increased to greater than 80% of the theoretical maximum; and a 95% yield was achieved after only 68 hours of enzymatic hydrolysis.

TABLE 14

| Time | 0 | 24 | 68 |
|---|---|---|---|
| glucose (g/L) | 6.2 | 31.2 | 36.1 |
| xylose (g/L) | 24.9 | 29.3 | 29.8 |
| arabinose (g/L) | 1.7 | 2.7 | 3 |
| % glucose | 13.59649 | 82.10526 | 95 |
| % hemicellulose | 88.07947 | 105.9603 | 108.6093 |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of producing a composition comprising C5 and C6 saccharides and low levels of an inhibitor compound from a biomass composition comprising cellulose, hemicellulose, and/or lignocellulose, the method comprising:

(a) pretreating the biomass composition comprising cellulose, hemicellulose, and/or lignocellulose to produce a pretreated biomass composition comprising a mixture of solid particles, wherein at least 50% of the solid particles are less than 1.5 mm in a dimension, and C5 monosaccharides and/or disaccharides in a yield that is at least 50% of a theoretical maximum, wherein pretreating produces low levels of the inhibitor compound and comprises:

(i) hydration of the biomass composition in an acid medium to produce a hydrated biomass composition, (ii) mechanical size reduction of the hydrated biomass composition to produce the mixture of solid particles, and (iii) heating the hydrated biomass composition for a time sufficient to produce the pretreated biomass composition comprising C5 monosaccharides and/or disaccharides in the yield that is at least 50% of the theoretical maximum while producing low levels of the inhibitor compound; and (b) hydrolyzing the pretreated biomass composition with one or more enzymes for a time sufficient to produce the composition comprising C5 and C6 saccharides and low levels of the inhibitor compound.

2. The method of claim 1, wherein at least 50% of the mixture of solid particles in the pretreated biomass composition are from about 0.1 mm to about 1 mm in a dimension.

3. The method of claim 1, wherein all of the solid particles in the pretreated biomass are less than 7.5 mm in a dimension.

4. The method of claim 1, wherein all of the solid particles in the pretreated biomass are less than 1 mm in a dimension.

5. The method of claim 1, wherein the yield of C5 monosaccharides and/or disaccharides is at least 80% of the theoretical maximum.

6. The method of claim 1, wherein the pretreated biomass composition further comprises a yield of glucose that is less than about 20% of a theoretical maximum.

7. The method of claim 1, wherein the hydrated biomass composition comprises from about 1% to about 20% solids by dry biomass weight.

8. The method of claim 1, wherein the acid medium is at from about 30° C. to about 70° C.

9. The method of claim 1, wherein hydration of the biomass composition is for about 1 minute to about 60 minutes.

10. The method of claim 1, wherein the acid medium comprises an acid at from about 0.1% to about 5% v/w by dry biomass weight.

11. The method of claim 10, wherein the acid medium comprises the acid that is sulfuric acid, peroxyacetic acid, lactic acid, formic acid, acetic acid, citric acid, phosphoric acid, hydrochloric acid, sulfurous acid, chloroacetic acid, dichloroacetic acid, trichloroacetic acid, trifluoroacetic acid, oxalic acid, benzoic acid, or a combination thereof.

12. The method of claim 1, wherein mechanical size reduction comprises cutting, steam explosion, acid-catalyzed steam explosion, or a combination thereof.

13. The method of claim 1, wherein heating of the hydrated biomass composition is at a temperature of from about 100° C. to about 250° C.

14. The method of claim 1, wherein heating of the hydrated biomass composition is performed at a pressure of from about 100 PSIG to about 150 PSIG.

15. The method of claim 1, wherein the time sufficient to produce the yield of C5 monosaccharides and/or disaccharides is from about 1 minute to about 30 minutes.

16. The method of claim 1, wherein pretreating the biomass composition further comprises dewatering the hydrated biomass composition to from about 10% to about 40% solids by dry biomass weight.

17. The method of claim 1, wherein heating comprises steam injection, steam explosion, acid-catalyzed steam explosion, or a combination thereof.

18. The method of claim 1, wherein the pretreating is performed in a continuous mode of operation.

19. The method of claim 1, wherein the pretreating is performed in a total time of from about 15 minutes to about 45 minutes.

20. The method of claim 1, wherein the one or more enzymes comprise one or more hemicellulases and/or one or more cellulases.

21. The method of claim 1, wherein the one or more enzymes are at a total level of from about 1% to about 20% w/w, about 1% to about 10% w/w, or about 1% to about 5% w/w by dry biomass weight.

22. The method of claim 1, further comprising adjusting the water content of the pretreated biomass composition to from about 5% to about 30% solids by dry biomass weight prior to hydrolyzing.

23. The method of claim 1, wherein the composition comprising C5 and C6 saccharides comprises glucose, xylose, mannose, galactose, rhamnose, arabinose, or a combination thereof.

24. The method of claim 1, wherein the composition comprising C5 and C6 saccharides comprises glucose in a yield that is greater than 55% of a theoretical maximum at 21 hours of hydrolysis.

25. The method of claim 1, wherein the biomass composition comprises alfalfa, algae, bagasse, bamboo, corn stover, corn cobs, corn kernels, corn mash, corn steep liquor, corn steep solids, distiller's grains, distiller's dried solubles, distiller's dried grains, condensed distiller's solubles, distiller's wet grains, distiller's dried grains with solubles, eucalyptus, food waste, fruit peels, garden residue, grass, grain hulls, modified crop plants, municipal waste, oat hulls, paper, paper pulp, prairie bluestem, poplar, rice hulls, seed hulls, silage, sorghum, straw, sugarcane, switchgrass, wheat, wheat straw, wheat bran, de-starched wheat bran, willows, wood, plant cells, plant tissue cultures, tissue cultures, or a combination thereof.

26. The method of claim 1, wherein mechanical size reduction does not comprise milling.

27. A composition comprising C5 and C6 saccharides produced by the method of claim 1.

28. A method of producing a composition comprising C5 and C6 saccharides and low levels of an inhibitor compound from a biomass composition comprising cellulose, hemicellulose, and/or lignocellulose, the method comprising:

(a) pretreating the biomass composition comprising cellulose, hemicellulose, and/or lignocellulose to produce a pretreated biomass composition comprising a mixture of solid particles, wherein at least 50% of the solid particles are less than 1.5 mm in a dimension, and C5 monosaccharides and/or disaccharides in a yield that is at least 50% of a theoretical maximum, wherein pretreating produces low levels of the inhibitor compound and comprises:

(i) hydration of the biomass composition in an acid medium to produce a hydrated biomass composition, (ii) mechanical size reduction of the hydrated biomass composition to produce the mixture of solid particles, wherein mechanical size reduction comprises cutting with a first rotating cutter and a second rotating cutter, and (iii) heating the hydrated biomass composition for a time sufficient to produce the pretreated biomass composition comprising C5 monosaccharides and/or disaccharides in the yield that is at least 50% of the theoretical maximum while producing low levels of the inhibitor compound; and (b) hydrolyzing the pretreated biomass composition with one or more enzymes for a time sufficient to produce the composition comprising C5 and C6 saccharides and low levels of the inhibitor compound.

29. The method of claim 1, wherein the dimension is diameter or length.

30. The method of claim 1, wherein the inhibitor compound is furfural.

* * * * *